(12) United States Patent
Takahashi

(10) Patent No.: US 6,666,860 B1
(45) Date of Patent: *Dec. 23, 2003

(54) ELECTRIC TREATMENT SYSTEM

(75) Inventor: Hiroyuki Takahashi, Akishima (JP)

(73) Assignee: Olympus Optical Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 88 days.

(21) Appl. No.: 09/640,039

(22) Filed: Aug. 16, 2000

(30) Foreign Application Priority Data

| Aug. 24, 1999 | (JP) | 11-237551 |
| Oct. 15, 1999 | (JP) | 11-294331 |
| Oct. 15, 1999 | (JP) | 11-294332 |
| Oct. 26, 1999 | (JP) | 11-304283 |
| Jun. 29, 2000 | (JP) | 2000-197252 |

(51) Int. Cl.$^7$ ................................................ A61B 18/04
(52) U.S. Cl. ........................................................ 606/34
(58) Field of Search ................................ 606/1, 10–12, 606/32–35, 38, 45–50

(56) References Cited

U.S. PATENT DOCUMENTS

| 5,318,516 A | * | 6/1994 | Cosmescu | 604/35 |
| 5,336,167 A | * | 8/1994 | Sullivan et al. | 604/22 |
| 5,383,874 A | * | 1/1995 | Jackson et al. | 606/1 |
| 5,462,522 A |   | 10/1995 | Sakurai et al. | 604/22 |
| 5,476,447 A |   | 12/1995 | Noda et al. | 604/26 |
| 5,562,503 A | * | 10/1996 | Ellman et al. | 200/51.03 |
| 5,797,901 A | * | 8/1998 | Cosmescu | 606/10 |
| 5,836,897 A |   | 11/1998 | Sakurai et al. | 601/2 |
| 6,155,975 A | * | 12/2000 | Urich et al. | 600/300 |
| 6,165,169 A | * | 12/2000 | Panescu et al. | 606/1 |
| 6,273,886 B1 | * | 8/2001 | Edwards et al. | 606/34 |
| 6,285,742 B1 | * | 9/2001 | Haumann et al. | 378/116 |
| 6,428,537 B1 | * | 8/2002 | Swanson et al. | 606/41 |

FOREIGN PATENT DOCUMENTS

| JP | 5049647 | 3/1993 |
| JP | 6-178780 | 6/1994 |
| JP | 2578250 | 11/1996 |
| JP | 2000-250 | 1/2000 |

* cited by examiner

Primary Examiner—Michael Peffley
Assistant Examiner—Peter J Vrettakos
(74) Attorney, Agent, or Firm—Ostrolenk, Faber, Gerb & Soffen, LLP

(57) ABSTRACT

A treatment tool for performing a treatment for a curative procedure with ultrasonic waves, high frequency current and so on is provided with an identifier formed of a resistor or the like for indicating the type of the treatment tool. A medical instrument such as an ultrasonic wave output apparatus discriminates the type of a treatment tool connected thereto from the identifier to automatically set operating parameters such as an output value suitable for the treatment tool and to associatively operate an ancillary medical instrument such as a perfusion/aspiration apparatus depending on the treatment tool, thereby reducing extra work such as manual setting to allow for a smooth treatment.

36 Claims, 28 Drawing Sheets

ELECTRIC TREATMENT SYSTEM

CROSS-REFERENCE TO RELATED APPLICATION

This application claims benefit of Japanese Application Nos. Hei 11-237551 filed in Japan on Aug. 24, 1999, Hei 11-294331 filed in Japan on Oct. 15, 1999, Hei 11-294332 filed in Japan on Oct. 15, 1999, Hei 11-304283 filed in Japan on Oct. 26, 1999, 2000-197252 filed in Japan on Jun. 29, 2000, the contents of which are hereby incorporated by reference.

BACKGROUND OF THE INVENTION

Field of the Invention and Description of the Related Art

The present invention relates to an electric treatment system for electrically performing a treatment for a curative procedure.

In recent years, electric treatment apparatus have been widely used. Examples of such are electric knives, which conduct a high frequency current to perform a treatment in a curative procedure, and ultrasonic treatment apparatus which utilize ultrasonic waves to perform a treatment an the curative procedure.

For example, an ultrasonic treatment apparatus disclosed in Japanese Patent No. 2578250 is composed of a hand piece, a probe, an ultrasonic wave output unit, a perfusion unit, and an aspiration unit. A resistor or a diode provided in the hand piece is used to sense the type of the hand piece. In addition, the type of prove is sensed by measuring the characteristic of the connected probe with a faint output.

The foregoing patent discloses an easy-to-use medical instrument, in which the ultrasonic wave output, the perfusion amount, and the aspiration amount are automatically set depending on the types of particular hand piece and the probe. An electric knife apparatus disclosed in Japanese Patent Laid-Open No. 2000-250 senses the type of an electrode connected thereto through a resistor provided in the electrode. Then, a driving signal for an electric knife is output in a mode according to the type of the electrode. The electric knife apparatus can switch among three modes: low impedance mode, middle impedance mode, and high impedance mode. This patent document discloses a medical instrument, in which an optimal output mode is automatically selected in accordance with the used electrode through the mode switching.

Also, Japanese Patent Laid-Open No. Hei 6-178780 relates to a cautery apparatus and a pneumoperitoneum apparatus, and discloses a device that maintains a clear field of view within a body cavity. Specifically, the pneumoperitoneum apparatus aspirates smoke produced by cautery within the body cavity in association with an output of the cautery apparatus, and instead feeds a gas to provide such clear field of view.

Further, an ultrasonic operation apparatus disclosed in Japanese Patent Laid-Open No. Hei 5-49647 discloses a device which can record the results of monitoring such as a period for which a hand piece has been used, a vibration conversion efficiency for voltage/current inputs, the amount of generated heat, and so on on a recording medium provided in the hand piece.

Japanese Patent No. 2578250 and Japanese Patent Laid-Open No. 2000-250 describe an ultrasonic operation apparatus and an electric knife apparatus, respectively, in which as a hand piece is connected to the apparatus, the type of the hand piece is sensed to automatically control output setting, perfusion setting, aspiration setting, output mode, and other parameter that are preferred for use with the hand piece.

The foregoing techniques work well as long as a single apparatus, i.e., the ultrasonic operation apparatus alone, or the electric knife apparatus alone is used. However, with recent advances in technologies and increasing complexity of techniques and devices, even when a hand piece is merely used, a plurality of devices must be controlled simultaneously, rather than a single device.

As an example of simultaneous control of plural devices, Japanese Patent Laid-Open No. Hei 6-178780 discloses an associative control of an electronic knife apparatus and a pneumoperitoneum apparatus.

In the disclosed associative control, remove the removing smoke produced by an electronic knife output from a body cavity, the pneumoperitoneum apparatus aspirates the smoke in association with the output and feeds a gas of an amount corresponding to the aspirated smoke. Here, the control is conducted on the assumption that the electric knife apparatus and the pneumoperitoneum apparatus are associated with each other, in other words, on the assumption that a hand piece for an endoscopic operation is used.

In practice, however, an electric knife may be used for incision and coagulation of skin in some cases. In this event, the electric knife is not used under an endoscope, therefor the operation of the pneumoperitoneum apparatus associated with the output may cause some trouble. For this reason, when the electric knife apparatus is not used under the endoscope, the electric knife apparatus must be disconnected from the pneumoperitoneum apparatus each time the electric knife apparatus is used alone.

In an operation field, such apparatus are typically concentrated on a single carrier or the like for connection, therefor a change in connection, if required each time the electric knife is not used under the endoscope, is troublesome for the user.

Since the apparatus disclosed in Japanese Patent Laid-Open No. Hei 5-49647 allows the past utilization log to be known, this is convenient for maintenance. However, each time the apparatus is used, the user must again perform settings, connections etc. for respective apparatus. The time-consuming and laborious work improve upon to the user does constitute a problem as is the case in the aforementioned Japanese Patent Laid-Open No. Hei 6-178780.

OBJECTS AND SUMMARY OF THE INVENTION

It is an object of the present invention to provide an electric treatment system that is capable of reducing work involved in changing connections and settings by controlling the operation of a medical instrument corresponding to a hand piece connected to the medical instrument, even when a different of types of hand pieces can be connected to a different of types of medical instruments.

It is another object of the present invention to provide an electric treatment system that is capable of smoothly performing a treatment and offering a good operability.

The present invention provides an electric treatment system which comprises:

a plurality of types of treatment tools each for performing a treatment for a curative procedure;

a plurality of types of medical instruments to which at least one of the plurality of types of treatment tools is selectively and removably connected, for electrically controlling an operation of the at least one treatment tool connected thereto;

an identifier provided in each of the plurality of types of treatment tools for identifying each treatment tool;

an identifier discriminating device provided in each of the plurality of types of medical instruments for discriminating at least the type of a connected treatment tool from the identifier; and a control unit for controlling operating parameters for a medical instrument to which a treatment tool is connected, from the result of determination by the identifier discriminating device, whereby a medical instrument to which a treatment tool is actually connected can perform a treatment with operating parameters suitable for the treatment tool.

BRIEF DESCRIPTION OF THE DRAWINGS

FIGS. 1 through 5 are diagrams related to a first embodiment of the present invention, wherein:

FIG. 1 is a functional block diagram illustrating an ultrasonic operation system according to the first embodiment;

FIG. 2 is a schematic diagram illustrating the structure of a connector;

FIG. 3 is a schematic diagram illustrating the structure of an ultrasonic coagulation/incision probe;

FIG. 4 is a schematic diagram illustrating the configuration of the ultrasonic operation apparatus when an ultrasonic aspiration probe is connected thereto; and FIG. 5 is a schematic diagram illustrating the configuration of an ultrasonic operation system according to a modification to the first embodiment;

FIGS. 7 through 9 are diagrams related to a third embodiment of the present invention, wherein:

FIG. 7 is a block diagram illustrating the configuration of an ultrasonic operation system according to the third embodiment;

FIG. 8 is a flow chart illustrating the contents of the operation performed by an ultrasonic wave output apparatus; and FIG. 9 is a block diagram illustrating the configuration of a perfusion/aspiration apparatus in a modification to the third embodiment;

FIGS. 11 through 19 are diagrams related to a fifth embodiment of the present invention, wherein:

FIG. 11 is a block diagram generally illustrating the configuration of an electric treatment system according to the fifth embodiment;

FIG. 12 is a block diagram illustrating the configuration of an electric knife apparatus;

FIG. 13 is a block diagram illustrating the configuration of an ultrasonic wave output apparatus;

FIG. 14 is a block diagram illustrating the configuration of a perfusion/aspiration apparatus;

FIG. 15 is a block diagram illustrating the configuration of a pneumoperitoneum apparatus;

FIG. 16 is a diagram illustrating different types of electric knife hand pieces;

FIG. 17 is a diagram illustrating different types of ultrasonic hand pieces;

FIG. 18 is a block diagram illustrating the configuration of a feature for discriminating a connected hand piece; and FIG. 19 is a block diagram illustrating the configuration associated with a storage unit provided in a hand piece in a modification to the fifth embodiment;

FIGS. 20 through 22 are diagrams related to a sixth embodiment of the present invention, wherein:

FIG. 20 is a diagram illustrating an appearance of an ultrasonic operation apparatus according to the sixth embodiment;

FIG. 21 is a functional block diagram illustrating the ultrasonic operation apparatus; and FIG. 22 is a diagram illustrating an appearance of an ultrasonic operation apparatus in a modification to the sixth embodiment;

FIGS. 23 through 25 are diagrams related to a seventh embodiment of the present invention, wherein:

FIG. 23 is a functional block diagram illustrating an ultrasonic operation apparatus according to the seventh embodiment;

FIG. 24 is a flow chart illustrating an initial setting routine for filling a passage with cooling water; and FIG. 25 is a diagram illustrating an appearance of a perfusion/aspiration apparatus;

FIGS. 26 through 28 are diagrams related to an eighth embodiment of the present invention, wherein:

FIG. 26 is a block diagram generally illustrating the configuration of an ultrasonic treatment apparatus according to the eighth embodiment of the present invention;

FIG. 27 is a flow chart illustrating the contents of processing performed by a perfusion/aspiration apparatus; and FIG. 28 is a flow chart illustrating the contents of processing performed by an ultrasonic operation apparatus; and FIGS. 29 and 30 are diagrams related to a ninth embodiment of the present invention, wherein:

FIG. 29 is a block diagram generally illustrating the configuration of a high frequency treatment system according to the ninth embodiment of the present invention; and FIG. 30 is a flow chart illustrating the contents of processing performed by the high frequency treatment apparatus (electric knife apparatus)

DETAILED DESCRIPTION OF THE PREFERRED EMBODIMENTS OF THE INVENTION

In the following, several embodiments of the present invention will be described with reference to the accompanying drawings.

(First Embodiment)

A first embodiment of the present invention will be described with reference to FIGS. 1 through 4. The description of the first embodiment will be focused on an ultrasonic operation system, as an electric treatment system directed by the present invention, for performing ultrasonic operations.

Figure 1:
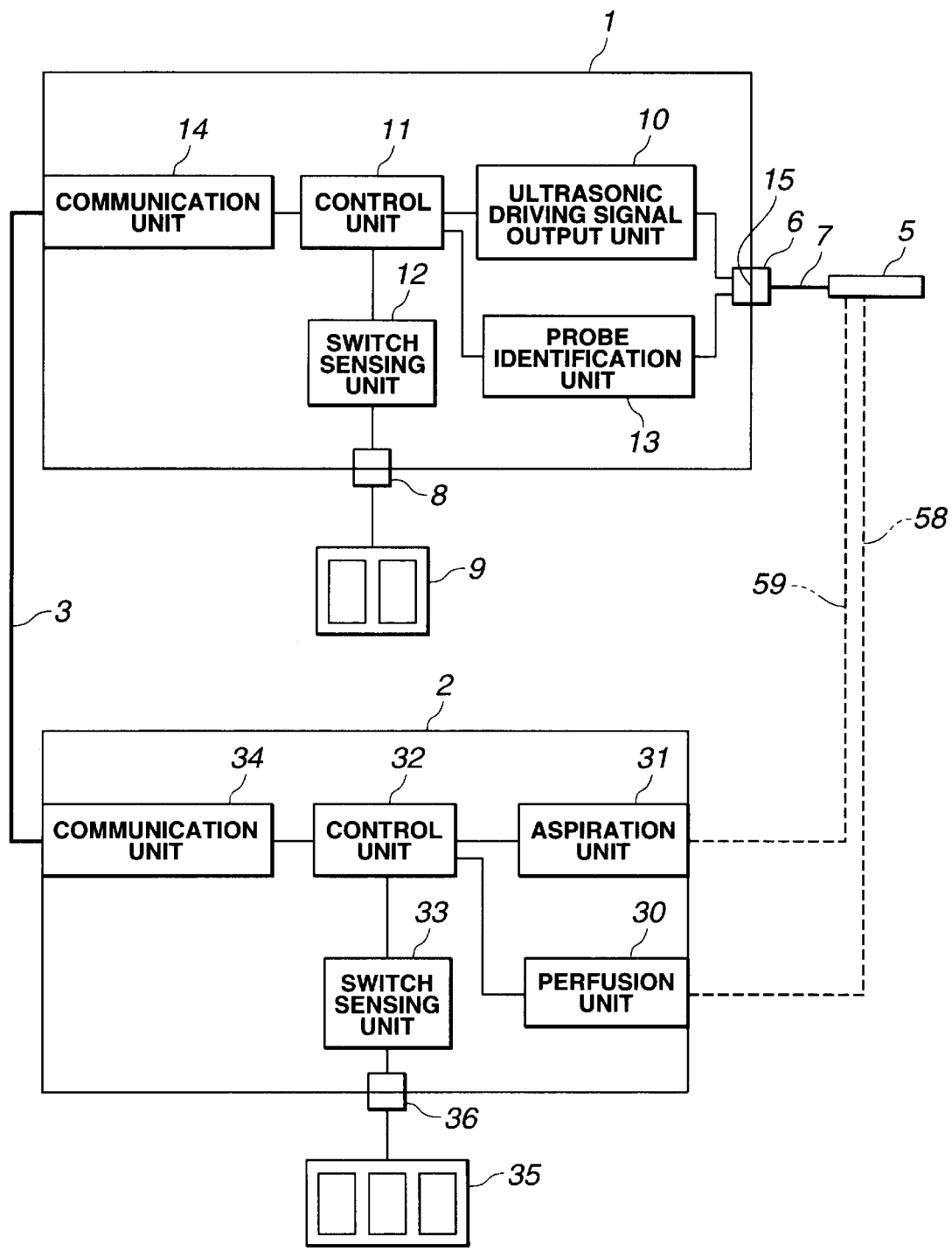

As illustrated in FIG. 1, the ultrasonic operation system of the first embodiment comprises an ultrasonic wave output apparatus 1, as a type of medical instrument, to which selectively connected is one of different types of hand pieces 5 as treatment tools such as an ultrasonic coagulation/ incision hand piece, an ultrasonic aspiration hand piece, etc., and which is capable of outputting an ultrasonic driving signal to the hand piece 5 connected thereto; and a perfusion/ aspiration apparatus 2, as an ancillary medical instrument, connected to the ultrasonic wave output apparatus 1 through a communication cable 3 for performing perfusion and aspiration for the hand piece 5.

Figure 3:
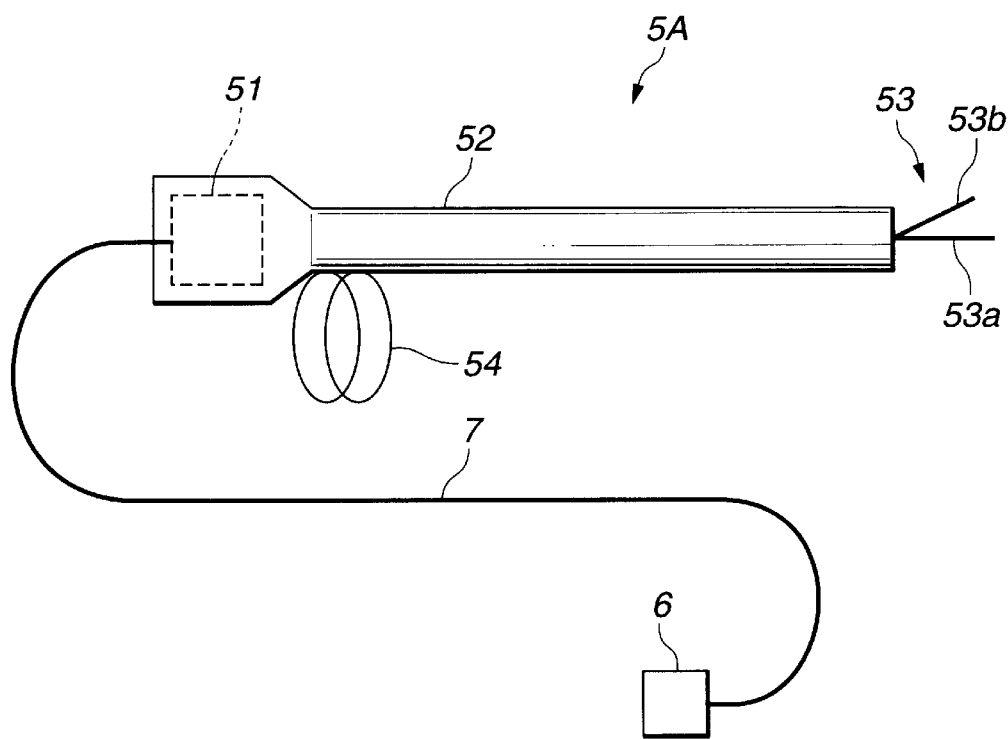

Here, as the hand piece 5, an ultrasonic coagulation/ incision hand piece 5A, for example, comprises an ultrasonic vibrator 51 inside a sheath 52 on the proximal end side, as illustrated in FIG. 3. Ultrasonic vibrations generated by the ultrasonic vibrator 51 are transmitted to a fixed blade 53a of a scissor-shaped probe 53 provided protrusively at the distal end of the sheath 52 through a transmission rod or the like, not shown. In addition, a movable blade 53b of the scissor-shaped probe 53 is provided at the distal end of the sheath 52, such that the movable blade 53b is opened and closed with respect to the fixed blade 53a, in association with a handle 54 provided on the sheath 52.

Figure 4:
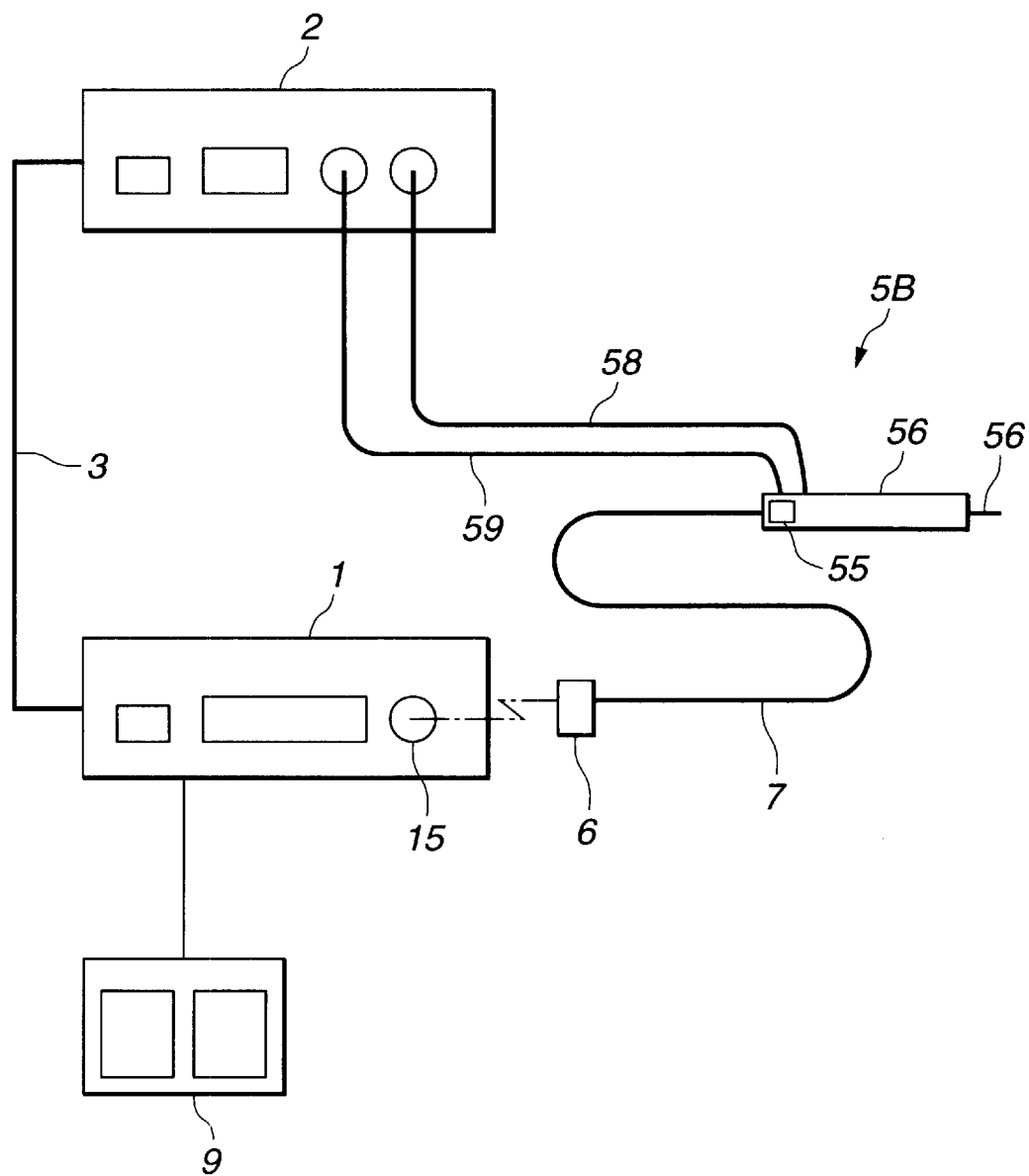

Also, as the hand piece 5, an ultrasonic wave aspiration hand piece 5B, for example, comprises an ultrasonic vibrator 55 inside a sheath 56 on the proximal end side, as illustrated in FIG. 4. Ultrasonic vibrations generated by the ultrasonic vibrator 55 are transmitted to an aspiration probe 57 protruded from the distal end of the sheath 56. The sheath 56 and the aspiration probe 57 are formed respectively with a perfusion path and an aspiration path, not shown, extending therethrough. The perfusion path and the aspiration path communicate respectively with a perfusion tube 58 and an aspiration tube 59 which extend from the sheath 56.

From each of the proximal ends of the sheaths 52, 56, a cable 7 extends for transmitting an ultrasonic driving signal to the ultrasonic vibrator 51 or 55. The cable 7 can be connected to an output port 15 of the ultrasonic wave output apparatus 1 through a connector 6 disposed at the end thereof.

Figure 2:
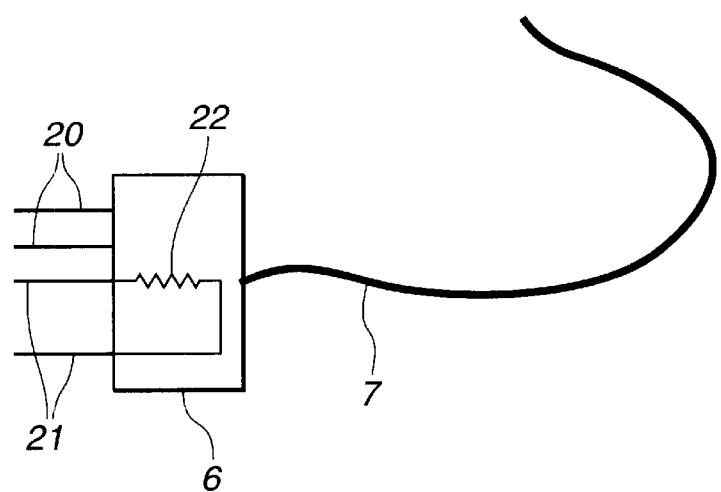

As illustrated in FIG. 2, the connector 6 comprises a driving signal transmission pin 20 for transmitting an ultrasonic driving signal output from the ultrasonic wave output apparatus 1 to the cable 7; and a probe identifying pin 21 for transmitting information on a probe associated with the hand piece 5, the ultrasonic wave output apparatus 1.

The connector 6 also contains a probe identifying resistor 22 which has a unique resistance value that differs from one probe to another. The probe identifying resistor 22 is connected to the probe identifying pin 21. It should be noted that the probe identifying pin 21 may be disposed in the sheaths 52, 56, in which case, the probe identifying resistor 22 is connected to the probe identifying pin 21 through the cable 7.

The ultrasonic wave output apparatus 1 comprises an ultrasonic driving signal output unit 10 capable of outputting an ultrasonic driving signal to a hand piece connected thereto; a control unit 11 for controlling the ultrasonic driving signal output unit 10; a switch detection unit 12 for detecting a manipulation signal from a foot switch 9 removably connected to the ultrasonic wave output apparatus 1 through a connector 8 for turning ultrasonic waves ON/OFF, and other switches, not shown, or the like; a probe identification unit (probe identifying means) 13 for detecting the resistance of the probe identifying resistor 22 to identify the type of the connected hand piece 5 (probe); and a communication unit 14 for transmitting and receiving data to and from the perfusion/aspiration apparatus 2.

The perfusion/aspiration apparatus 2 comprises a perfusion unit 30 capable of supplying saline or the like to the hand piece 5 through the perfusion tube 58; an aspiration unit 31 capable of aspirating treated vital tissue, body fluid and so on through the aspiration tube 59; a control unit 32 for controlling the perfusion unit 30 and the aspiration unit 31; a switch detection unit 33 for detecting a manipulation signal from a foot switch 35 removably connected to the perfusion/aspiration apparatus 2 through a connector 36, other switches, not shown, or the like; and a communication unit 34 for transmitting and receiving data to and from the ultrasonic wave output apparatus 1.

The foot switch 35, which is provided for turning ultrasonic waves ON/OFF like the foot switch 9, has a function for turning perfusion ON/OFF and another function for turning aspiration ON/OFF, therefore, the foot switch 35 may be omitted if it is not necessary to selectively turn ON/OFF only perfusion or only aspiration.

The contents of data transmitted and received between the ultrasonic wave output apparatus 1 and the perfusion/ aspiration apparatus 2 may include: the type of the hand piece 5; whether or not associative control is required for the perfusion/aspiration apparatus 2; the perfusion amount by the perfusion/aspiration apparatus 2; control information such as an aspiration pressure, the type of abnormality, and etc. control information such as a setting for the ultrasonic wave output of the ultrasonic output apparatus 1, the type of abnormality, and etc.; information on the ON/OFF state of the foot switch 9, and so on.

Next, the operation of the first embodiment will be described.

For performing an ultrasonic coagulation/incision treatment, an operator first connects the ultrasonic coagulation/incision hand piece 5A to the ultrasonic wave output apparatus 1 through the connector 6. Next, the operator manipulates the handle 54 to open and close the scissor-shaped probe 53 to clamp a vital tissue of interest. In this state, the operator actuates the foot switch 9 to drive the ultrasonic vibrator 51 to coagulate and incise the clamped vital tissue with ultrasonic vibrations.

For performing an ultrasonic aspiration treatment, on the other hand, the operator first connects the ultrasonic aspiration hand piece 5B to the ultrasonic wave output apparatus 1 through the connector 6, and connects the perfusion tube 58 and the aspiration tube 59 of the ultrasonic aspiration hand piece 5B to the perfusion/aspiration apparatus 2.

Next, the operator brings the aspiration probe 57 into contact with a vital tissue of interest, and actuates the foot switch 9 or 35 to drive the ultrasonic vibrator 55 to destroy or emulsify the vital tissue of interest.

In this event, the perfusion/aspiration apparatus 2 is simultaneously controlled in association with the ultrasonic wave output apparatus 1 to supply cooling water such as saline or the like to the aspiration probe 57 through the perfusion tube 58, the cooling water is then aspirated through the aspiration tube 59. This prevents of the aspiration probe 57 from heating; washing of the vital tissue of interest; and aspiration of the destroy or emulsified vital tissue and the cooling water (washing water). In addition, only one of perfusion and aspiration may be performed through certain operation of the foot switch 35.

(Operations of Ultrasonic Wave Output Apparatus 1 and Perfusion/Aspiration apparatus 2)

As the hand piece 5 is connected to the ultrasonic wave output apparatus 1, the ultrasonic wave output apparatus 1 first identifies the type of the connected hand piece 5 (probe)

by the probe identification unit 13. Specifically, the probe identification unit 13 outputs a probe identifying signal to the hand piece 5 to identify the type of the hand piece 5 by a response from the hand piece 5.

More specifically, the probe identification unit 13 outputs a constant current to a probe identification pin 21, and detects a voltage generated across a probe identifying resistor 22 to identify the type of the hand piece 5. Alternatively, the probe identification unit 13 outputs an alternate current to the probe identification pin 21, and detects an alternating current voltage generated across the probe identifying resistor 22 to identify the type of the hand piece 5.

Next, the ultrasonic wave output apparatus 1 determines in the control unit 11 whether or not associative control of the perfusion/aspiration apparatus 2 with the ultrasonic wave output apparatus 1 is required in accordance with the type of the hand piece 5, and outputs a signal indicative of whether the associative control is required or not be to the perfusion/aspiration apparatus 2 through the communication unit 14.

In this event, when the probe identification unit 13 identifies that the connected hand piece 5 is an ultrasonic coagulation/incision hand piece 5A, the control unit 11 outputs an associative control release signal to the perfusion/aspiration apparatus 2. Then, in this state, when the switch detection unit 12 detects an ultrasonic ON signal from the foot switch 9, the control unit 11 outputs an ultrasonic driving signal to the ultrasonic vibrator 51 through the ultrasonic driving signal output unit 10. At this time, even if an abnormal signal is input from the perfusion/aspiration apparatus 2, the driven ultrasonic vibrator 51 will not be interrupted.

On the other hand, when the probe identification unit 13 identifies that the connected hand piece 5 is an ultrasonic aspiration hand piece 5B, the control unit 11 outputs a signal to the perfusion/aspiration apparatus 2 for enabling the associative control. Then, in this state, when the switch detection unit 12 or 33 detects an ultrasonic ON signal from the foot switch 9 or 35, the control unit 11 outputs an ultrasonic driving signal to the ultrasonic vibrator 55 through the ultrasonic driving signal output unit 10.

Simultaneously, the control unit 32 drives the perfusion unit 30 and the aspiration unit 31 in association with the ultrasonic wave output apparatus 1 to control perfusion and aspiration. In this event, if the perfusion/aspiration apparatus 2 fails, the control unit 11 immediately stops outputting the ultrasonic driving signal to the ultrasonic vibrator 55. Similarly, if the ultrasonic wave output apparatus 1 fails, the control unit 32 immediately stops the perfusion and aspiration.

Here, in the perfusion/aspiration apparatus 2, the perfusion amount and aspiration pressure are set by switches or the like, not shown, such that the control unit 32 controls the perfusion amount from the perfusion unit 30, and the aspiration pressure in the aspiration unit 31 in accordance with the states of the switches detected by the switch detection unit 33.

Alternatively, the perfusion/aspiration apparatus 2 may read the perfusion amount and an aspiration pressure previously stored in a memory in response to the probe identifying signal detected by the probe identification unit 13 to control the perfusion unit 30 and the aspiration unit 31.

The first embodiment has the following advantages.

According to the first embodiment as described above, since the type of a hand piece (probe) connected to the ultrasonic wave output apparatus is identified to determine whether or not the associative control of the ultrasonic wave output apparatus with the perfusion/aspiration apparatus is required in accordance with the identified type of the hand piece, unintended perfusion and aspiration functions will not operate when ultrasonic waves are output. Also, this eliminates time-consuming and laborious works for re-connection of the ultrasonic wave output apparatus and the perfusion/aspiration apparatus in accordance with the type of a particular probe, so that the operability can be improved during an ultrasonic operation.

Also, by selectively performing the associative control in accordance with a connected hand piece, if the ultrasonic wave output apparatus and/or the perfusion/aspiration apparatus fail, the hand piece for use only with a single apparatus will not be affected by the other failed apparatus.

Next, a modification to the first embodiment of the present invention will be described with reference to FIG. 5, which generally illustrates the configuration of an ultrasonic operation system.

Figure 5:
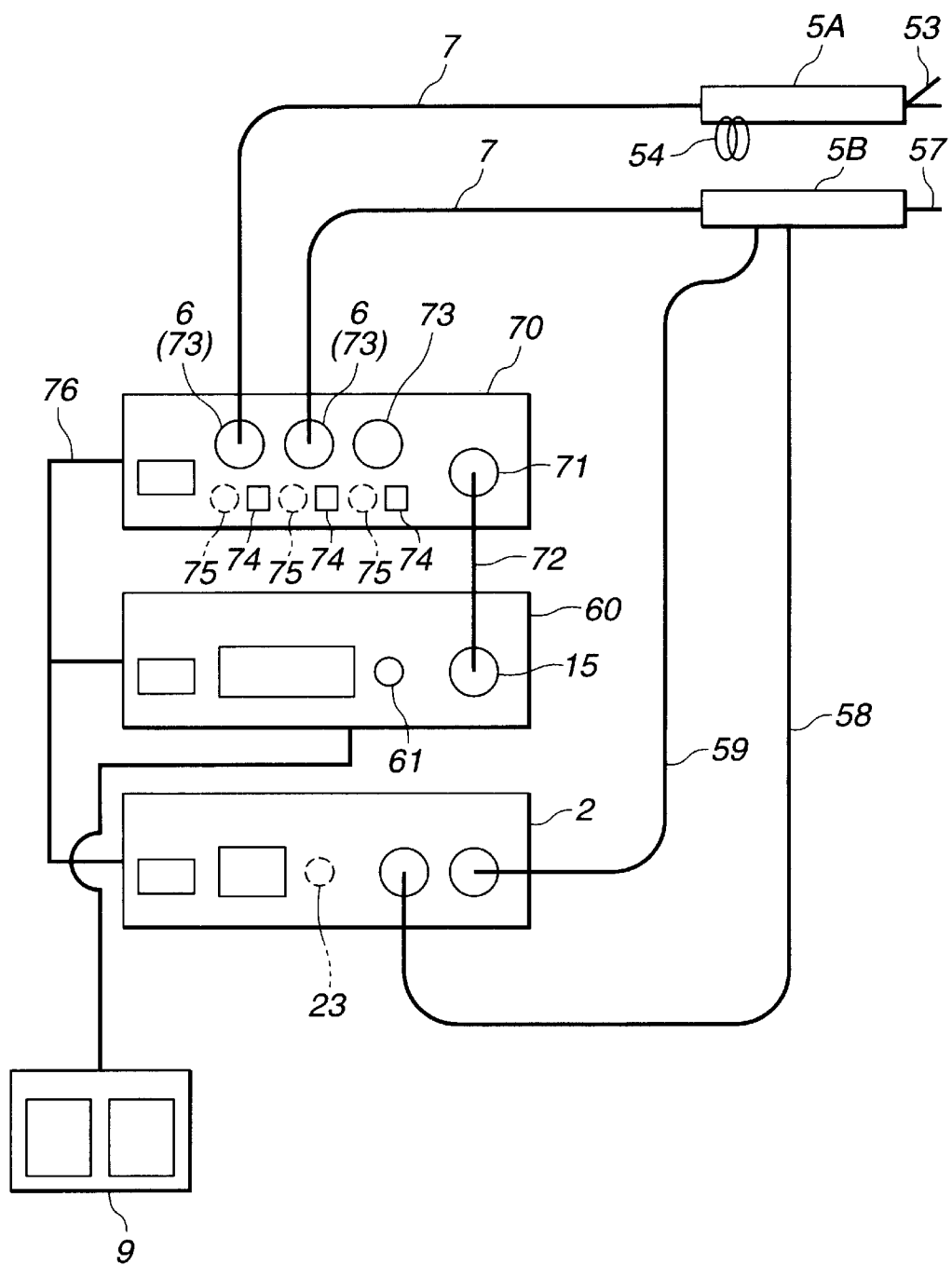

In the foregoing first embodiment, the probe identification unit 13 is provided for identifying the type of a probe used with the hand piece 5, such that the ultrasonic wave output apparatus 1 determines whether or not the associative control with the perfusion/aspiration apparatus 2 is required in accordance with the type of the probe identified by the probe identification unit 13, whereas in the modification, the probe identification unit 13, the probe identification pin 21, and the probe identifying resistor 22 are eliminated, and an ultrasonic wave output apparatus 60 is provided with an associative control switch 61 for the operator to manually perform switching control, as illustrated in FIG. 5.

Also, the ultrasonic operation system according to the modification has an output switching apparatus (output switching means) 70 which can be connected simultaneously with a plurality of hand pieces 5.

The output switching apparatus 70 comprises an input port 71 which can be connected to an output port 15 of the ultrasonic wave output apparatus 60 through a cable 72; an output port 73 which can be connected simultaneously with a plurality of hand pieces (three in the illustrated example); an output port selecting switch 74 positioned near each output port 73 for selectively switching a used output port 73 (hand piece 5).

These ultrasonic wave output apparatus 60, output switching apparatus 70, and the perfusion/aspiration apparatus 2 are connected through a communication cable 76.

Also, as illustrated in FIG. 5, an ultrasonic coagulation/incision hand piece 5A and an ultrasonic aspiration hand piece 5B, for example, are removably connected to the respective output ports 73 of the output switching apparatus 70 through associated connectors 6. The number of connected hand pieces is limited to the number of the output ports.

Further, when a connected hand piece is a hand piece which is provided with perfusion and aspiration functions as the ultrasonic aspiration hand piece 5B, a perfusion tube 58 and an aspiration tube 59 of the hand piece are connected to the perfusion/aspiration apparatus 2.

Next, the operation of the modification will be described.

For performing an ultrasonic coagulation/incision treatment, the operator first manipulates the output port selecting switch 74 to select an output port 73 which is connected to the ultrasonic coagulation/incision hand piece 5A. Next, the operator manipulates the associative control switch 61 to turn OFF the associative control of the perfusion/aspiration apparatus 2 with the ultrasonic wave output apparatus 60. Further, the operator manipulates the handle 54 to open and close a scissor-shaped probe 53 to clamp a vital tissue of interest. In this state, the operator actuates the foot switch 9 to drive the ultrasonic vibrator to coagulate and incise the clamped vital tissue with ultrasonic vibrations.

For performing an ultrasonic aspiration treatment, on the other hand, the operator first manipulates the output port selecting switch 74 to select an output port 73 which is connected to the ultrasonic aspiration hand piece 5B. Next, the operator manipulates the associative control switch 61 to turn ON the associative control of the perfusion/aspiration apparatus 2 with the ultrasonic wave output apparatus 60. Further, the operator brings the aspiration probe 57 into contact with a vital tissue of interest, and actuates the foot switch 9 to drive the ultrasonic vibrator to destroy or emulsify the vital tissue of interest.

In this event, the perfusion/aspiration apparatus 2 is simultaneously controlled in to supply cooling water such as saline or the like to the aspiration probe 57 through the perfusion tube 58, to cooling water is then aspirated through the aspiration tube 59. This prevents of the aspiration probe 57 from heating; washing of the vital tissue of interest; and aspiration of the destroy or emulsified vital tissue and the cooling water (washing water).

In this event, if the ultrasonic wave output apparatus 60, the perfusion/aspiration apparatus 2 or the like fails, the respective apparatus is notified to that effect through the communication cable 76 to stop the control such as ultrasonic wave output, and the user is also notified of the failure.

This modification has the following advantages.

According to the modification described above, the provision of the associative control switch enables the operator to directly determine whether or not the associative control is required, and set accordingly.

Also, the addition of the output switching apparatus enables a plurality of hand pieces to be connected simultaneously to a single ultrasonic wave output apparatus, thus improving operability.

Further, since the associative control can be selected, the perfusion/aspiration apparatus need not be removed from the ultrasonic wave output apparatus in accordance with a particular probe.

Here, as indicated by broken lines in FIG. 5, an associative control switch (associative switching means) 23 may be provided on the perfusion/aspiration apparatus 2 in place of the associative control switch 61 provided on the ultrasonic wave output apparatus 60, or an associative control switch 75 may be provided on the output switching apparatus 70.

With the configuration described above, similar advantages to the above can also be provided. Particularly, when the associative control switch 75 is provided for each output port 73 of the output switching apparatus 70, the associative control can be previously set ON/OFF for each output port 73, thus further improving the operability.

It should be noted that in the modification, the ultrasonic wave output apparatus 60 may be provided with a probe identification unit, similar to that used in the aforementioned first embodiment.

In this case, a plurality of different types of hand pieces can be simultaneously connected to and used with the ultrasonic wave output apparatus, in addition to the advantages provided by the aforementioned first embodiment.

Although the first embodiment and the modification thereto realize an ultrasonic operation system which determines whether or not the associative control with the perfusion/aspiration apparatus 2 is required, when a plurality of hand pieces 5 are used in order provide to the user with high operability, the perfusion tube 58 and the aspiration tube 59 must be connected again to the perfusion/aspiration apparatus 2 for using a plurality of ultrasonic aspiration hand pieces 5B.

In view of this inconvenience, an implementation of the ultrasonic operation system capable of further improving the operability will be described in the following second embodiment.

(Second Embodiment)

Figure 6:
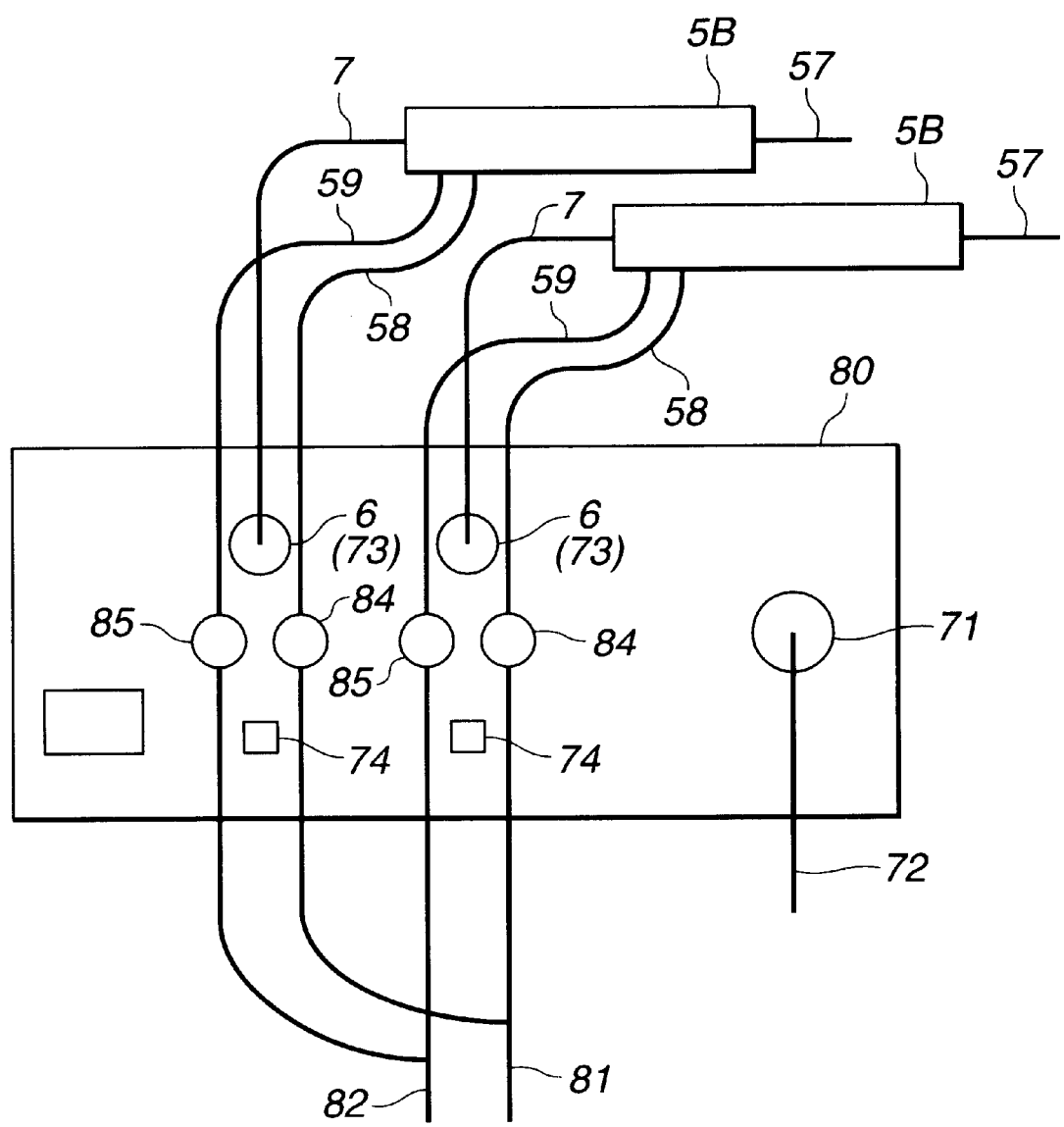
FIG. 6 is a schematic diagram illustrating an output switching apparatus in a second embodiment of the present invention.

FIG. 6 is a schematic diagram illustrating an output switching apparatus according to the second embodiment of the present invention.

The ultrasonic operation system according to the second embodiment comprises an output switching apparatus 80, as illustrated, in place of the output switching apparatus 70 which has been illustrated in the modification. The output switching apparatus 80 comprises an input port 71 which can be connected to an output port of an ultrasonic wave output apparatus, not shown through a cable 72; output ports 73 for simultaneously connecting a plurality of (two in the illustrated example) hand pieces; perfusion pinch valves 84 and aspiration pinch valves 85 positioned near the respective output ports 73; and output ports selecting switch 74 positioned near the respective output port 73 for selectively switching one output port 73 (hand piece 5) to be used.

Each of the perfusion pinch valves 84 is removably connected to a perfusion unit of a perfusion/aspiration apparatus, not shown through a perfusion tube 81 which is branched in the midway near one end thereof into a plurality of branch paths corresponding to the number of perfusion pinch valves 84.

Each of the aspiration pinch valves 85 is removably connected to an aspiration unit of the perfusion/aspiration apparatus, not shown, through an aspiration tube 82 which is branched in the midway near one end thereof into a plurality of branch paths corresponding to the number of aspiration pinch valves 85.

For example, as illustrated in FIG. 6, a number of ultrasonic aspiration hand pieces 5B, within the number of output ports, are removably connected to the output ports 73 of the output switching apparatus 80 through connectors 6. In this event, the perfusion tubes 58 and the aspiration tubes 59 of the ultrasonic aspiration hand pieces 5B are connected to the perfusion/aspiration apparatus through the perfusion pitch valves 84 and the aspiration pinch valves 85.

Though not shown, ultrasonic coagulation/incision hand pieces 5A may be connected to the output ports 73 of the output switching apparatus 80.

Next, the operation of the second embodiment will be described.

As selection is made by the output port selecting switch 74 to the output port 73 connected to the ultrasonic aspiration hand piece 5B, the output switching apparatus 80 switches the perfusion pitch valves 84 and the aspiration pinch valves 85 to open only the perfusion pitch valve 84 and the aspiration pinch valve 85 corresponding to the selected output port 73, so that they communicate with a perfusion unit and an aspiration unit of a perfusion/aspiration apparatus, not shown.

In this way, only when selection is made to the output port 73, which is connected to the ultrasonic aspiration hand piece 5B, the output switching apparatus 80 enables perfusion and aspiration operations associated with an ultrasonic wave output or perfusion and aspiration operations in accordance with the foot switch.

The second embodiment has the following advantages.

According to the second embodiment as described above, when a plurality of ultrasonic aspiration hand pieces 5B are used, the re-connection of the cable 7 the re-connection of the perfusion tube 58 and the inconnections of the aspiration tube 59 are eliminated, thereby making it possible to further improve the operability, in addition to the advantages provided in the respective embodiments described above.

(Third Embodiment)

Next, a third embodiment of the present invention will be described with reference to FIGS. 7 through 9.

Figure 7:
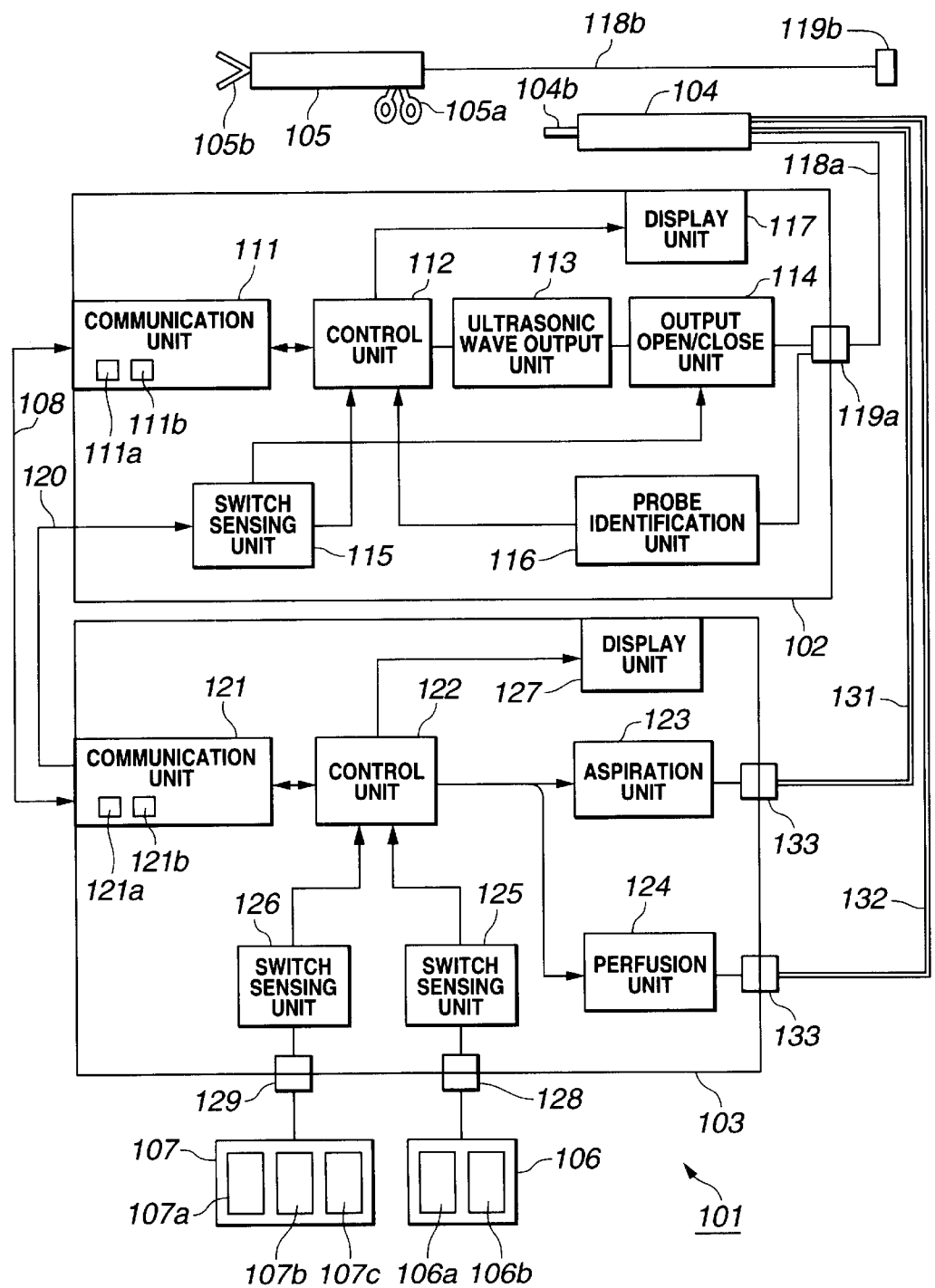

An ultrasonic operation system 101 illustrated in FIG. 7 comprises an ultrasonic wave output apparatus 102 for outputting an ultrasonic driving signal and for controlling the output; a perfusion/aspiration apparatus 103 connected to the ultrasonic wave output apparatus 102 through a communication cable 108 for performing perfusion and aspiration; an ultrasonic aspiration probe 104 removably connected to the ultrasonic wave output apparatus 102 and to the perfusion/aspiration apparatus 103, for example, as an ultrasonic treatment tool is grabbed by the operator for performing an ultrasonic treatment, for performing an ultrasonic-based aspiration treatment; an ultrasonic coagulation/incision probe 105 removably connected to the ultrasonic wave output apparatus 102 for performing ultrasonic-based coagulation and incision treatments; a twin foot switch 106 connected to the perfusion/aspiration apparatus 103 for controlling and manipulating the ultrasonic wave output apparatus 102; and a triple foot switch 107 for controlling and manipulating both the ultrasonic wave output apparatus 102 and the perfusion/aspiration apparatus 103.

In FIG. 7, the ultrasonic aspiration probe 104 is connected to the ultrasonic wave output apparatus 102 and to the perfusion/aspiration apparatus 103, in which case, an ultrasonic aspiration operation apparatus is implemented. Alternatively, when the ultrasonic coagulation/incision probe 105 is connected to the ultrasonic wave output apparatus 102, an ultrasonic coagulation/incision operation apparatus is implemented.

When the ultrasonic aspiration probe 104 is connected, an aspiration treatment can be performed from a distal treatment end 104a by ultrasonic vibrations. Alternatively, with the ultrasonic coagulation/incision probe 105, a handle 105a is manipulated to open and close a scissor-like treatment tool 105b at the distal end of the probe 105 to clamp a portion of tissue of interest which can be coagulated or incised by the probe 105.

The ultrasonic wave output unit 102 comprises a communication unit 111 for bidirectionally communicating with (a communication unit 121 of) the perfusion/aspiration apparatus 103 through a communication cable 108; a control unit 112 connected to the communication unit 111 for controlling the communications; an ultrasonic wave output unit 113 connected to the control unit 112 so that the amount of output therefrom is controlled by the control unit 112; an output open/close port 114 connected to an output terminal of the ultrasonic wave output unit 113 for opening and closing the output; a switch sensing unit 115 for sensing an operation on a foot switch; a probe identification unit 116 for identifying a connected ultrasonic treatment tool, more specifically, at least the ultrasonic aspiration probe 104 or the ultrasonic coagulation/incision probe 105; and a display unit for displaying an error or the like.

The output open/close port 114 is provided at an output end thereof with a connector receptor to which the connector of each ultrasonic probe is removably connected. More specifically, a connector 119a of an ultrasonic driving output cable 118a connected to the ultrasonic aspiration probe 104, and a connector 119b of an ultrasonic driving output cable 118b connected to the ultrasonic coagulation/incision probe 105 are selectively and removably connected to the connector receptor.

Also, an input terminal of the probe identification unit 116 is connected to the connector receptor, so that the probe identification unit 116 identifies an ultrasonic probe including a connector 119i (i=a or b) connected to the connector receptor, and sends the result of the identification to the control unit 112, causing the control unit 112 to perform an appropriate control operation in accordance with the result.

For this identification, the connectors 119i of the ultrasonic aspiration probe 104 and the ultrasonic coagulation/incision probe 105 are each provided with a unique resistor for identification. The probe identification unit 116 applies a current flow through the resistor to measure or compare a generated voltage by means of a comparator or the like, and recognizes the type of the ultrasonic probe, i.e., whether the connected ultrasonic probe is the ultrasonic aspiration probe 104 or the ultrasonic coagulation/incision probe 105. For this purpose, the connectors of different types of ultrasonic probes (having different treatment functions through ultrasonic waves) are provided with identifying resistors which have different resistance values, respectively.

This identification information is used to determine whether to operate the perfusion/aspiration apparatus 103 in association or disable the associative operation, as will be later described.

In addition, the identified information can also be relied on to control operating parameters for a connected probe, for example, a driving frequency when ultrasonic waves are output, switching of an upper limit and a lower limit for the driving output, etc.

The output open/close port 114 is also applied with information from the switch sensing unit 115 which has sensed an ON/OFF state of the foot switch (ON/OFF state of a pedal switch), such that the output open/close port 114 opens or closes (turns ON/OFF) a relay switch, which forms part of the output open/close port 114, in response to this information.

The perfusion/aspiration apparatus 103 connected to the ultrasonic wave output apparatus 102 through the communication cable 108 comprises a communication unit 121 connected to the communication unit 111 of the ultrasonic wave output apparatus 102 and to the switch sensing unit 115 through the communication cable 108 and a switch cable 120, respectively; a control unit 122 connected to the communication unit 121 for controlling communications and so on; an aspiration unit 123 for performing an aspiration operation under the control of the control unit 122; a perfusion unit 124 for performing a perfusion operation under the control of the control unit 122; switch sensing units 125, 126 connected to the control unit 122 for sensing an ON/OFF state of the twin switch 106 and an ON/OFF state of the triple switch 107; and a display unit 127 for displaying an error and so on.

The communication unit 111 of the ultrasonic wave output apparatus 102 and the communication unit 121 of the perfusion/aspiration apparatus 103 have unique ID information generators 111a, 121a, respectively, for sending ID information to a destination device connected through the communication cable 108 and for receiving ID information transmitted from the destination device to identify the destination device connected thereto, including the type thereof.

The switch sensing units 125, 126 each have a connector receptor to which a connector 128 or 129 of the twin switch 106 or the triple switch 107 is removably connected.

The twin foot switch 106 is comprised of a setting output pedal 106a and a full (100%) output pedal 106b, while the triple foot switch 107 is comprised of a perfusion pedal 107a, an aspiration pedal 107b, and an (ultrasonic) output pedal 107c.

An aspiration pipe sleeve 133 and a perfusion pipe sleeve 134 at rear ends of an aspiration tube 131 and a perfusion tube 132, connected to the ultrasonic aspiration probe 104 having perfusion and aspiration passages, are removably connected to an aspiration pipe sleeve receptor and a perfusion pipe sleeve receptor of the aspiration unit 123 and the perfusion unit 124, respectively.

Thus, a liquid can be supplied (perfused) from the perfusion unit 124 to the ultrasonic aspiration probe 104 through the perfusion tube 132, while fluids such as the liquid supplied through the aspiration tube 131, body fluids, and so on can be aspirated to the aspiration unit 123 through the aspiration tube 131 for recovery.

On the other hand, the ultrasonic coagulation/incision probe 105 has the ultrasonic driving output cable 118b with the connector 119b removably connected to the ultrasonic wave output apparatus 102, and does not have a perfusion feature or an aspiration feature connected to the perfusion/aspiration apparatus 103.

With the configuration described above, the third embodiment is characterized in that when the ultrasonic wave output apparatus 102 and the perfusion/aspiration apparatus 103 are connected through the communication cable 108, both parties mutually identify the types of apparatus connected thereto through transmission and reception of ID information (which also includes information on the type of apparatus) between the communication units 111 and 121, so that the functions provided by both the ultrasonic wave output apparatus 102 and the perfusion/aspiration apparatus 103 can be controlled and operated in an associative manner through transmission by way of the communication cable 108 and the switch cable 120, and the probe identifying information of the probe identification unit 116 is used to perform a control operation to enable the associative control when the ultrasonic aspiration probe 104 is connected to the ultrasonic wave output apparatus 102 as the ultrasonic probe, and to perform a control operation to disable the associative control when the ultrasonic coagulation/incision probe 105 is connected to the ultrasonic wave output apparatus 102 as the ultrasonic probe (operation for disabling the associative control).

The twin foot switch 106 is a switch which is only related to the ultrasonic wave output apparatus 102, while the triple foot switch 107 is a switch which is related to both the perfusion/aspiration apparatus 103 and the ultrasonic wave output apparatus 102.

Then, as the probe identification unit 116 identifies that the ultrasonic aspiration probe 104 is connected to the ultrasonic wave output apparatus 102, the control unit 112 sends a signal for performing the associative control to the control unit 122 of the perfusion/aspiration apparatus 103 through the communication cable 108. In response, the control unit 122 brings itself into a state for the associative control with the ultrasonic wave output apparatus 102.

In this case, the control unit 122 of the perfusion/aspiration apparatus 103 is in a state to perform a control operation for only accepting operations on the triple foot switch 107 related to the functions of both the ultrasonic wave output apparatus 102 and the perfusion/aspiration apparatus 103, and accepting no operation on the twin foot switch 106 related only to the function of the ultrasonic wave output apparatus 102.

On the other hand, as the probe identification unit 116 identifies that the ultrasonic coagulation/incision probe 105 is connected to the ultrasonic wave output apparatus 102, the control unit 112 sends a signal for disabling the associative control to the control unit 122 of the perfusion/aspiration apparatus 103 through the communication cable 108. In response, the control unit 122 brings itself into a state in which the associative control with the ultrasonic wave output apparatus 102 is disabled.

In this case, the control unit 122 of the perfusion/aspiration apparatus 103 is in a state in which the control unit 122 only accepts operations on the twin foot switch 106 and does not accept operations on the triple foot switch 107. Then, when the twin foot switch 106 is actuated, the operation is simply transmitted to the ultrasonic wave output apparatus 102 which in turn performs a control operation corresponding to the operation on the twin foot switch 106.

In this way, a signal based on identification information on the ultrasonic probe as an ultrasonic treatment tool is sent from the ultrasonic wave output apparatus 102 to the perfusion/aspiration apparatus 103, such that the perfusion/aspiration apparatus 103 enables or disables the associative control in response to the signal sent thereto. Thus, with the triple foot switch 107 for enabling the associative control and the twin foot switch 106 for disabling the associative control connected to the perfusion/aspiration apparatus 103, operations on a foot switch corresponding to a sent signal are accepted by the perfusion/aspiration apparatus 103. Therefore, the user is not required to selectively connect a foot switch in accordance with an ultrasonic probe to be used or remove a foot switch not to be used, resulting in a configuration of higher usability.

Next, the operation of the ultrasonic operation system 101 will be described.

As the ultrasonic wave output apparatus 102 is connected to the perfusion/aspiration apparatus 103 through the communication cable 108, the communication units 111, 121 communicate with each other to identify the destination apparatus connected thereto. In this event, the communication may be either serial or parallel.

When none of apparatus (devices) is not connected, they transmit their IDs at regular intervals. When no destination device is connected, no response is provided, so that it is recognized that no destination device is connected.

When a destination device is connected, its ID is returned from the device. This enables recognition as to whether a destination device is connected, and which device is connected.

The communications of the IDs may be performed at regular intervals even after a connection is established to sense physical states such as whether a device, once connected, has been removed, or whether communications are normally made.

Figure 8:
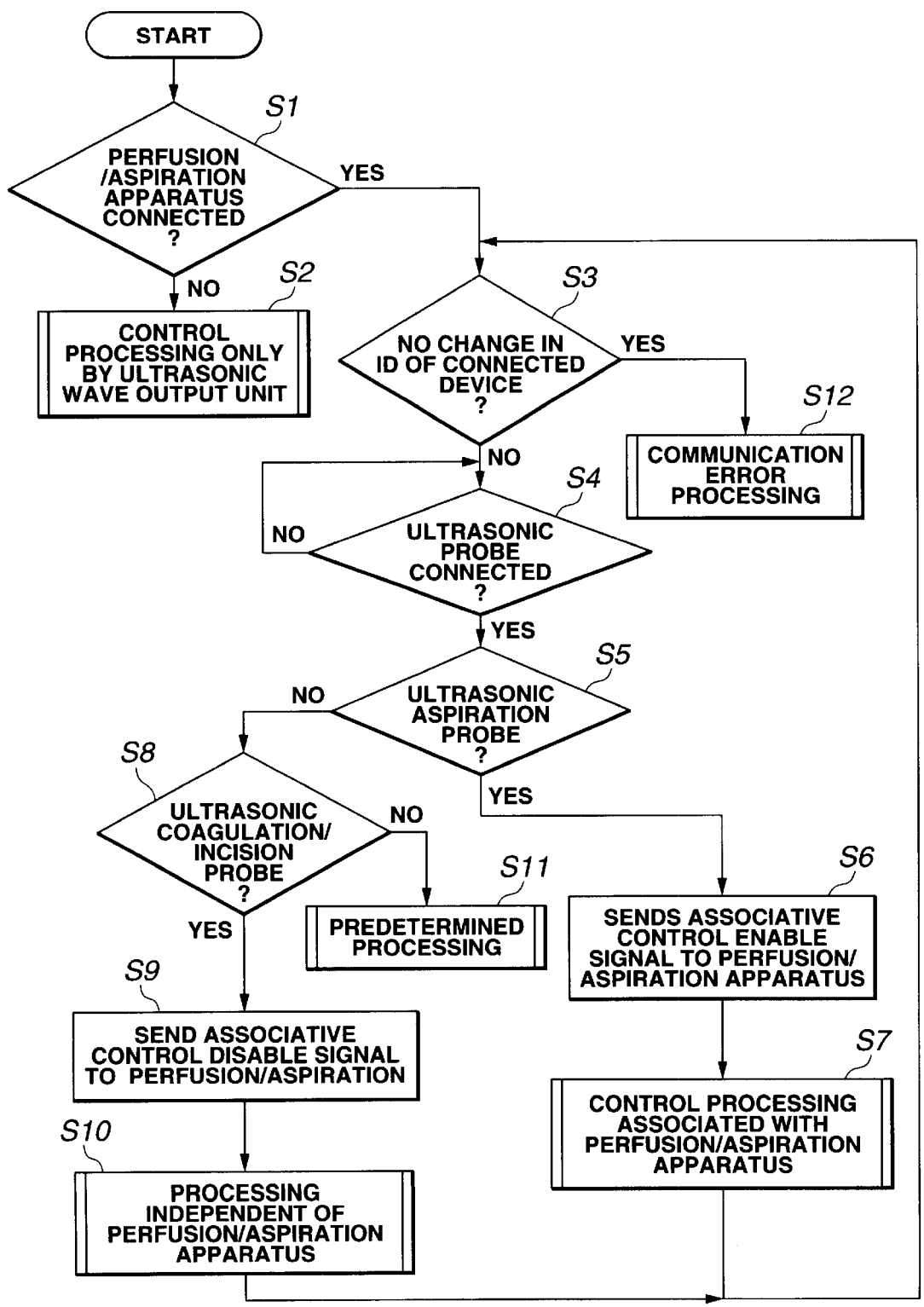

In the ultrasonic wave output apparatus 102, it is determined through communications whether or not the perfusion/aspiration apparatus 103 is connected, as shown at step S1 in FIG. 8. When not connected, the ultrasonic wave output apparatus 102 alone performs a control operation, as shown at step S2.

On the other hand, upon determining that the perfusion/aspiration apparatus 103 is connected, it is determined at step S3 whether or not the ID of the connected apparatus has been changed. Further, at step S4, it is determined by the probe determination unit 116 whether or not an ultrasonic probe is connected to the ultrasonic wave output apparatus 102. Then, connection of an ultrasonic probe is awaited, and when connected, it is determined whether or not the connected ultrasonic probe is the ultrasonic aspiration probe 104, as shown at step S5. If so, an associative control enable signal is sent to the perfusion/aspiration apparatus 103 at step S6, and associative control processing with the perfusion/aspiration apparatus 103 is performed at step S7, followed by the flow returning to step S3.

When the perfusion/aspiration apparatus 103 receives the signal sent thereto at step S6, it is ready to perform the associative control with the ultrasonic wave output apparatus 102.

When it is determined at step S5 that the ultrasonic probe connected to the ultrasonic wave output apparatus 102 is not the ultrasonic aspiration probe 104, but the ultrasonic coagulation/incision probe 105, as shown at step S9, the control unit 112 sends an associative control disable signal to the perfusion/aspiration apparatus 103 as shown at step S9, and disables the perfusion/aspiration apparatus 103 to perform the associative control, forcing the ultrasonic wave output apparatus 102 to operate alone, as shown at step S10, followed by the flow returning to step S3.

When the perfusion/aspiration apparatus 103 receives the signal sent thereto at step S9, it is disabled to perform the associative control with the ultrasonic wave output apparatus 102, and accepts switching operation through the twin foot switch 106 (in this event, the perfusion/aspiration apparatus 103 operates as if the twin foot switch 106 were directly connected to the switch sensing unit 115).

At step S8, when it is also determined that the connected ultrasonic probe is not the ultrasonic coagulation/incision probe 105, predetermined processing is performed as correspondingly set for this case. For example, error processing may be performed when the perfusion/aspiration apparatus 103 only supports the ultrasonic aspiration probe 104 and the ultrasonic coagulation/incision probe 105.

When it is found at step S3 that the ID of the connected apparatus has been changed, communication error processing is performed at step S12.

In this event, the error is displayed only on the display unit of the device (apparatus) in which the error occurred, and the error is not displayed on the remaining apparatus.

This allows the user to readily recognize in which device the error has occurred, thereby improving the operability.

For example, when the ultrasonic wave output apparatus 102 is in error, the ultrasonic wave output apparatus 102 only displays the error on the display unit 117, and stops its operation. In this event, the perfusion unit 124 normally operates when the operator steps on the perfusion pedal 107*a* on the triple foot switch 7 associated with the perfusion/aspiration apparatus 103, while the aspiration unit 123 normally operates when the operator steps on the aspiration pedal 107*b*. Otherwise, when the operator steps on the output pedal 107*c*, ultrasonic waves cannot be output, therefore the operation on the output pedal 107*c* is not accepted. Alternatively, when the operator steps on the output pedal 107*c*, the perfusion/aspiration apparatus 103 also displays an error on the display unit 127 to notify the user of control inability.

Also, for example, when the perfusion/aspiration apparatus 103 is in error, the perfusion/aspiration apparatus 103 only displays the error and stops its operation. In this event, when the operator steps on the setting output pedal 106*a* on the twin foot switch 106, a set ultrasonic wave output is delivered from the ultrasonic wave output unit 113 if the switch sensing unit 125, the control unit 122, and the communication unit 121 do not fail. Further, when the operator steps on the 100% output pedal 106*b*, a control operation similar to the above is performed except for the output value. However, if any of the switch sensing unit 125, the control unit 122 and the communication unit 121 fails, no pedal is not accepted. Further, any of the pedals on the triple foot switch 107 is not accepted.

Specifically, with an ultrasonic probe which involves the associative control (which requires the associative control), i.e., with the type of ultrasonic probe controlled by the triple foot switch 107, no control is performed if the perfusion/aspiration apparatus 103 is in error. With an ultrasonic probe for which the associative control is disabled (not required), i.e., with the type of ultrasonic probe controlled by the twin foot switch 106, the ultrasonic wave output is controlled if the perfusion/aspiration apparatus 103 is in error, while the control is performed to allow the ultrasonic wave output when no error is found.

When the associative control is required, control for output and so on is stopped if any of the ultrasonic wave output apparatus 102 and the perfusion/aspiration apparatus 103 is in error. On the other hand, when the associative control is not required, the control for output and so on is stopped only if the ultrasonic wave output apparatus 102 is in error.

Also, when an error occurs, the error is displayed only on a device in which the error is present, so as to recognize which device has failed or is in error, thereby improving the operability for removing the error.

When the associative control is instructed at step S7, the perfusion/aspiration apparatus 103 accepts only switching operations on the triple foot switch 107, and does not accept information from the twin foot switch 106. In this way, any unintended 100% output can be eliminated (it should be noted that some ultrasonic probes may be extended to accept the twin foot switch 106, in which case identification information is used on to determine whether or not an input through the foot switch can be accepted).

Then, when the operator steps on the perfusion pedal 107*a* on the triple foot switch 107, the perfusion unit 124 performs perfusion for the ultrasonic aspiration probe 104 through the perfusion tube 132.

Also, when the operator steps on the aspiration pedal 107*b*, the aspiration unit 123 aspirates the perfused liquid, blood vessels, tissue, and so on from the ultrasonic aspiration probe 104 through the aspiration tube 131.

When the operator steps on the output pedal 107*c*, this is communicated from the communication unit 121 to the communication unit 111 and the switch sensing unit 115, thereby notifying the communication unit 111 that the operator is stepping on the output pedal 107*c*.

The switch sensing unit 115 is notified of the same information as that which is generated when the operator steps on the setting output pedal 106*a*. This information is sent to the control unit 112 and to the output open/close port, 114, such that the ultrasonic wave output apparatus 102 controls the delivery of a set ultrasonic wave output from the ultrasonic wave output unit 113 to the ultrasonic aspiration probe 104 through the output open/close port 114.

On the other hand, when the associative control is disabled, the perfusion/aspiration apparatus 103 accepts only switching operations through the twin foot switch 106.

Then, as a switching operation is performed through the twin foot switch 106, the perfusion/aspiration apparatus 103 sends a signal indicative of the operation to the switch sensing unit 115 of the ultrasonic wave output apparatus 102 through the switch sensing unit 125 and the control unit 122, and performs a control operation in accordance with the result of sensing at the switch sensing unit 115.

In other words, in this case, similar actions to those produced when the twin foot switch is connected to the switch sensing unit 115 of the ultrasonic wave output apparatus 102 are made without connecting the twin foot switch 106 to the switch sensing unit 125 of the perfusion/aspiration apparatus 103.

Information on a sensed switch by the switch sensing unit 115 is sent to the control unit 112 as well as to the output open/close port 114 through associated hardware to control the output open/close port 114 to open or close the output based on the information.

For example, an ultrasonic driving signal is output from an output line when the switch is ON, while the output line is closed to prevent the ultrasonic driving signal from being output when the switch is OFF.

The control operation for opening/closing the output with the information on a sensed switch, together with the control operation performed by the control unit 112, prohibits unintended output due to a failure in an apparatus, thereby making it possible to more reliably prevent malfunctions.

When the operator steps on the setting output pedal 106a on the twin foot switch 106 to turn ON the same, an ultrasonic wave output at a set value is output from the ultrasonic wave output unit 113. When the operator steps on the 100% output pedal 106b to turn ON, a 100% ultrasonic wave output is output from the ultrasonic wave output unit 113 irrespective of the set value.

As described above, the third embodiment identifies whether or not an ultrasonic probe connected to the ultrasonic wave output apparatus 102 is an ultrasonic probe which requires the association with the function of the perfusion/aspiration apparatus 103, and associates the function of the perfusion/aspiration apparatus 103 with the ultrasonic wave output apparatus 102 when the identification indicates the connection of such an ultrasonic probe that requires the association with the function of the perfusion/aspiration apparatus 103, while it disables the association when an ultrasonic probe which does not require the association is connected, thereby making it possible to realize a highly usable ultrasonic operation system which can perform an ultrasonic operation with or without the associative control depending on the ultrasonic probe connected to the ultrasonic wave output apparatus 102.

It should be noted that when the ultrasonic coagulation/incision probe 105 is connected to the ultrasonic wave output apparatus 102 without the connection with the perfusion/aspiration apparatus 103 through the communication cable 108 to use the ultrasonic wave output apparatus 102 and the ultrasonic coagulation/incision probe 105 as a stand-alone ultrasonic coagulation/incision operation apparatus without a perfusion/aspiration function, the twin foot switch 106 may be connected to the switch sensing unit 115 and used with the ultrasonic coagulation/incision operation apparatus.

In this configuration, the switch sensing unit 115 senses whether the twin foot switch 106 is turned ON/OFF to transmit the result of the sensing to the control unit 112. In response, the ultrasonic wave output unit 113 outputs an ultrasonic driving signal for ultrasonic driving the ultrasonically coagulation/incision probe 105 to ultrasonic vibrate an ultrasonically vibrator, not shown, within the ultrasonic coagulation/incision probe 105 to allow for ultrasonic coagulation and incision treatments.

When the perfusion/aspiration apparatus 103 is not connected to the ultrasonic wave output apparatus 102 through the communication cable 108, the perfusion/aspiration apparatus 103 may be used alone.

When the perfusion/aspiration apparatus 103 is not connected to the ultrasonic wave output apparatus 102 through the communication cable 108, the ultrasonic aspiration probe 104 may be connected to the ultrasonic wave output apparatus 102, and the aspiration tube 131 and the perfusion tube 132 of the ultrasonic aspiration probe 104 are connected to the perfusion/aspiration apparatus 103, such that the ultrasonic wave output apparatus 102 and the perfusion/aspiration apparatus 103 can be used independently of each other.

Figure 9:
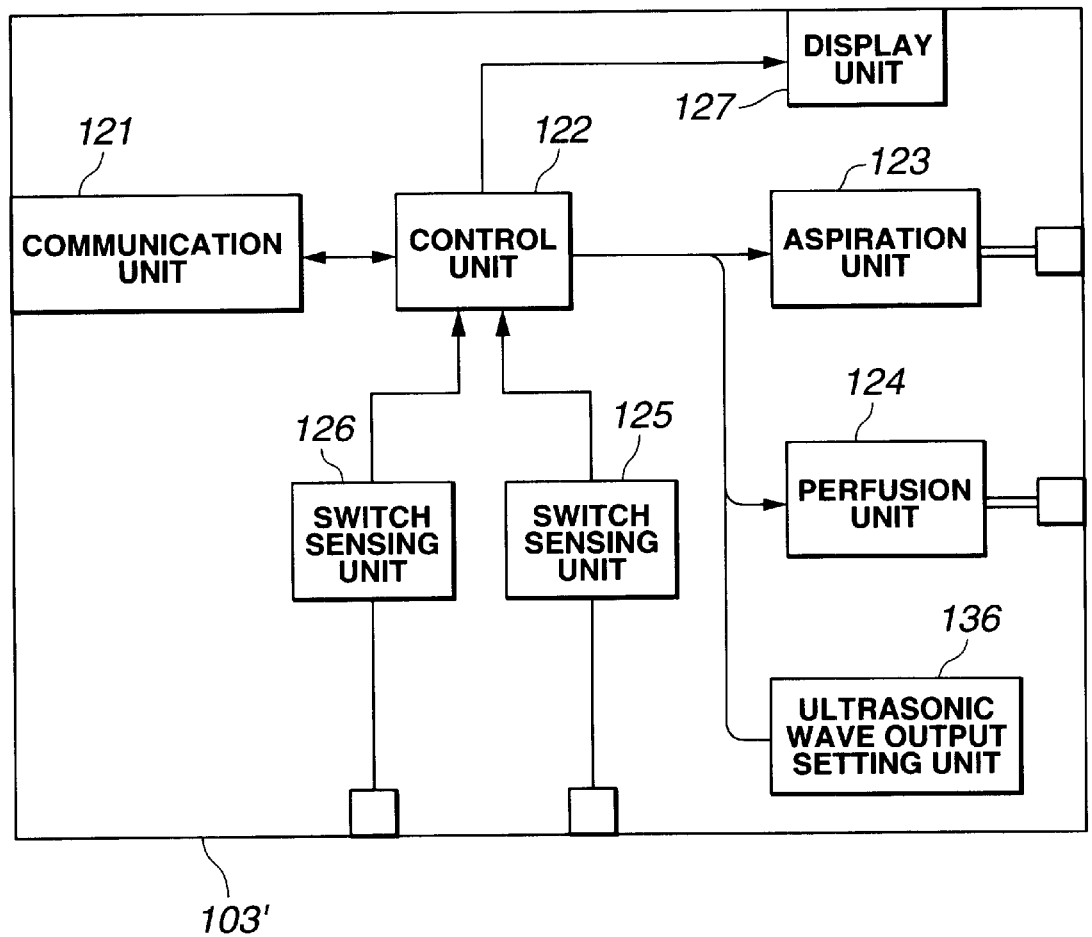

While in the configuration of FIG. 7, the ultrasonic wave output can be set at the ultrasonic wave output apparatus 102, an ultrasonic wave output setting unit 136 may be provided such that an ultrasonic wave output can be set at the triple foot switch 107, as a perfusion/aspiration apparatus 103' in a modification illustrated in FIG. 9.

In this configuration, the communication with the switch sensing unit 115 associated with the ultrasonic wave output apparatus 102 only serves to make the switch sensing unit 115 recognize whether or not the foot switch is turned ON and to control the output open/close port 114.

Information on setting of the ultrasonic wave output is always transmitted through the communication unit 121 and the communication unit 111. Each time the operator steps on the output pedal 107c on the triple foot switch 107, the communication unit 121 transmits information on the output setting and information indicating that the operator is stepping on the output pedal 107c.

However, since the output setting information and the foot switch ON information partially overlap each other, only the output setting information may be communicated for high speed communication.

In this event, data may be subjected to error sensing such as check sum in order to prevent any unintended output, thereby enhancing the malfunction preventing capability.

As described above, the third embodiment has the following advantages.

The use of the ultrasonic wave output apparatus 102 and the perfusion/aspiration apparatus 103 in combination allows for extension of the system, and utilization of a plurality of inexpensive ultrasonic probes.

Since the type of ultrasonic wave probe is used to automatically enable or disable the associative control with the perfusion/aspiration apparatus 103, the ultrasonic operation apparatus of the third embodiment is simple for the user to operate, and provides high operability (usability).

When a plurality of devices are used simultaneously, an erroneous device can be readily identified.

Even if a device fails, intended functions can be implemented as long as minimally required devices and functions are normal. Also, since the devices and functions are automatically controlled, the user experiences good operability.

(Fourth Embodiment)

Next, referring to FIG. 10 a description will be given on an ultrasonic operation system according to a fourth embodiment which can perform an ultrasonic operation with the ultrasonic aspiration probe 104, the ultrasonic coagulation/incision probe 105, and etc. previously shown in the third embodiment, connected simultaneously to the system.

Figure 10:
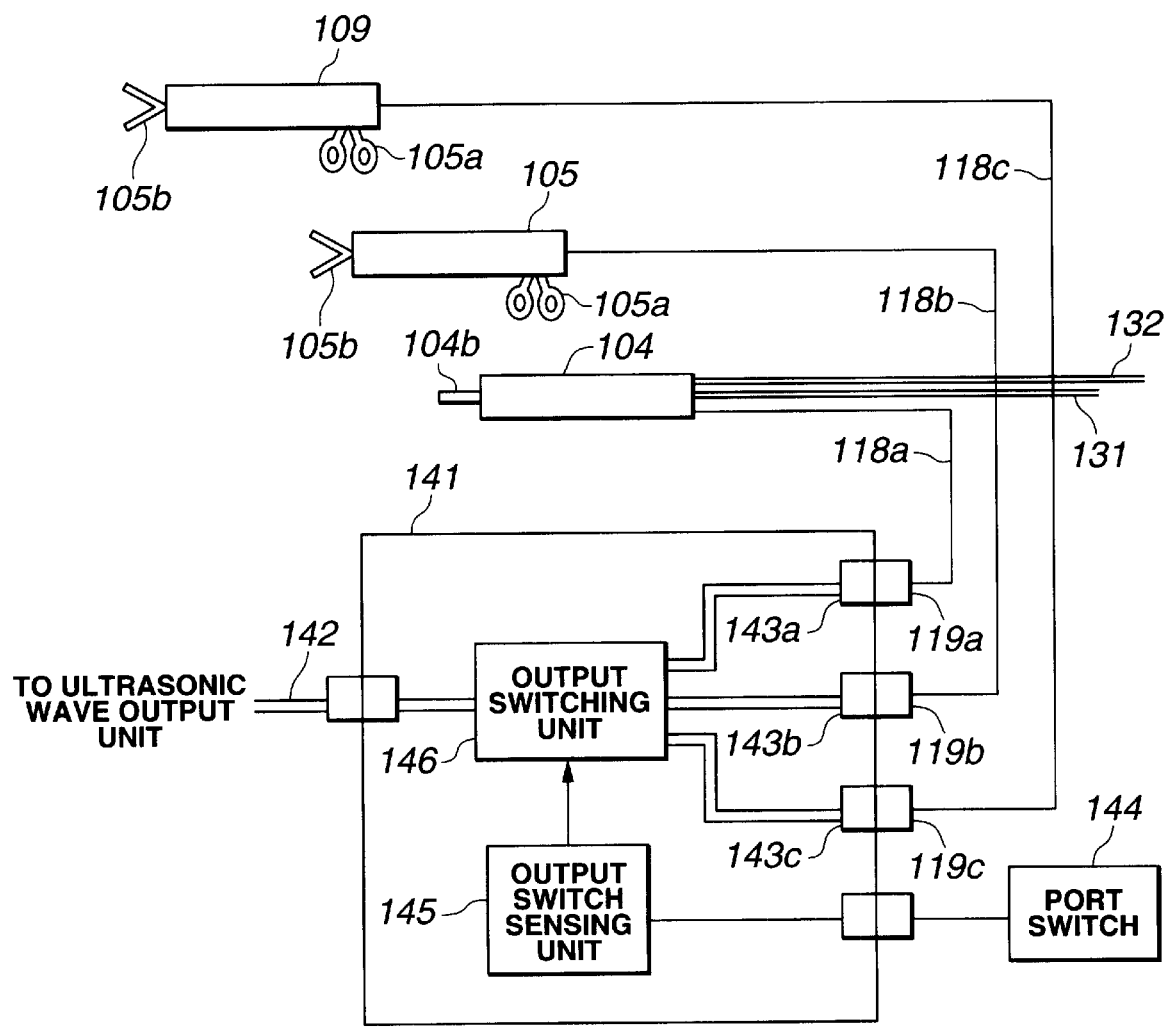
FIG. 10 is a block diagram illustrating the configuration of an output switching apparatus in a fourth embodiment of the present invention.

FIG. 10 illustrates the configuration of a main portion in the fourth embodiment, wherein a single ultrasonic wave output can be supplied through one port selected from three ports.

In the fourth embodiment, an output switching apparatus 141 shown in FIG. 10 is connected to the ultrasonic wave output apparatus 102 in the third embodiment of FIG. 7 through a connection cable 142 (note that the perfusion/aspiration apparatus 103' in FIG. 9 is used in this embodiment). Ports 143a, 143b, 143c of the output switching apparatus 141 are connected to connectors 119a, 119b, 119c at respective rear ends of respective ultrasonic driving output cables 118a, 118b, 118c for connection with an ultrasonic aspiration probe 104, a (first) ultrasonic coagulation/incision probe 105, and a second ultrasonic coagulation/incision probe 109 which is different for example in power from the first ultrasonic coagulation/incision probe 105, respectively.

The output switching apparatus 141 is also connected to a port switch 144 for selectively switching the ports to which the operated ultrasonic probes are connected.

Then, as the port switch 144 is manipulated to switch one port to another, an output switch sensing unit 145 in the output switching apparatus 141 determines which port 143j (j=a, b, c) has been selected by the manipulation on the port switch 144. The output switch sensing unit 145 switches an output switching unit 146 in the output switching apparatus 141 in response to information on the determination, and selects aport 143j which is actually supplied with an ultrasonic driving output from the output switching unit 146 through the connection cable 142.

Also, in the fourth embodiment, each port 143j is connected to a detecting line for detecting an identifying resistor of a connector 119j, in addition to a line for supplying the ultrasonic driving output to the ultrasonic probe. Then, when an arbitrary port 143k (k is an arbitrary one of a, b, c) (with which an ultrasonic treatment is actually performed) is selected from the three port 143a, 143b, 143c by the port switch 144, the output switch sensing unit 145 sets the line to supply the ultrasonic driving output to the port 143k, and also connects the detecting line connected to the port 143k to the probe identification unit 116 through the connection cable 142 to detect the identifying resistor of the connector 119k connected to the port 143k.

For this purpose, the connection cable 142 also includes a detecting line in addition to the line for supplying the ultrasonic driving output.

Thus, in the fourth embodiment, when the port 143a, for example, is selected by the port switch 144 to select the ultrasonic aspiration probe 104 connected thereto, the probe identification unit 116 senses the selection of the ultrasonic aspiration probe 104 through the identifying resistor in the connector 119a, and sends the sensing result to the control unit 112 which in turn sends an associative control enable signal to the control unit 122 of the perfusion/aspiration apparatus 103 to allow for the execution of the associative control.

On the other hand, when the port 143b or 143c, for example, is selected by the port switch 144 to select the ultrasonic coagulation/incision probe 105 or 109 connected thereto, the probe identification unit 116 senses the selection of the ultrasonic coagulation/incision probe 105 or 109 through the identifying resistor in the connector 119b or 119c, and sends the sensing result to the control unit 112 which in turn sends an associative control disable signal to the control unit 122 of the perfusion/aspiration apparatus 103 to perform a control operation in an environment in which the associative control is disabled.

Next, the operation of the fourth embodiment will be described.

Generally, the ultrasonic aspiration probe is used at a low output of approximately 30%.

The ultrasonic coagulation/incision probe, on the other hand, is set at 70% when coagulation is accounted for, and set at 100% when incision is accounted for.

The setting can also be made at an ultrasonic wave output setting unit 136 in the perfusion/aspiration apparatus 103' in a modification to the fourth embodiment, so that the ultrasonic wave output setting unit 136 sets the output at 30%, while a setting unit, not shown, in the ultrasonic wave output apparatus 102 sets the output at 70%.

In this way, when the ultrasonic aspiration probe 104 is used, the operator may step on the output pedal 107c on the triple foot switch 107 to perform the ultrasonic wave output, perfusion, and aspiration as set at the ultrasonic wave output setting unit 136.

On the other hand, when the ultrasonic coagulation/incision probe 105 or 109 is used, the operator may step on the setting output pedal 106a or the 100% output pedal 106b on the twin foot switch 106, so that a 70% or 100% output can be provided as set on (the setting unit of) the ultrasonic wave output apparatus 102.

In the manner described above, it is possible to simultaneously use, through simple operations, those probes that individually require different output settings such as the ultrasonic aspiration probe 104 and the ultrasonic coagulation/incision probes 105, 109.

Other than the foregoing, the fourth embodiment has similar advantages to those of the third embodiment.

In ultrasonic operation treatments, some probes can accommodate an electric knife treatment. For example, see Japanese Patent Laid-Open No. Hei 9-38098. However, simultaneous generation of an ultrasonic wave output and an electric knife output results in a high attack rate, such that when the electric knife output is being generated, the ultrasonic wave output is typically stopped. This function of stopping the ultrasonic wave output when the electric knife output is sensed may be utilized, for example the sensing information is sent, to the perfusion/aspiration apparatus 103 in FIG. 7 to additionally stop the perfusion and aspiration operations. In this configuration, however, it is assumed that the ultrasonic wave output apparatus 102 in FIG. 7 is also equipped with a function of generating an electric knife output.

On the other hand, with a probe having an ultrasonic aspiration function, the associative control is enabled, and with a probe having an ultrasonic coagulation incision function, the associative control is disabled.

In this way, in the ultrasonic wave output apparatus 102, as an electronic knife output is generated by a probe, electric knife sensing information is transmitted additionally to the perfusion/aspiration apparatus 103 to stop the perfusion and aspiration operations as well.

Thus, the modification to the fourth embodiment is also applicable to a probe having an electronic knife function.

(Fifth Embodiment)

Next, a fifth embodiment of the present invention will be described with reference to FIGS. 11 through 19. An electric treatment system 151 according to the fifth embodiment illustrated in FIG. 11 is an equipped with an endoscope apparatus 152.

An endoscope 153 having a built-in imager device is connected to a light source 154 for generating illumination light, and an image processing unit 155 for processing images captured by the imager device. A monitor 156 connected to the image processing unit 155 displays an image captured by the endoscope 153.

The electric treatment system 151 also comprises an electric knife apparatus 161 as a medical instrument, to which a hand piece 157 for treatment or the like is connected; an ultrasonic wave output apparatus 162 and a perfusion/aspiration apparatus 163; a pneumoperitoneum apparatus 164 connected to a trocar 159 for performing pneumoperitoneum and so on. The image processing unit 155, light source 154, electric knife apparatus 161, ultrasonic wave output apparatus 162, perfusion/aspiration apparatus 163 and pneumoperitoneum apparatus 164 are connected through a communication cable 166 for communicating with a controller 165.

Figure 11:
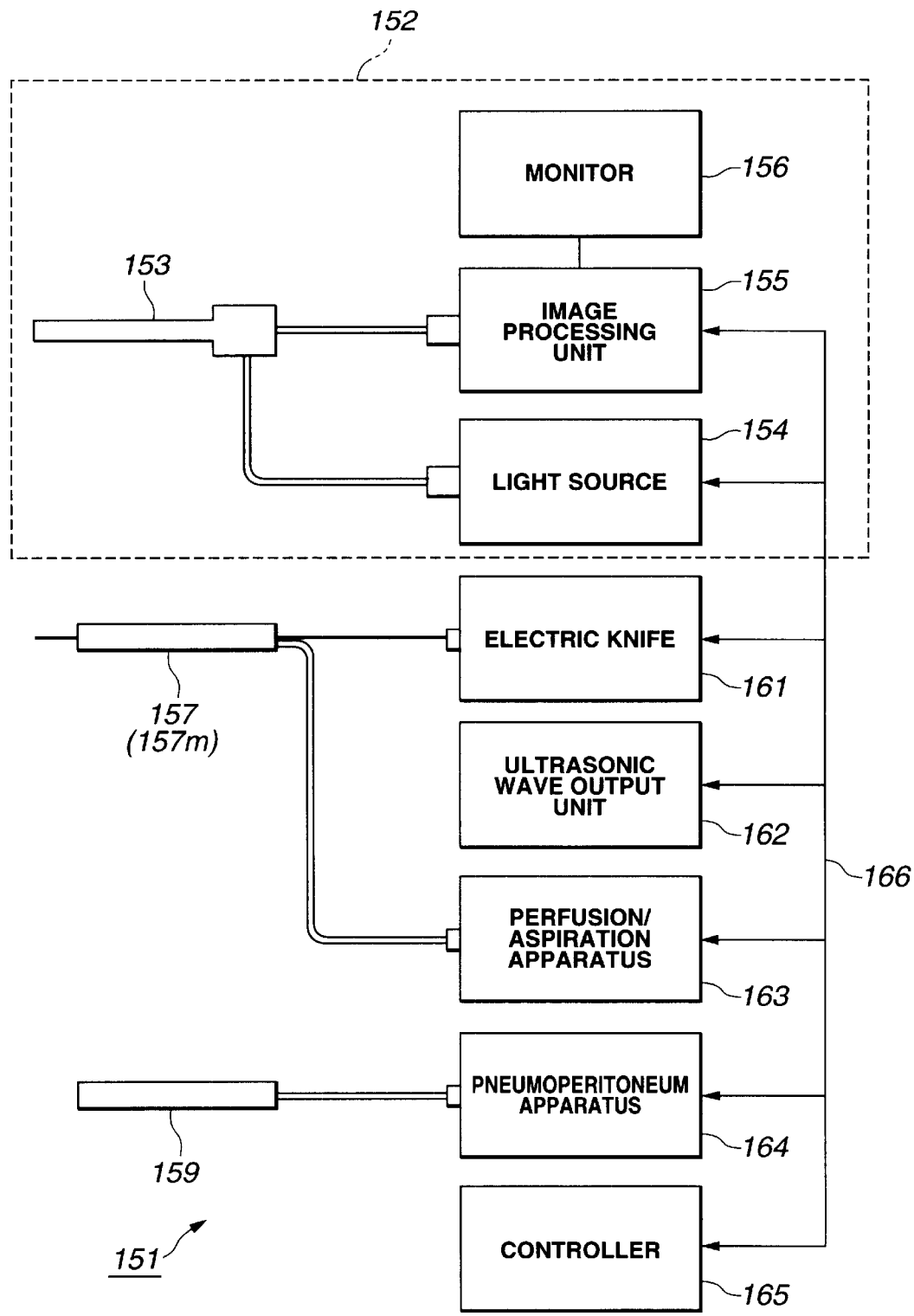

In FIG. 11, the treatment hand piece 157 is shown as an electric knife hand piece 157m (where m indicates a–d in FIG. 16, i.e., m=a–d) by way of example. While the electric knife hand piece 157m is connected to the electronic knife apparatus 161 and to the perfusion/aspiration apparatus 163, an ultrasonic treatment hand piece 157n (n=e–h) shown in FIG. 17 is connected to the ultrasonic wave output apparatus 162.

When the electric knife hand piece 157m is connected to the electric knife apparatus 161, the type of the connected hand piece 157m is discriminated, as described in connection with FIG. 12. The result of the discrimination is sent to the controller 165 through the communication cable 166, turn the controller 165 sends a control signal for instructing a single device to operate alone or for instructing a plurality of devices to operate in association, in accordance with the discrimination result.

For example, if the discriminated hand piece 157m is the type of a hand piece which involves an associative operation of a plurality of devices, the controller 165 sends the control signal to the plurality of devices involved in the associative operation through the communication cable 166, thus bringing these devices into an associative operation enabled state.

In the configuration of FIG. 11, the controller 165 sends the control signal (instructing the associative operation), for example, to the electric knife apparatus 161 and the perfusion/aspiration apparatus 163, causing these components to operate in association.

Figure 12:
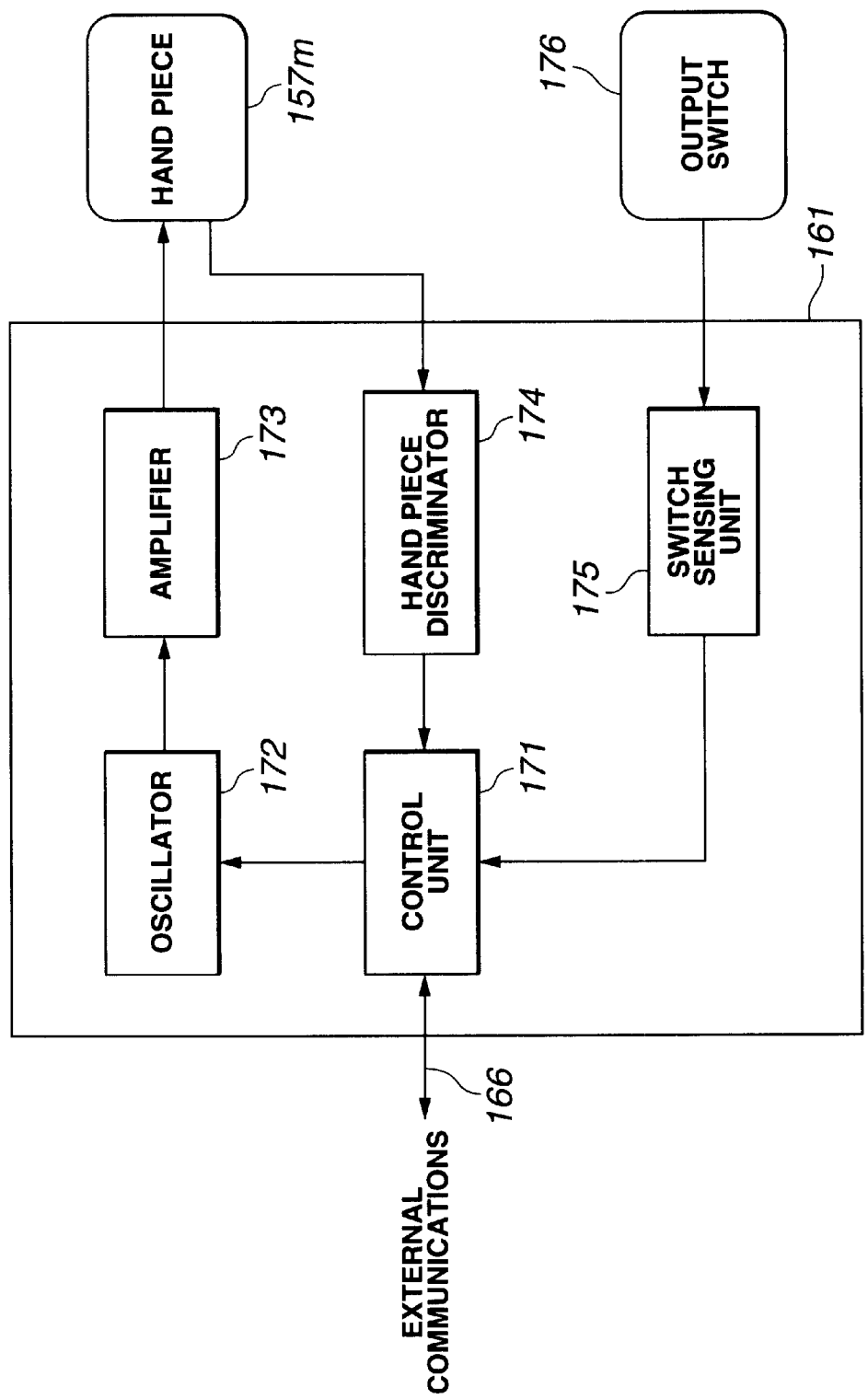

Then, (as an output switch 176 in FIG. 12 is turned ON,) an output from the electric knife apparatus 161 is supplied to the hand piece 157m with which a tissue of interest can be subjected to such treatment as incision, coagulation or the like.

Figure 16:
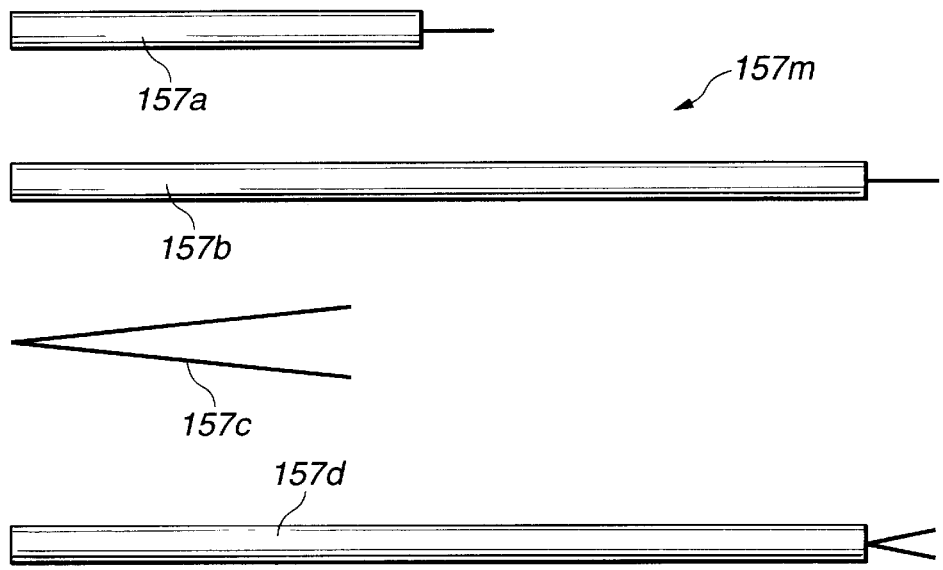
Figure 17:
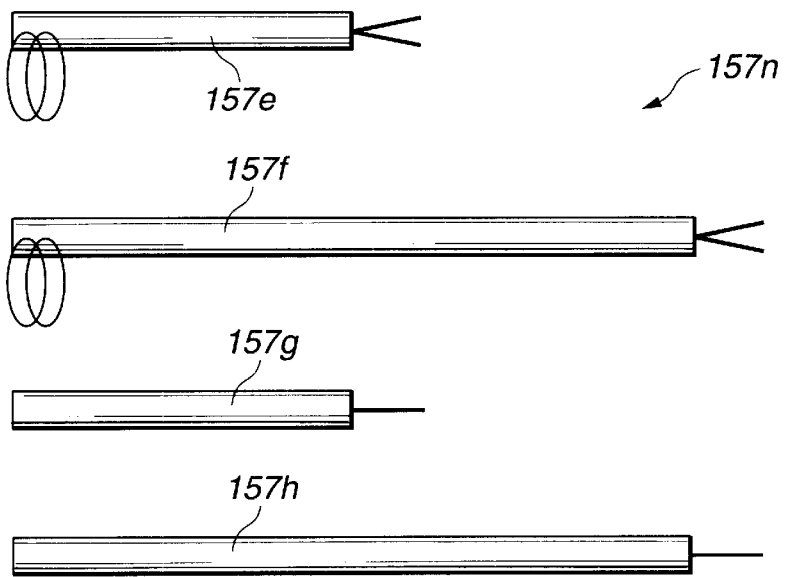

On the other hand, when the hand piece 157m is a hand piece 157c in FIG. 16, perfusion from the perfusion/aspiration apparatus 163 is supplied to the hand piece 157c with which a tissue is washed or cooled. In addition, liquids within an abdominal pore are aspirated by the hand piece 157c.

The trocar 159 is connected to the pneumoperitoneum apparatus to maintain the abdominal pore pressure constant and to remove from the abdominal pore the smoke that may be produced due to an output from the electric knife apparatus 161 or an output from the ultrasonic wave output apparatus 162.

The controller 165 is connected to the respective components through the communication cable 166, through which control signals and so on are transmitted and received between them, to know the states of the respective components and allow for controlling the respective components.

In this way, during a treatment using a device to which a hand piece 157m is connected, it is possible to operate and set only a single or a plurality of devices required for the treatment for a curative procedure.

While the controller 165 concentrically controls all the components in the fifth embodiment, the respective components may be communicated with one another to perform distributive control, in which case similar actions and advantages can be provided.

FIG. 12 illustrates the structure of the electric knife apparatus 161 for use in the fifth embodiment. While the electronic knife apparatus 161 also includes other necessary components, FIG. 12 preponderantly illustrates only the characteristic features for achieving the object, and other necessary components are omitted from the drawing. The output of the electric knife apparatus 161 is controlled by turning ON/OFF the output switch 176, and the ON/OFF state of the output switch 176 is detected by the switch sensing unit 175.

A signal indicative of the sensed ON/OFF state is input to the control unit 171 which controls the oscillator 172 to generate a signal having a waveform for the electric knife output. The output signal is amplified by the amplifier 173 to generate a high frequency, large power electric knife output signal which is supplied to a tissue subjected to a treatment for a curative procedure through the hand piece 157m. The output switch 176 is generally comprised of two switches, i.e., an incision switch and a coagulation switch.

When the hand piece 157m is connected to the electric knife apparatus 161, the hand piece discriminator 174 discriminates what type of hand piece is connected, and inputs the result of the discrimination to the control unit 171. The control unit 171 sends the discrimination result to the controller 165 through the communication cable 166. The controller 165 sends a control signal for controlling devices to be operated, and controls the setting of operating parameters in accordance with the discrimination result.

Figure 18:
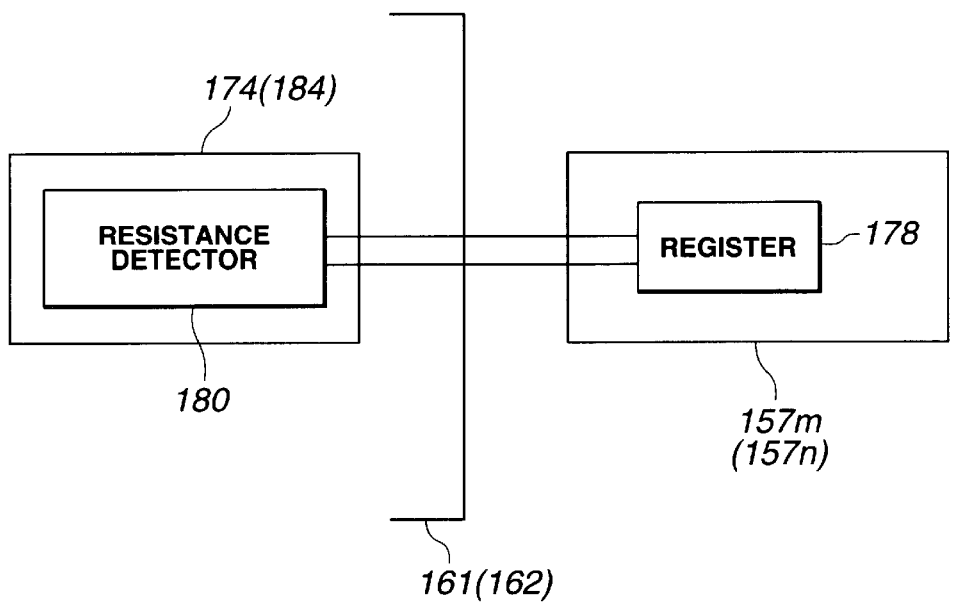

For discriminating the type of the hand piece 157m, an identifying resistor 178 is provided in each of the hand pieces 157m, as illustrated in FIG. 18, such that a resistance detector (resistance range detector) 180, which is forming part of the hand piece discriminator 174 and in disposed in the electric knife apparatus 161, detects the resistance of the resistor 178. Alternatively, the type of the hand piece 157m can be discriminated from a resistance range to which the resistance belongs. Further, alternatively, a small current may be applied to detect a voltage across the connected resistor 178 to detect the resistance thereof.

Figure 13:
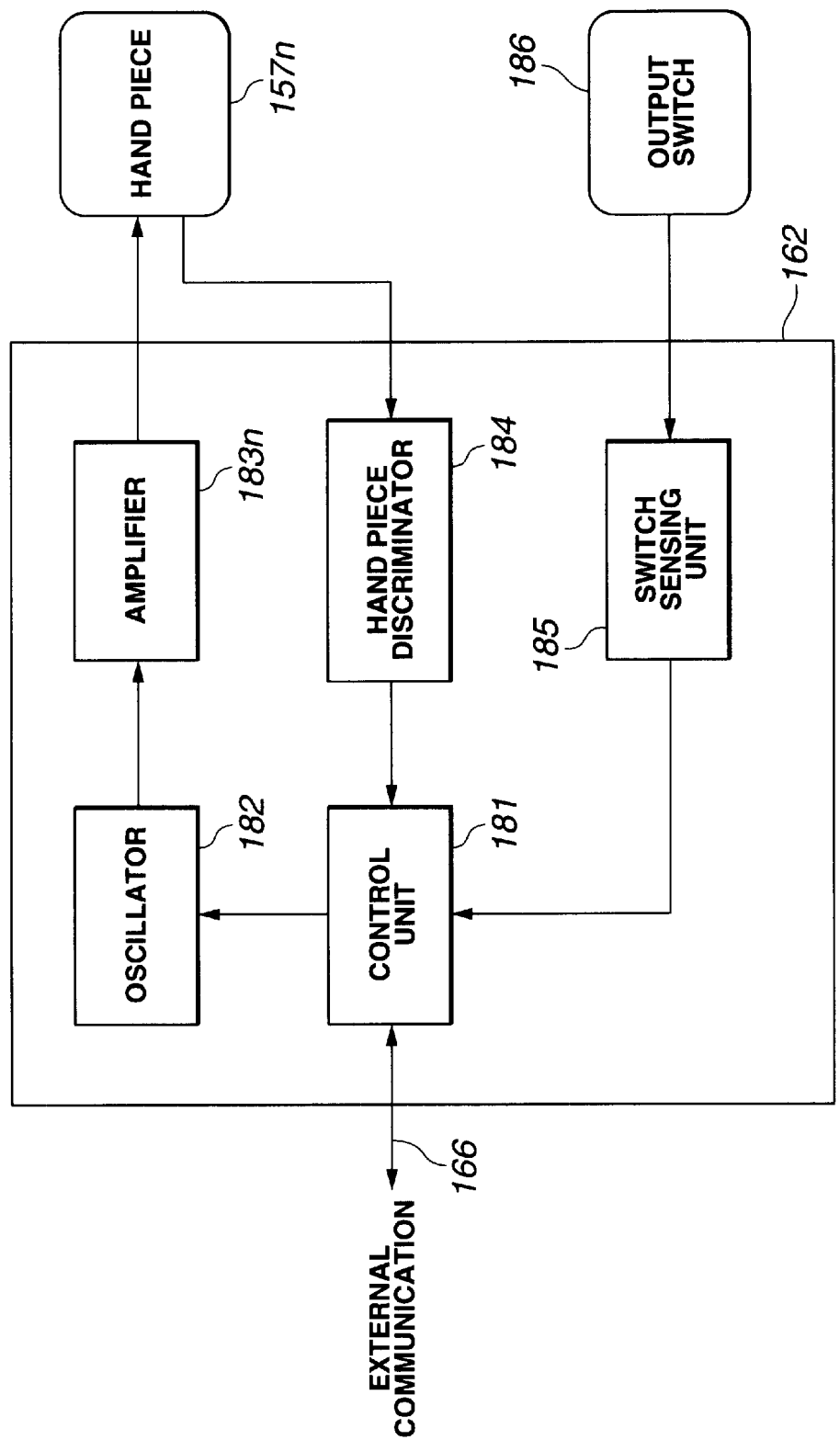

FIG. 13 illustrates the configuration of the ultrasonic wave output apparatus 162 for use with the fifth embodiment.

While the ultrasonic wave output apparatus 162 includes other necessary components, FIG. 13 preponderantly illustrates only the characteristic features for achieving the object, and other necessary components are omitted from the drawing.

The output of the ultrasonic wave output apparatus 162 is controlled by turning ON/OFF an output switch 186, the state of which is detected by the switch sensing unit 185. A signal indicative of the sensed ON/OFF state is input to the control unit 181 which controls the oscillator 182 to generate a signal having a waveform for the ultrasonic wave output.

The output signal is amplified by the amplifier 183 to generate a high frequency, large power ultrasonic output signal which is supplied to a hand piece 157n. The electric energy of the signal is transduced into kinematic energy (ultrasonic vibration energy) by an ultrasonic vibrator additionally provided in the hand piece 157n, so that a tissue of interest is applied with ultrasonic vibrations.

The output switch 186 is generally comprised of two switches, i.e., a setting switch and a full output switch. The setting switch supplies the hand piece 157n with an ultrasonic output corresponding to a set output, while the full output switch supplies the hand piece 157n with a full output irrespective of the set output.

When the hand piece 157n is connected to the ultrasonic wave output apparatus 162, the hand piece discriminator 184 discriminates what type of hand piece is connected, and inputs the result of the discrimination to the control unit 181.

The control unit 181 sends the discrimination result to the controller 165 through the communication cable 166. The controller 165 sends a control signal for controlling devices to be operated and controls the setting of operating parameter in accordance with the discrimination result.

For discriminating the type of the hand piece 157n, an identifying resistor 178 is provided in the hand piece 157n, as illustrated in FIG. 18, so that the resistance of the identifying resistor 178 may be detected to discriminate the type of the hand piece 157n.

Figure 14:
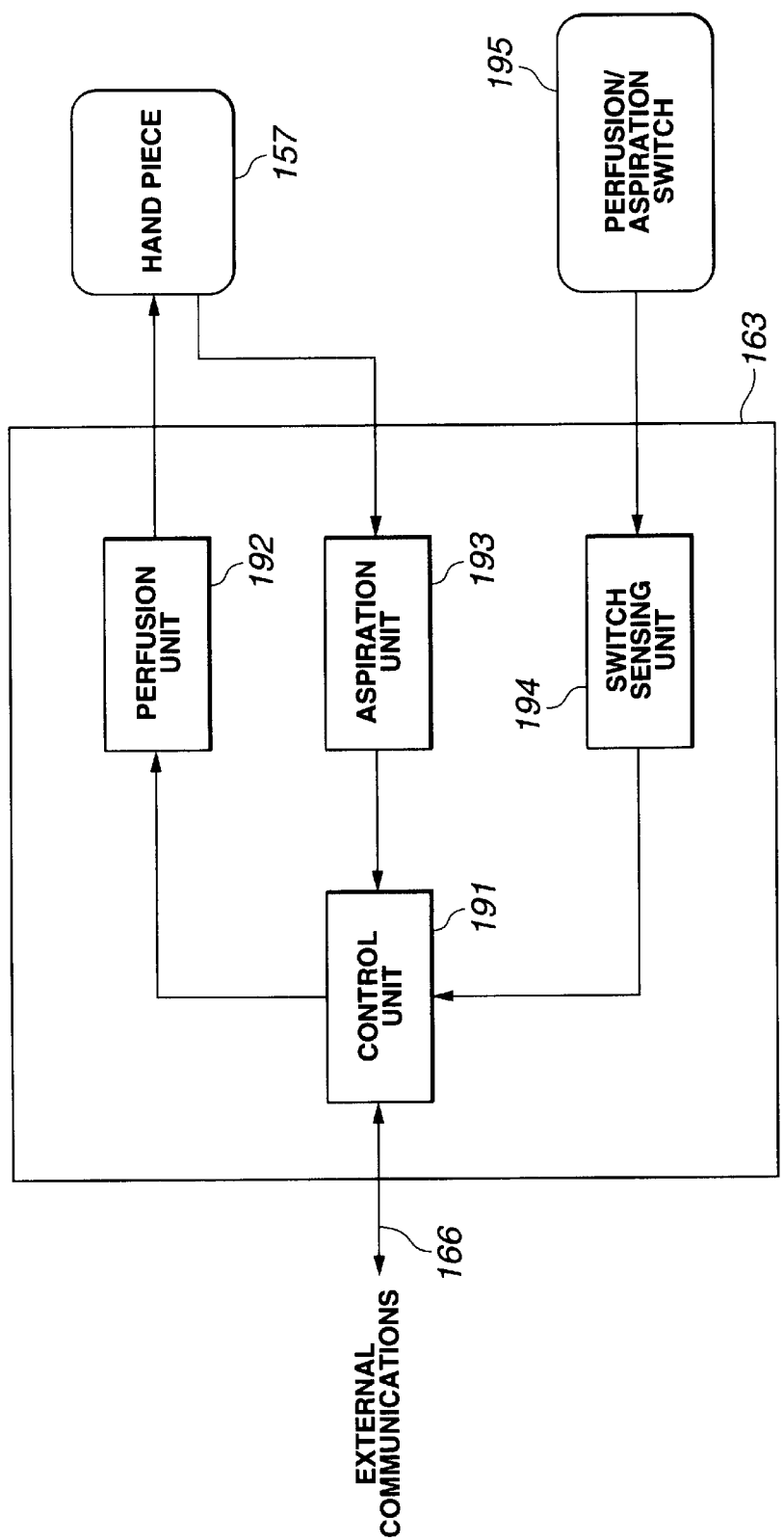

FIG. 14 illustrates the configuration of the perfusion/aspiration apparatus 163.

While the perfusion/aspiration apparatus 163 also includes other necessary components, FIG. 14 preponderantly illustrates only the characteristic features for achieving the object, and other necessary components are omitted from the drawing. The perfusion and aspiration operations of the perfusion/aspiration apparatus 163 are controlled by turning ON/OFF a perfusion/aspiration switch 195, the state of which is sensed by a switch sensing unit 194.

A signal indicative of the sensed ON/OFF state is input to the control unit 191 which instructs the perfusion unit 192 to perform perfusion to the hand piece 157, and controls the aspiration unit 193 to aspirate from the hand piece 157 to the aspiration unit 193.

The control unit 191 is also supplied with a control signal from the controller 165 through the communication cable 166 to determine whether or not the perfusion/aspiration apparatus 163 is instructed to perform the perfusion and/or aspiration operations.

For example, as the control unit 191 receives a control signal for enabling an associative operation, the perfusion and/or aspiration are performed by turning ON/OFF the perfusion/aspiration switch 195 to. On the contrary, as the control unit 191 is receives a control signal for disabling the associative operation, the perfusion and/or aspiration are not performed even if the perfusion/aspiration switch 195 is turned ON/OFF.

The control unit 191 may also be applied with a setting signal for defining operating parameters together with the control signal for enabling an associative operation, in which case the control unit 191 controls the perfusion unit 192 and the aspiration unit 193 in accordance with the setting signal.

The perfusion section 192 supplies the hand piece 157 with the perfusion amount in accordance with the set perfusion amount, while the aspiration unit 193 aspirates from the hand piece 157 at an aspiration pressure in accordance with a set aspiration pressure.

Figure 15:
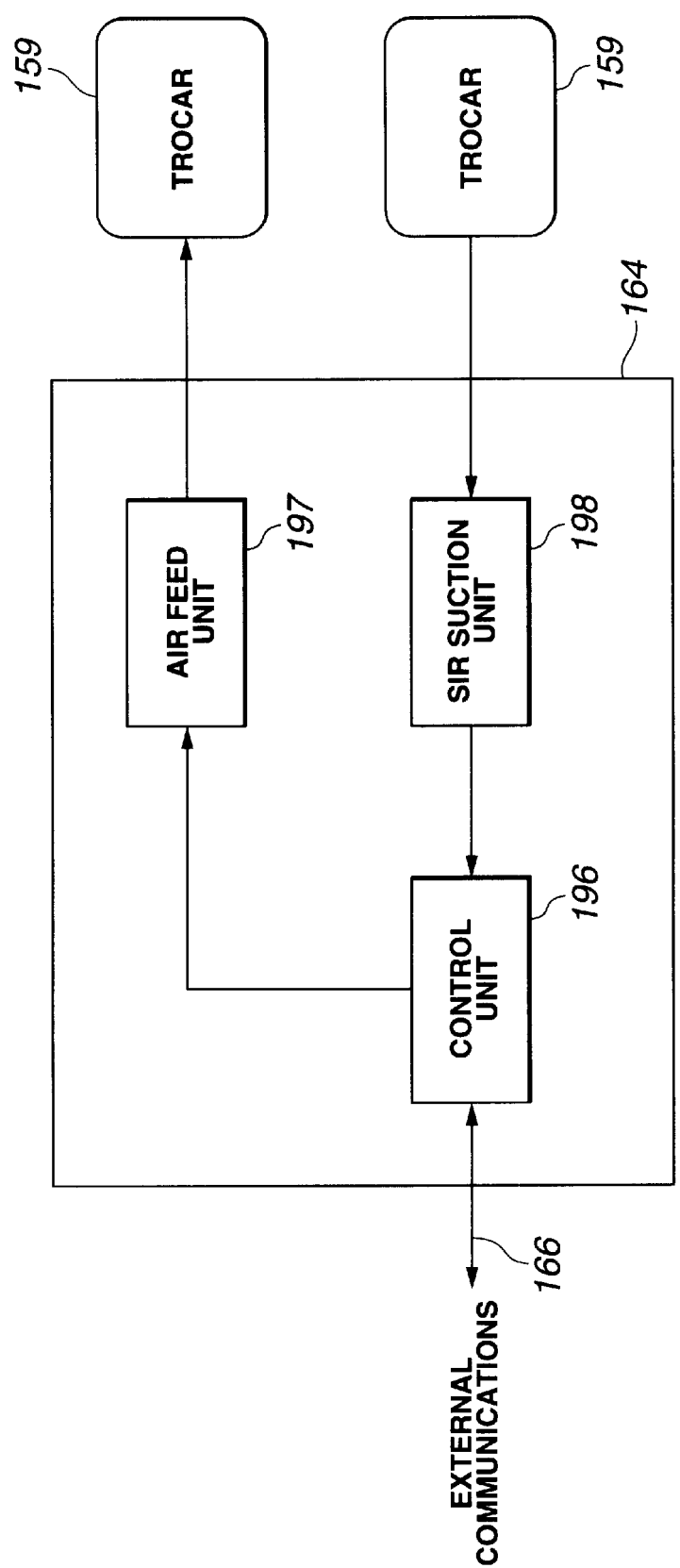

FIG. 15 illustrates the configuration of a pneumoperitoneum apparatus 164.

While the pneumoperitoneum apparatus 164 also includes other necessary components, FIG. 15 preponderantly illustrates only its characteristic features for achieving the object, and other necessary components are omitted from the drawing. A control unit 196 is connected to an external controller 165 through a communication cable 166, and is applied with a control signal for determining whether or not an associative operation is enabled or disabled. Also, as the control unit 196 is applied with a setting signal for determining operating parameters, the control unit 196 controls an air feed operation of an air feed unit 197 and an air suction operation of an air suction unit 198.

The air feed unit 197 is connected to a trocar 159, and feeds air under the control of the control unit 196. The air suction unit 198 is connected to another trocar 159, and sucks air under the control of the control unit 196. The air feed operation is performed mainly to control the abdominal pore pressure to a set value, while the air suction operation is performed for removing smoke generated by the output of the electric knife apparatus or the ultrasonic wave output apparatus 162.

The fifth embodiment is characterized by detecting the type of the hand piece 157 to control the operation of devices required for the hand piece 157. The following description will be given of types of representative hand pieces available for this configuration.

FIG. 16 illustrates several types of hand pieces 157m, all of which are for use with an electric knife apparatus.

An open monopolar hand piece 157a illustrated in FIG. 16 is a hand piece which is used both for incision and for coagulation. When this hand piece 157a is used, the electric knife apparatus 161 is only required to operate, so that other devices are controlled to enter in standby state. Preferably, as the hand piece 157a is connected, only the output of the electric knife apparatus 161 is automatically set. The set value is desirably equal to the same set value which was used by the same hand piece at the preceding time.

A monopolar hand piece 157b for the endoscope illustrated in FIG. 16 is a hand piece which is used both for incision and for coagulation. When this hand piece 157b is used, the electric knife apparatus 161 and the pneumoperitoneum apparatus 164 operate in association (the pneumoperitoneum apparatus 164 feeds air and sucks air in synchronism with the output of the electric knife apparatus 161), to discharge smoke generated by the output of the electric knife apparatus 161 from the abdominal pore.

Like the hand piece 157a, when the hand piece 157b is connected, the connection of the hand piece 157b is recognized to control the exclusive operation of the electric knife apparatus 161 and the pneumoperitoneum apparatus 164 to in association, and to automatically set associated operating parameters. In this case, the electric knife apparatus 161 functions as a main medical instrument for the hand piece 157b, while the pneumoperitoneum apparatus 164 functions as an ancillary medical instrument.

An open bipolar hand piece 157c illustrated in FIG. 16 is a hand piece which is used for coagulation. When this hand piece 157c is used, the electric knife apparatus 161 and the perfusion/aspiration apparatus 163 operate in association (the perfusion/aspiration apparatus 163 performs perfusion in synchronism with the output of the electronic knife apparatus 161) to perform perfusion to the distal end of the bipolar electrode to prevent a tissue of interest from being carbonized and consequently attached to the electrode.

When the hand piece 157c is connected, the electric knife apparatus 161 and the perfusion/aspiration apparatus 163 are controlled to exclusively operate in association, and to automatically set associated operating parameters. In this case, the perfusion/aspiration apparatus 163 functions as an ancillary medical instrument as is the case of the pneumoperitoneum apparatus 164.

An endoscope bipolar hand piece 157d illustrated in FIG. 16 is a hand piece which is used for coagulation. When this hand piece 157d is used, the electric knife apparatus 161, the perfusion/aspiration apparatus 163 and the pneumoperitoneum apparatus 164 operate in association (the perfusion/aspiration apparatus 163 performs perfusion, and the pneumoperitoneum apparatus 164 feeds and sucks air in synchronism with the output of the electric knife apparatus 161) to discharge smoke generated by the output of the electric knife apparatus 161 from the abdominal pore.

When the hand piece 157d is connected, the electric knife apparatus 161, the perfusion/aspiration apparatus 163 and the pneumoperitoneum apparatus 164 are controlled to exclusively operate in association, and operating parameters are automatically set.

FIG. 17 illustrates several hand pieces 157n, all of which are for use with the ultrasonic wave output apparatus.

An open scissors hand piece 157e illustrated in FIG. 17 is a hand piece with which a tissue of interest is clamped at the distal end thereof for performing coagulation and/or incision. When the hand piece 157e is used, the ultrasonic wave output apparatus 162 is only required to operate, and the remaining devices are controlled to enter a standby state. Preferably, as the hand piece 157e is connected, the output of the ultrasonic wave output apparatus 162 is only set automatically. The set value is desirably equal to the same set value which was used by the same hand piece 157e at the preceding time.

An endoscope scissors hand piece 157f illustrated in FIG. 17 is a hand piece which is used both for incision and for coagulation. When this handpiece 157f is used, the ultrasonic wave output apparatus 162 and the pneumoperitoneum apparatus 164 operate exclusively in association (the pneumoperitoneum apparatus 174 feeds and sucks air in synchronism with the output of the ultrasonic wave output apparatus 162), to discharge smoke generated by an ultrasonic wave output from the abdominal pore.

Like the hand piece 157e, when the hand piece 157f is connected, the connection of the hand piece 157f is recognized to control the exclusive operation of the ultrasonic wave output apparatus 162 and the pneumoperitoneum apparatus 164 to in association, and to automatically set operating parameters. As the operating parameters, for example, the output value is set in the ultrasonic wave output apparatus 162, while an abdominal pore pressure is set in the pneumoperitoneum apparatus 164.

An open knife hand piece 157g illustrated in FIG. 17 is a hand piece which is used for emulsifying, destroying and aspirating a tissue of interest with ultrasonic waves. When this hand piece 157g is used, the ultrasonic wave output apparatus 162 and the perfusion/aspiration apparatus 163 exclusively operate in association (the perfusion/aspiration apparatus 163 performs perfusion and aspiration in synchronism with the output of the ultrasonic wave output apparatus 162). When the hand piece 157g is connected, the ultrasonic wave output apparatus 162 and the perfusion/aspiration apparatus 163 are controlled to exclusively operate in association, and operating parameters are automatically set. For the operating parameters for the perfusion/aspiration apparatus 163, predetermined amounts of perfusion and aspiration are set by way of example.

An endoscope knife hand piece 157h illustrated in FIG. 17 is a hand piece which is used for emulsifying destroying and aspirating a tissue of interest with ultrasonic waves. When this hand piece 157h is used, the ultrasonic wave output apparatus 162, the perfusion/aspiration apparatus 163, and the pneumoperitoneum apparatus 164 exclusively operate in association (the perfusion/aspiration apparatus 163 performs perfusion and aspiration, and the pneumoperitoneum apparatus 164 feeds and sucks air in synchronism with the output of the ultrasonic wave output apparatus 162), to discharge smoke generated in the abdominal pore by the output of the ultrasonic waves.

When the hand piece 157h is connected, the ultrasonic wave output apparatus 162, the perfusion/aspiration apparatus 163 and the pneumoperitoneum apparatus 164 are controlled to exclusively operate in association, and operating parameters are automatically set.

While the foregoing description on the configurations of the respective hand pieces also includes description on the operations thereof, the operation of an exemplary hand piece will be outlined below.

For example, for performing a treatment using the open bipolar hand piece 157c illustrated in FIG. 16 as the electric knife hand piece 157m as illustrated in FIG. 11, the open bipolar hand piece 157c is connected to the electric knife apparatus 161 and to the perfusion/aspiration apparatus 163.

Responsively, the hand piece discriminator 174 of the electric knife apparatus 161 discriminates that the type of the connected hand piece is the open bipolar hand piece 157c, and sends the result of the discrimination to the control unit 171. The control unit 171 controls the oscillator 172 to automatically set an output mode such as the waveform, and output setting in order to generate operating parameters suitable for performing a treatment for coagulation using the connected hand piece.

The control unit 171 also sends the discrimination result to the controller 165 through the communication cable 166, and the controller 165 sends a signal to the control unit 191 of the perfusion/aspiration apparatus 163 to operate in association with the electric knife apparatus 161. Then, as the operator manipulates the perfusion/aspiration switch 195 connected to the perfusion/aspiration apparatus 163, the control unit 191 senses the manipulation through the switch sensing unit 194, and controls the perfusion/aspiration apparatus 163 to perform perfusion and aspiration operations. Stated another way, the perfusion/aspiration apparatus 163 is responsive to the manipulation on the perfusion/aspiration switch 195 to perform the perfusion and aspiration operations with the connected hand piece (open bipolar hand piece 157c).

Also, the controller 191 automatically sets the operating parameters in accordance with a signal from the controller 165. Specifically, the control unit 191 controls the perfusion unit 192 and the aspiration unit 193 to perform the perfusion and aspiration operations with the amounts of perfusion and aspiration suitable for the open bipolar 157c.

Likewise, when another hand piece is connected for use with certain apparatus, the type of the connected hand piece is discriminated in a similar manner, and the result of the discrimination is used on to control a single device or a plurality of devices involved in an associative operation for the connected hand piece to operate or not, and to automatically set operating parameters for the hand piece.

As appreciated from the foregoing, according to the fifth embodiment, when a hand piece, with which a treatment is performed, is connected to a medical instrument which is operated together with the hand piece, the medical instrument, to which the hand piece is connected, automatically sets operating parameters required for the operation of the hand piece, so that the operator can rapidly and correctly perform the treatment without time-consuming and laborious works such as output settings and so on.

In the foregoing description, the type of the hand piece 157 is discriminated by detecting the resistance of the resistor 178 provided in the hand piece 157m (157n) as illustrated in FIG. 18 to discriminate the type of the hand piece 157m (157n) which contains the resistor 178.

Since this method substantially limits the number of discriminated hand pieces by the resistance of the resistor 178, the fifth embodiment discriminates the type of the hand piece.

Figure 19:
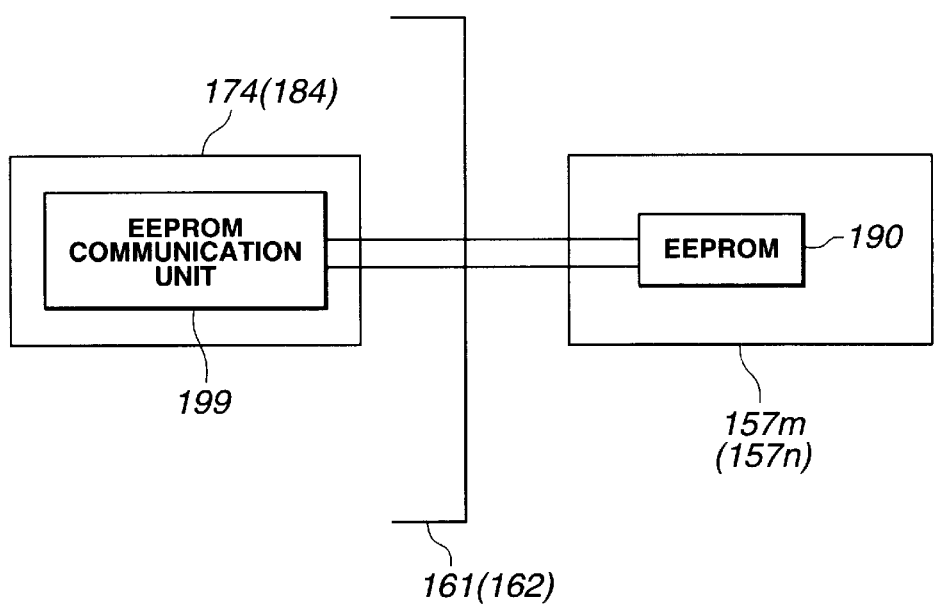

FIG. 19 illustrates a hand piece discriminating means according to a modification to the fifth embodiment for eliminating this limitation.

As illustrated in FIG. 19, each of hand pieces 157 (157m, 157n) is provided with EEPROM (electrically erasable programmable read only memory) 190 to store details of the log for previous uses, in addition to information on an identifier indicative of the type of the hand piece, settings for devices required for associative operation, and information on an operation mode.

The information stored in the EEPROM 190 can be read, information on settings can be changed and written into the EEPROM 190, and stale information in the EEPROM 190, which is no longer required, can be rewritten by an EEPROM communication unit (or an EEPROM read/write unit) 199 which forms part of the hand piece discriminator 174 (184) connected to the EEPROM 190 in the electric knife apparatus 161 or the ultrasonic wave output apparatus 162.

Also, with the aforementioned resistor-based discrimination, if a user has used a group of identical hand pieces and another user subsequently uses one of these hand pieces, the settings automatically set into the associated apparatus belong to the previous user, so that the settings must be changed as the case may be.

In this modification, the hand piece 157 provided with the EEPROM 190 is used to store a variety of settings and so on in the hand piece 157, so that the user may carry the particular hand piece 157 for exclusive use to allow for automatic setting and associative setting preferred to the user.

According to the foregoing modification, settings (a variety of parameters, associative control method, connection of devices) for devices required for a treatment are automatically captured only by connecting the hand piece 157, thereby providing the user with improved usability.

In addition, since devices required for a particular hand piece 157 are automatically set only by connecting the hand piece 157, the user can use the devices without erroneous manipulations.

In the foregoing description, the electric knife apparatus 161 and the ultrasonic wave output apparatus 162, which function as medical instruments for performing main control operations (such as output control) for the hand pieces 157*m*, 157*n*, are provided with the hand piece discriminators 174, 184, respectively, while the perfusion/aspiration apparatus 163 and the pneumoperitoneum apparatus 164, which function as medical instruments for performing ancillary (auxiliary) control operations, are not provided with the hand piece discriminator, such that they can be controlled through a communication means to operate or not to operate association. Alternatively, the ancillary medical instruments may be provided with the hand piece discriminator as well.

(Sixth Embodiment)

Next, a sixth embodiment of the present invention will be described with reference to FIGS. 20 and 21. The sixth embodiment is such that one of medical instruments, specifically, an ultrasonic wave output apparatus is connected to an output switching apparatus to allow a plurality of hand pieces to be connected simultaneously to the ultrasonic wave output apparatus.

Figure 20:
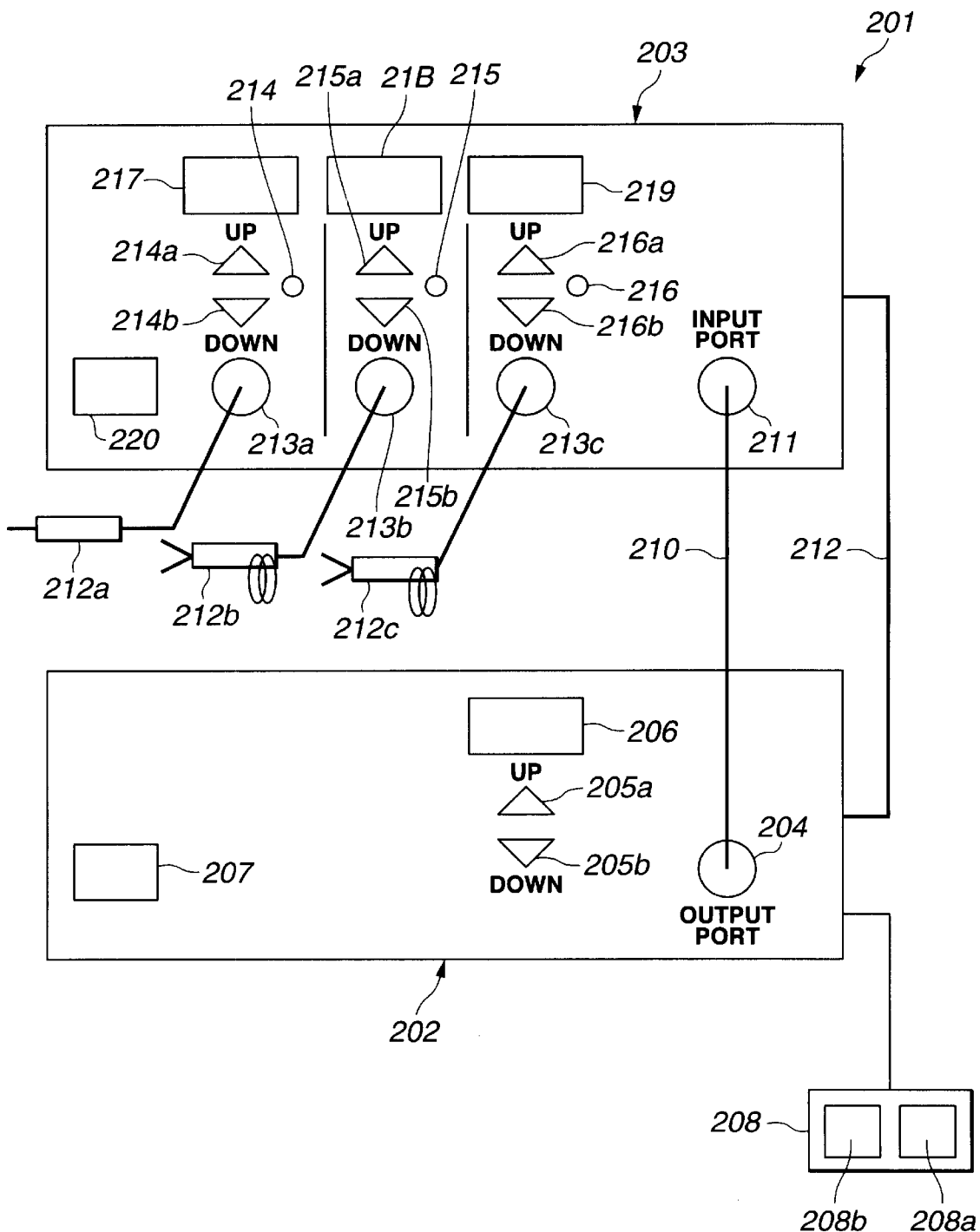

As illustrated in FIG. 20, an ultrasonic operation apparatus 201, which constitutes the sixth embodiment of the electric treatment system according to the present invention, comprises an ultrasonic wave output apparatus 202 and an output switching apparatus 203. The ultrasonic wave output apparatus 202 comprises an output port 204 from which ultrasonic waves are output; an up switch 205*a* and a down switch 205*b* for setting an ultrasonic wave output; a display unit 206 for displaying a set ultrasonic wave output and a power switch 207.

Also, the ultrasonic wave output apparatus 202 is connected to a foot switch 208. This foot switch 208 is a twin type one which has a foot pedal 208*a* for set output and a foot pedal 208*b* for rated output.

The foot switch 208*a* for a set output ON/OFF controls an ultrasonic driving signal output from the output port 204. As the operator steps on the foot pedal 208*a* for set output, the ultrasonic driving signal having a preset value is output from the output port 204. On the other hand, as the operator steps on the foot pedal 208*b* for rated output, a 100% ultrasonic driving signal is output from the output port 204 irrespective of the set ultrasonic wave output value.

This output port 204 is connected to the input port 212 provided in the output switching apparatus 203 through an ultrasonic wave transmission cable 210, so that an ultrasonic driving signal output from the ultrasonic wave output apparatus 202 is input to the output switching apparatus 203 through the ultrasonic wave transmission cable 210.

The output switching apparatus 203 is provided with a plurality of connection terminals 213*a*–213*c* which can be connected to a plurality of types, three types in the sixth embodiment, of hand pieces 212*a*–212*c* respectively. Above the connection terminals 213*a*–213*c*, selection switches 214–216 are provided corresponding to the respective connection terminals 213*a*–213*c* as selecting means for selecting a particular hand piece 212*a*–212*c*. The selection switches 214–216 comprise a triple type switch which is configured such that when one switch is turned ON, the remaining switches are turned OFF.

Also, adjacent to the respective selection switches 214–216, up switches 214*a*–216*a* and down switches 214*b*–216*b* are provided for setting ultrasonic wave output values. Above these switches, display units 217–219 are provided for displaying ultrasonic wave output values set by the respective switches 214*a*–216*a*, 214*b*–216*b*. Further, a power switch 220 is provided.

The hand pieces 212*a*–212*c* connected to the connection terminals 213*a*–213*c* may be an ultrasonic aspiration probe and ultrasonic scissors, by way of example. As one of the selection switches 214–216 is turned ON, an ultrasonic driving signal can be output to one of the hand pieces 212*a*–212*c* connected to the corresponding connection terminal 213*a*–213*c*.

The ultrasonic wave output apparatus 202 and the output switching apparatus 203 are connected through a communication cable 212, so that the output switching apparatus 203 transmits information on a selected hand piece, information on set outputs, and so on to the ultrasonic wave output apparatus 202. As the output switching apparatus 203 is connected to the ultrasonic wave output apparatus 202, the up switch 205*a* and the down switch 205*b* provided on the ultrasonic wave output apparatus 202 are disabled to operate, and the ultrasonic wave output value is remotely controlled by an up signal and a down signal transmitted from the output switching apparatus 203, and the resulting value is displayed on the display unit 206.

Figure 21:
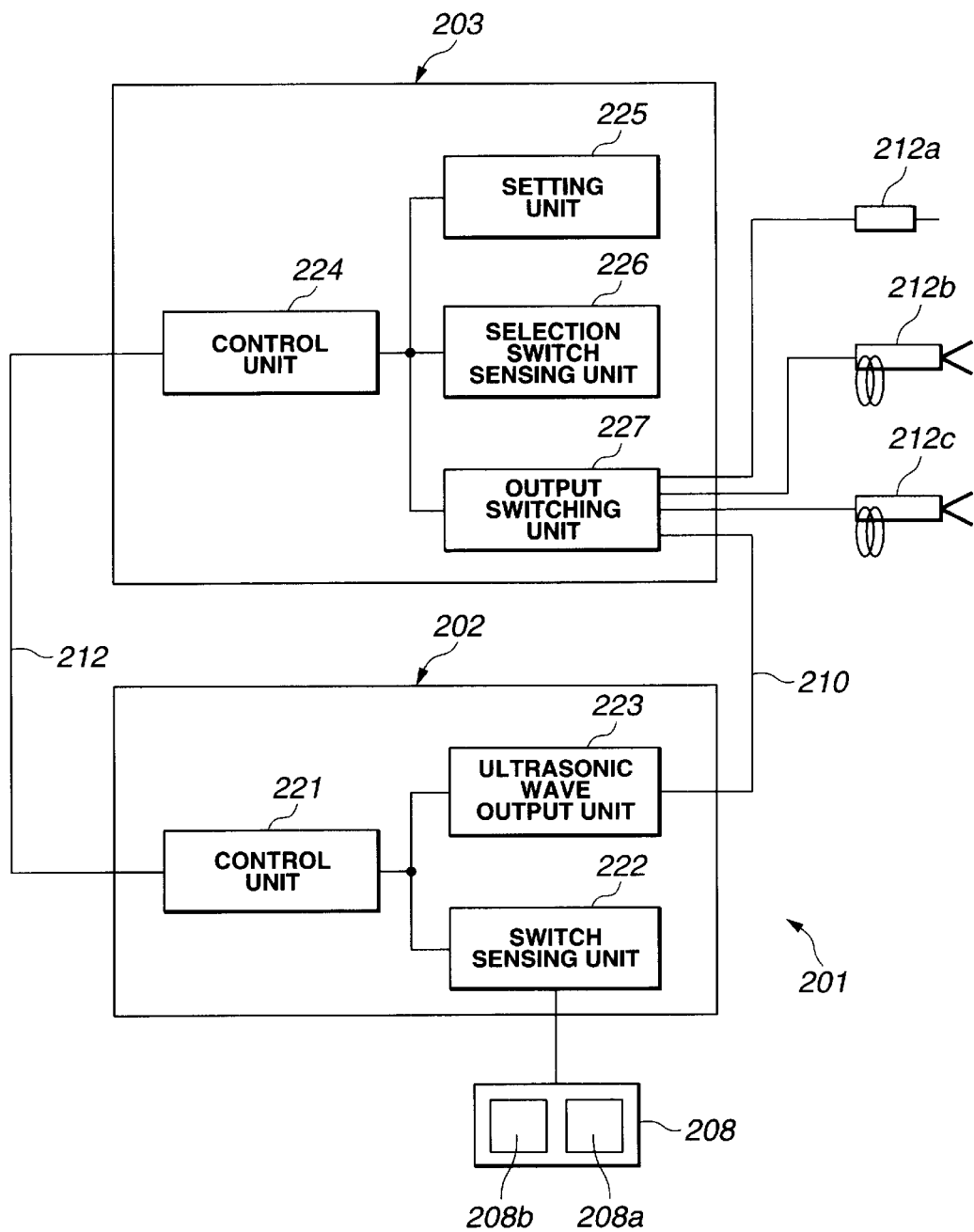

As illustrated in FIG. 21, the ultrasonic wave output apparatus 202 is provided with a control unit 221, a switch sensing unit 222, an ultrasonic wave output unit 223, and so on for carrying out functions required to control the output of the ultrasonic driving signal.

The output switching apparatus 203 in turn is provided with a control unit 224, a setting unit 225, a selected switch sensing unit 226, an output switching unit 227, and so on for carrying out functions required to set ultrasonic wave output values to connected hand pieces 212*a*–212*c*, and to transmit ultrasonic driving signals corresponding to the ultrasonic wave output values. The two control units 221, 224 are connected through the communication cable 212 to transmit and receive information therebetween.

Description will next be made on the operation of the sixth embodiment configured as described above will be describe.

The control unit 221 provided in the ultrasonic wave output apparatus 202 is connected to the control unit 224 provided in the output switching apparatus 203 through the communication cable 212, and the output port 204 of the ultrasonic wave output apparatus 202 is connected to the input port 211 of the output switching apparatus 203 through the ultrasonic wave transmission cable 210. In addition, the hand pieces 212a–212c are connected to the connection terminals 213a–213c, respectively, of the output switching apparatus 203.

Next, after turning ON the power switches 207, 220 of the ultrasonic wave output apparatus 202 and the output switching apparatus 203, respectively, ultrasonic wave output values are set for the respective hand pieces 212a–212c connected to the output switching apparatus 203. Since the ultrasonic wave output values are set to the respective hand pieces 212a–212c in accordance with the same procedure, the following will only describe the procedure for setting the ultrasonic wave output value to the hand piece 212a, as representative of the three hand pieces, and a description of the procedure for setting the ultrasonic wave output values for the remaining hand pieces 212b, 212c will be omitted.

For setting the ultrasonic wave output value to the hand piece 212a, the selection switch 214 provided on the output switching apparatus 203 is first turned ON to specify the hand piece 212a of interest. Then, the up switch 214a or the down switch 214b is manipulated to increase or decrease the ultrasonic wave output value to set it to a particular value.

The control unit 224 provided in the output switching apparatus 203 transmits a signal for identifying the ON state of the selection signal 214, sensed by the selected switch sensing unit 226, to the control unit 224.

The control unit 224 reads an identifying signal transmitted from the selected switch sensing unit 226 to recognize the connection terminal 213a to which the hand piece 212a is connected, and controls the output switching unit 227 to selectively connect the connection terminal 213a to the ultrasonic wave output unit 223 of the ultrasonic wave output apparatus 202 by switching relay contacts or the like, thereby allowing ultrasonic waves to be transmitted from the ultrasonic wave output unit 223.

Also, information on the ultrasonic wave output, set through manipulations on the up switch 214a or the down switch 214b and delivered from the setting unit 225, is transmitted to the control unit 221 of the ultrasonic wave output apparatus 202.

The control unit 221 reads the information on the ultrasonic wave output transmitted from the control unit 224 provided in the output switching apparatus 203 to set the ultrasonic wave output value transmitted from the ultrasonic wave output unit 223.

The ultrasonic wave output values for the respective hand pieces 212a–212c, which have been set in the manner described above, are stored in the setting unit 225.

Then, for treating a vital tissue of interest using the hand piece 212a, the selection switch 214 provided on the output switching apparatus 203 is first turned ON to specify the hand piece 212a to be used.

In response, the control unit 224 identifies the connection terminal 213a, to which the hand piece 212a is connected, based on an identifying signal from the selected switch sensing unit 226 which has sensed the ON state of the selection switch 214, reads an ultrasonic wave output value corresponding to the connection terminal 213a stored in the setting unit 225, and transmits the ultrasonic wave output information to the control unit 221 provided in the ultrasonic wave output apparatus 202.

The control unit 221 of the ultrasonic wave output apparatus 202 reads the ultrasonic wave output information transmitted from the control unit 224 of the output switching apparatus 203, and sets an output value for an ultrasonic driving signal output from the ultrasonic wave output unit 223. The ultrasonic wave output value is displayed on both the display units 206, 217 of the respective apparatus 202, 203.

Then, as the operator steps on the foot pedal 208a for a set output on the foot switch 208 connected to the ultrasonic wave output apparatus 202, the control unit 221 identifies the switch turned ON by the operator and sensed by the switch sensing unit 222, and transmits an ultrasonic wave output instruction to the ultrasonic wave output unit 223.

The ultrasonic wave output unit 223 outputs an ultrasonic driving signal having a preset output value to the output switching apparatus 203 based on the ultrasonic wave output instruction from the control unit 221.

The ultrasonic driving signal output from the ultrasonic wave output apparatus 202 is input to the input port 211 of the output switching apparatus 203 through the output port 204 and the ultrasonic wave transmission cable 210, and output from the input port 211 to the hand piece 212a connected to the connection terminal 213a through the output switching unit 227.

The ultrasonic driving signal output to the hand piece 212a causes an ultrasonic vibrator disposed at the distal end of the hand piece 212a to ultrasonically vibrate in order to perform treatments such as coagulation, incision, emulsification, and so on on a vital tissue of interest.

As the operator steps on the foot pedal 208b for a rated output on the foot switch 208, the ultrasonic wave output unit 223 outputs a 100% ultrasonic driving signal to the output switching apparatus 203 irrespective of any preset ultrasonic wave output value, so that the ultrasonic vibrator disposed in the hand piece 212a ultrasonically vibrates at a full output value.

For performing a treatment using another hand piece 212b or 212c, a corresponding selection switch 215 or 216 is turned ON. In this event, the selection switch 214 corresponding to the connection terminal 213a to which the hand piece 212a is connected, is turned OFF in association with the turn-ON of the selection switch 215 or 216.

As a result, the ultrasonic driving signal can be output to the selected hand piece 212b or 212c.

As described above, in the sixth embodiment, the output switching apparatus 203 is connected to the ultrasonic wave output apparatus 202 such that an ultrasonic driving signal can be selectively output from the output switching apparatus 203 to the plurality of hand pieces 212a–212c, thereby making it possible to use the plurality of hand pieces 212a–212c without the need for exchanging one with another each time a different hand piece is used, to provide good handling, and to select output settings suitable for different hand pieces (for example, an ultrasonic aspiration probe, ultrasonic scissors, and so on).

Figure 22:
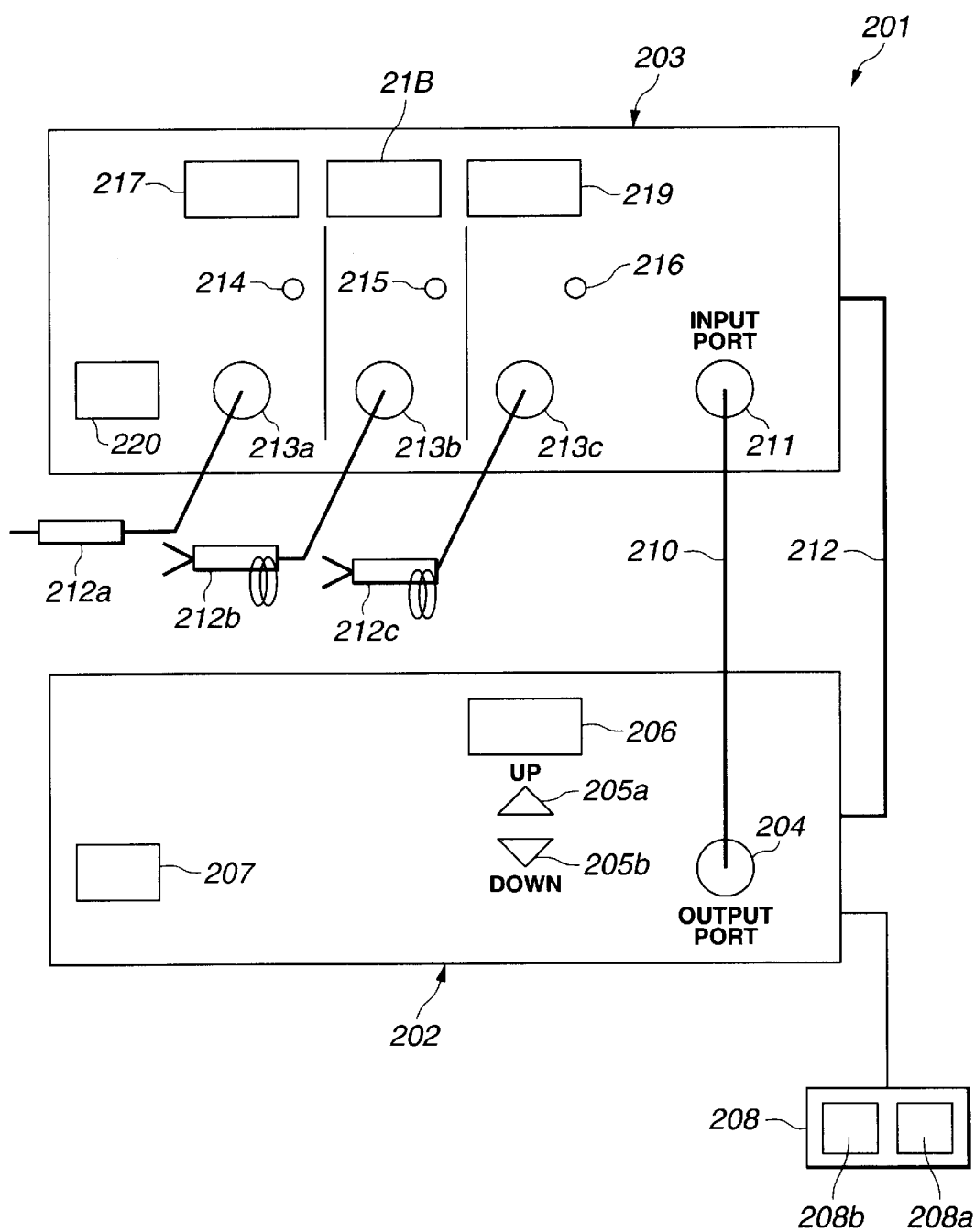

FIG. 22 illustrates an an ultrasonic operation apparatus according to a modification made to the sixth embodiment. In the sixth embodiment, ultrasonic wave output values for the respective hand pieces 212a–212c are set on the output switching apparatus 203, whereas in this modification, such settings are made by the up switch 205a and the down switch 205b provided on the ultrasonic wave output apparatus 202.

Therefore, the output switching apparatus 203 in the modification does not require the up switch and the down switch employed in the sixth embodiment.

Specifically, as the selection switch 214 (215 or 216) provided on the output switching apparatus 203 is turned ON, an ultrasonic wave output value output from the selected connection terminal 213a (213b or 213c) is displayed on the display unit 206 of the ultrasonic wave output apparatus 202 through the communication cable 212.

The operator, while viewing the value displayed on the display unit 206, manipulates the up switch 205a or the down switch 205b to set an ultrasonic wave output value to be output to the hand piece 212a (212b or 212c) connected to the connection terminal 213a (213b or 213c). It should be noted that this ultrasonic wave output value is displayed also on the display unit 217 (218 or 219) of the output switching apparatus 203.

As described above, according to the modification, ultrasonic wave output values output from the connection terminals 213a–213c provided on the output switching apparatus 203 can be set by manipulating one of the up switch 205a and the down switch 205b provided on the ultrasonic wave output apparatus 202, thereby making it possible to simplify the configuration of the output switching apparatus 203 and accordingly reduce the manufacturing cost.

(Seventh Embodiment)

Figure 23:
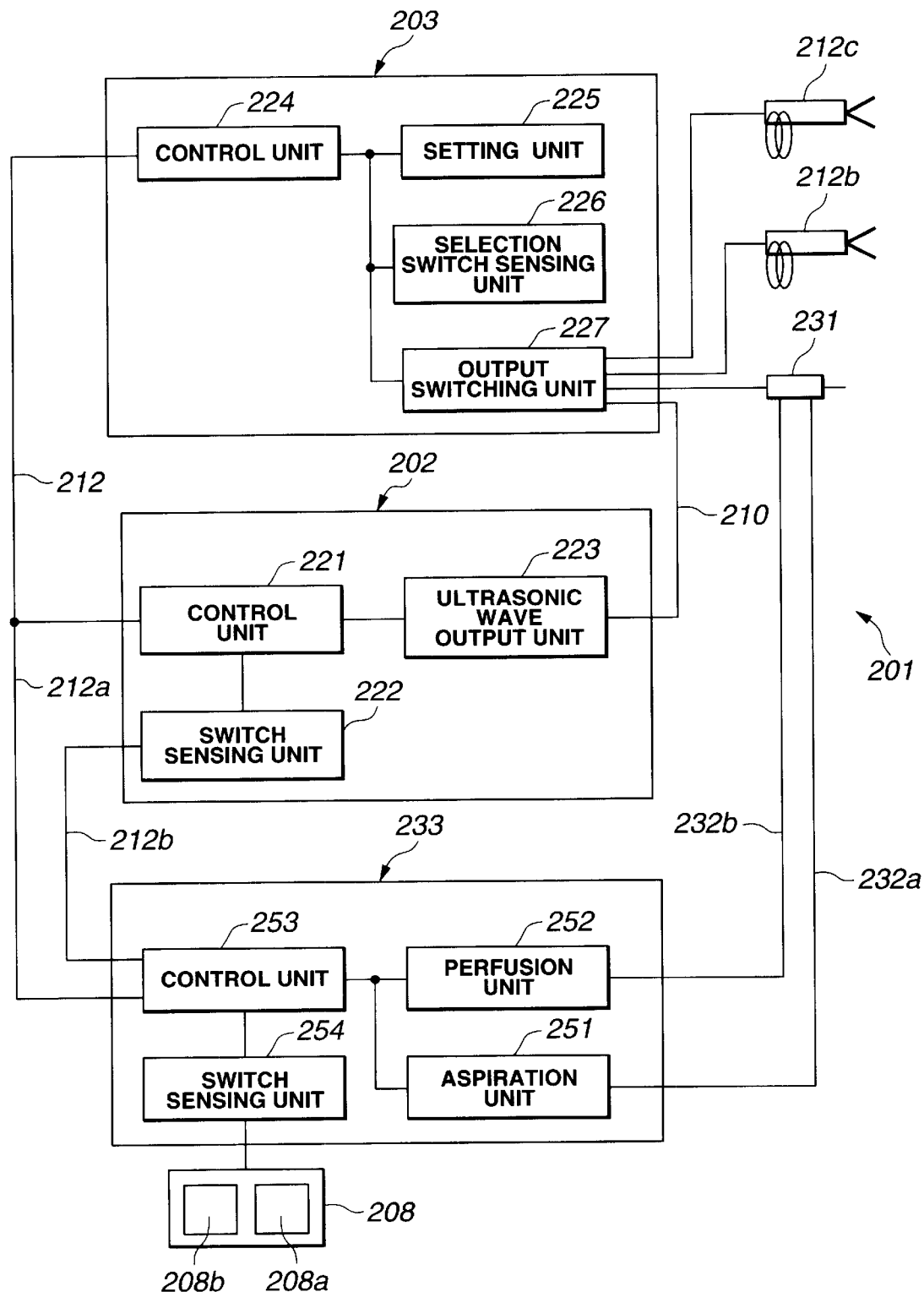

Next, a seventh embodiment of the present invention will be described with reference to FIGS. 23 through 25. The seventh embodiment shows a manner in which an ultrasonic aspiration/operation hand piece 231 is connected to the output switching apparatus 203.

In an operation using the ultrasonic aspiration/operation hand piece 231, when the system is powered on to start using the hand piece 231, cooling water must be filled in the hand piece 231 up to the tip of a probe disposed at the distal end of the hand piece 231 to prevent the probe from heating. For this reason, a perfusion/aspiration apparatus 233 is additionally provided for supplying cooling water to the ultrasonic aspiration/operation hand piece 231 and for aspirating the supplied cooling water.

Also, when the hand piece 231 is first used after the system is powered on, no ultrasonic waves can be output unless the hand piece 231 is previously supplied with a set amount of cooling water or for a fixed time period in order to prevent the probe from heating.

When the ultrasonic aspiration/operation hand piece 231 is connected to one of the connection terminals 213a–213c of the output switching apparatus 203 shown in the sixth embodiment, the respective connection terminals 213a–213c are switched by the selection switches 214–216. Therefore, when the ultrasonic aspiration/operation hand piece 231 is once used and switched to another hand piece for use, the perfusion/aspiration apparatus 233 recognizes the removal of the ultrasonic aspiration/operation hand piece 231, so that when the ultrasonic aspiration/operation hand piece 231 is again selected by the output switching apparatus 203, the perfusion/aspiration apparatus 233 again supplies cooling water before an ultrasonic driving signal is output, recognizing that the ultrasonic aspiration/operation hand piece 231 is newly connected.

To eliminate this drawback, in the seventh embodiment, after the system is powered on, it is examined whether or not the ultrasonic aspiration/operation hand piece 231 is used for the first time, and an ultrasonic driving signal is immediately output if not the first use.

In the following, the configuration of the seventh embodiment will be described with reference to FIG. 23. When the ultrasonic aspiration/operation hand piece 231 is connected to any of the connection terminals 213a–213c of the output switching apparatus 203, the control unit 224 of the output switching apparatus 203 identifies the type of the connected hand piece, and transmits information on the type of the hand piece to the ultrasonic wave output apparatus 202 and to the perfusion/aspiration apparatus 233 through communication cables 212, 212a, respectively.

An aspiration tube 232a and a perfusion tube 232b extend from the ultrasonic aspiration/operation hand piece 231, and are connected to an aspiration unit 251 and a perfusion unit 252 provided in the perfusion/aspiration apparatus 233.

The perfusion/aspiration apparatus 233 is provided with a control unit 253 and a switch sensing unit 254, and the perfusion unit 252, the aspiration unit 251 and the switch sensing unit 254 are controlled by the control unit 253.

As the operator steps on one of the foot pedal 208a for the set output and the foot pedal 208b for the rated output provided on the foot switch 208, the control unit 253 outputs a sensing signal indicative of the foot pedal 208a or 208b, sensed by the switch sensing unit 254, to the switch sensing unit 222 provided in the ultrasonic wave output apparatus 202 to output ultrasonic waves at a predetermined output value to a hand piece 212a, 212b or 231 selected by the operator, in a manner similar to the sixth embodiment. In this event, a triple foot switch may be used instead to additionally provide a perfusion pedal such that the perfusion unit 252 alone can be controlled independently.

For example, with the ultrasonic aspiration/operation hand piece 231 connected to the connection terminal 213a of the output switching apparatus 203 (see FIG. 20), as the operator turns ON the selection switch 214 to select the ultrasonic aspiration/operation hand piece 231, the distal end of the ultrasonic aspiration/operation handpiece 231 vibrates to perform a treatment such as emulsification, destruction or the like of a vital tissue of interest.

Simultaneously, from an opening (not shown) formed at the distal end of the ultrasonic aspiration/operation hand piece 231, the emulsified or destroyed vital tissue, cooling liquid, blood, and so on are aspirated by the aspiration unit 251 through the aspiration tube 232a. The aspiration unit 251 remains operative after the perfusion/aspiration apparatus 233 is powered on.

On the other hand, the perfusion unit 252 of the perfusion/aspiration apparatus 233 supplies a cooling liquid (washing liquid) from an opening (not shown) formed at the distal end of the ultrasonic aspiration/operation hand piece 231 through the perfusion tube 232b. The perfusion unit 252 is set to supply a cooling water in synchronism with an ultrasonic wave output, i.e., in synchronism with one of the foot pedals 208a, 208b provided on the foot switch 208 which has been turned ON by the operator.

In this event, if the ultrasonic aspiration/operation hand piece 231 is connected for the first time after the power is on, ultrasonic waves are prevented from outputting until an initial setting (flushing) is completed for filling the ultrasonic aspiration/operation hand piece 231 with cooling water before ultrasonic waves are output to the ultrasonic aspiration/operation hand piece 231.

Means for recognizing whether or not the initial setting is completed in this event may be implemented by a flow sensor or the like combined with the ultrasonic aspiration/operation hand piece 231. For simplicity, however, the completion of the initial setting may be recognized on condition that the cooling water has been supplied for a fixed time period.

Figure 24:
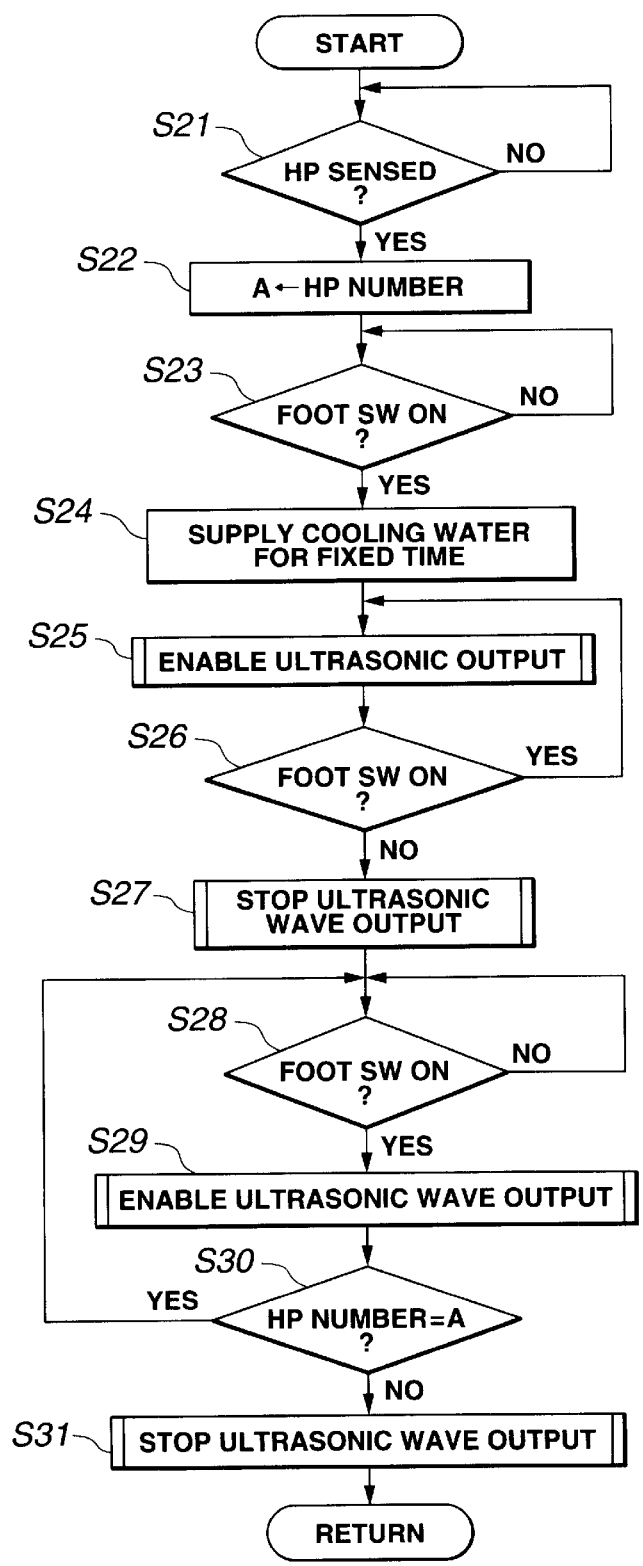

The initial setting performed in a simplified manner, and determination as to whether or not the initial setting is completed may be processed in accordance with a flow chart illustrated in FIG. 24.

The illustrated routine is repeatedly executed for each of the connection terminals 213a–213c (see FIG. 20) provided on the output switching apparatus 203 at predetermined operation periods after the power switch is turned ON.

Specifically, as the power switch is turned ON, it is first examined at step S21 whether or not the ultrasonic aspiration/operation hand piece (HP) 231 is connected to a connection terminal of the output switching apparatus 203 which is to be sensed. If not connected, the routine is repeatedly executed to prepare for the ultrasonic aspiration/operation hand piece 231 which would be connected to the connection terminal.

If a normal hand piece other than the ultrasonic aspiration/operation hand piece 231 is connected to the connection terminal, subjected to sensing, of the output switching apparatus 203, the normal ultrasonic wave output control is performed without executing this routine.

On the other hand, when the ultrasonic aspiration/operation hand piece 231 is connected to the connection terminal of the output switching apparatus 203, the routine proceeds to step S22, where the number of the hand piece 231 is stored as an identifying flag A.

For the determination as to whether or not the ultrasonic aspiration/operation hand piece 231 is connected to the connection terminal, subjected to sensing, of the output switching apparatus 203, and the determination as to whether or not a connected hand piece is the ultrasonic aspiration/operation hand piece 231, a connector in each of the hand pieces 212a–212c, 231 may be provided, for example, with a resistor for identification. When the hand piece is connected, a constant current is supplied to the resistor to generate a voltage there across which is compared with a voltage value previously set for each type of hand piece to make the foregoing determinations.

Subsequently, the routine proceeds to step S23, where it is determined whether any of the foot pedals 208a, 208b of the foot switch 208 is turned ON. If both the foot pedals remain OFF, this routine is repeatedly executed to wait for the foot pedal 208a or 208b to be turned ON.

Eventually, when one of the foot pedals 208a, 208b is turned ON, the routine proceeds to step S24, where cooling water is supplied for a fixed time period to the ultrasonic aspiration/operation hand piece 231 connected to the connection terminal subjected to sensing, in order to fill the passage with the cooling water. After the cooling water has been supplied in a predetermined manner, i.e., after the initial setting (flushing) is completed for the ultrasonic aspiration/operation hand piece 231, the routine proceeds to step S25 to allow ultrasonic waves to be output to the ultrasonic aspiration/operation hand piece 231.

Subsequently, the routine proceeds to step S26, where it is again determined whether or not one of the foot pedals 208a, 208b of the foot switch 208 is ON. When the foot pedal 208a or 208b still remains ON, the routine returns to step S25. Conversely, when the foot pedal 208a or 208b is switched from ON to OFF, the routine proceeds to step S27, where the ultrasonic wave output to the ultrasonic aspiration/operation hand piece 231 is stopped, followed by the routine proceeding to step S28 to wait for one of the foot pedals 208a, 208b to be turned ON.

Then, when one of the foot pedals 208a, 208b is turned ON, for example, when the ultrasonic aspiration/operation hand piece 231 is used again after another hand piece 212a or 212b has been used, the routine proceeds to step S29, where an ultrasonic wave output is allowed. Next, at step S30, it is determined whether or not the currently connected hand piece is the ultrasonic aspiration/operation hand piece 231 by matching the value of the stored identifying flag A with the HP number read from the connected hand piece. If they match, this means that the initial setting has been completed for the ultrasonic aspiration/operation hand piece 231, so that the routine returns to step S28, where the ultrasonic wave output is allowed for the ultrasonic aspiration/operation hand piece 231 until both the foot pedals 208a, 208b are turned OFF.

Consequently, when the ultrasonic aspiration/operation hand piece 231 is repeatedly used without being removed from the connection terminal provided on the output switching apparatus 203, the ultrasonic wave output is immediately allowed since the initial setting has been already completed when the ultrasonic aspiration/operation hand piece 231 was connected for the first time. Therefore, even when the output switching apparatus 203 is used, the ultrasonic aspiration/operation hand piece 231 can be prevented from heating. Furthermore, since the user need not perform the initial setting each time the user again uses the ultrasonic aspiration/operation hand piece 231, good handling is provided.

At step S30, when it is determined that the value of the identifying flag A does not match the HP number, i.e., when it is determined that another hand piece 212a or 212b is connected to the connection terminal, subjected to sensing, provided on the output switching apparatus 203, the routine proceeds to step S31, where the ultrasonic wave output is stopped, and the routine is exited.

Figure 25:
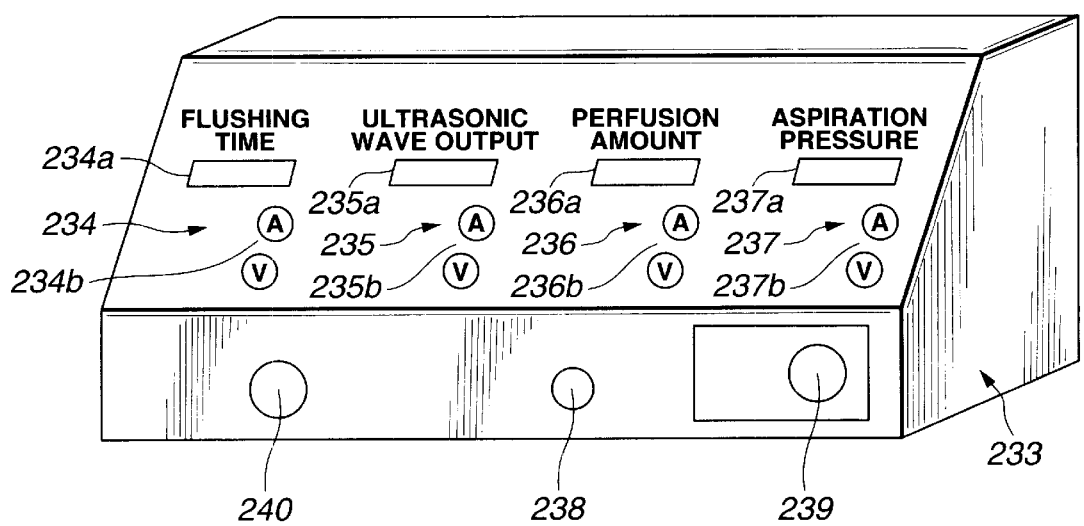

In the initial setting procedure, for example as illustrated in FIG. 25, the perfusion/aspiration apparatus 233 may be provided with a flushing time setting unit 234, an ultrasonic wave output setting unit 235, a perfusion amount setting unit 236 and an aspiration pressure setting unit 237, such that an ultrasonic wave output value, a flushing time, and the perfusion amount during flushing are automatically associated with one another. Since a larger ultrasonic wave output set value causes a larger amount of heat generated in the ultrasonic aspiration/operation hand piece 231, the flushing time and the perfusion amount during the flushing may be automatically increased. In this event, if a maximum perfusion amount is limited due to a flow path resistance of the ultrasonic aspiration/operation hand piece 231, the flushing time may be extended.

In FIG. 25, the perfusion/aspiration apparatus comprises display units 234a–237a for displaying set values for the setting units 234–237, respectively; up/down switches 234b–237b for manually setting the set amounts for the setting units 234–237, respectively; and a pinch valve 238 for connecting the aspiration tube 232a extending from the ultrasonic aspiration/operation hand piece 231. The pitch value 238 controls closure/opening of the aspiration tube 232a.

Further, the perfusion/aspiration apparatus comprises a perfusion pump 239 connected to the perfusion tube 232b; and an ultrasonic connector 240 to which the ultrasonic aspiration/operation hand piece 231 is directly connected when the perfusion unit/aspiration apparatus 233 is used alone.

As described above in detail, the sixth and seventh embodiments provide operational advantages as follows.

The output switching apparatus is provided between the ultrasonic wave output apparatus and a plurality of hand pieces, such that the output switching apparatus allows selection of a hand piece to which an ultrasonic wave output is supplied.

A hand piece to which ultrasonic waves are output is specified by the output switching unit provided in the output switching apparatus. Since the output switching apparatus is provided with display units for displaying ultrasonic wave output values and setting units for setting ultrasonic wave output values, corresponding to the respective hand pieces, to set and display the ultrasonic wave outputs independently of one another, the operator can recognize the set ultrasonic wave outputs at all times.

The ultrasonic wave output apparatus and the output switching apparatus can transmit and receive information therebetween through communication means.

When an ultrasonic aspiration/operation hand piece is used, the type of the hand piece is sensed. When the ultrasonic aspiration/operation hand piece is once switched to another hand piece by the output switching apparatus, and is again selected, the previous cooling water supply before outputting ultrasonic waves is eliminated to immediately allow the output of an ultrasonic driving signal when the type of the previously recognized hand piece matches the type of the currently selected hand piece.

(Eighth Embodiment)

Next, an eighth embodiment of the present invention will be described with reference to FIGS. 26 through 28. The eighth embodiment allows a perfusion/aspiration apparatus, functioning as a fluid supply/recovery apparatus, to be used in association with either of an ultrasonic wave output apparatus and an electric knife apparatus.

Figure 26:
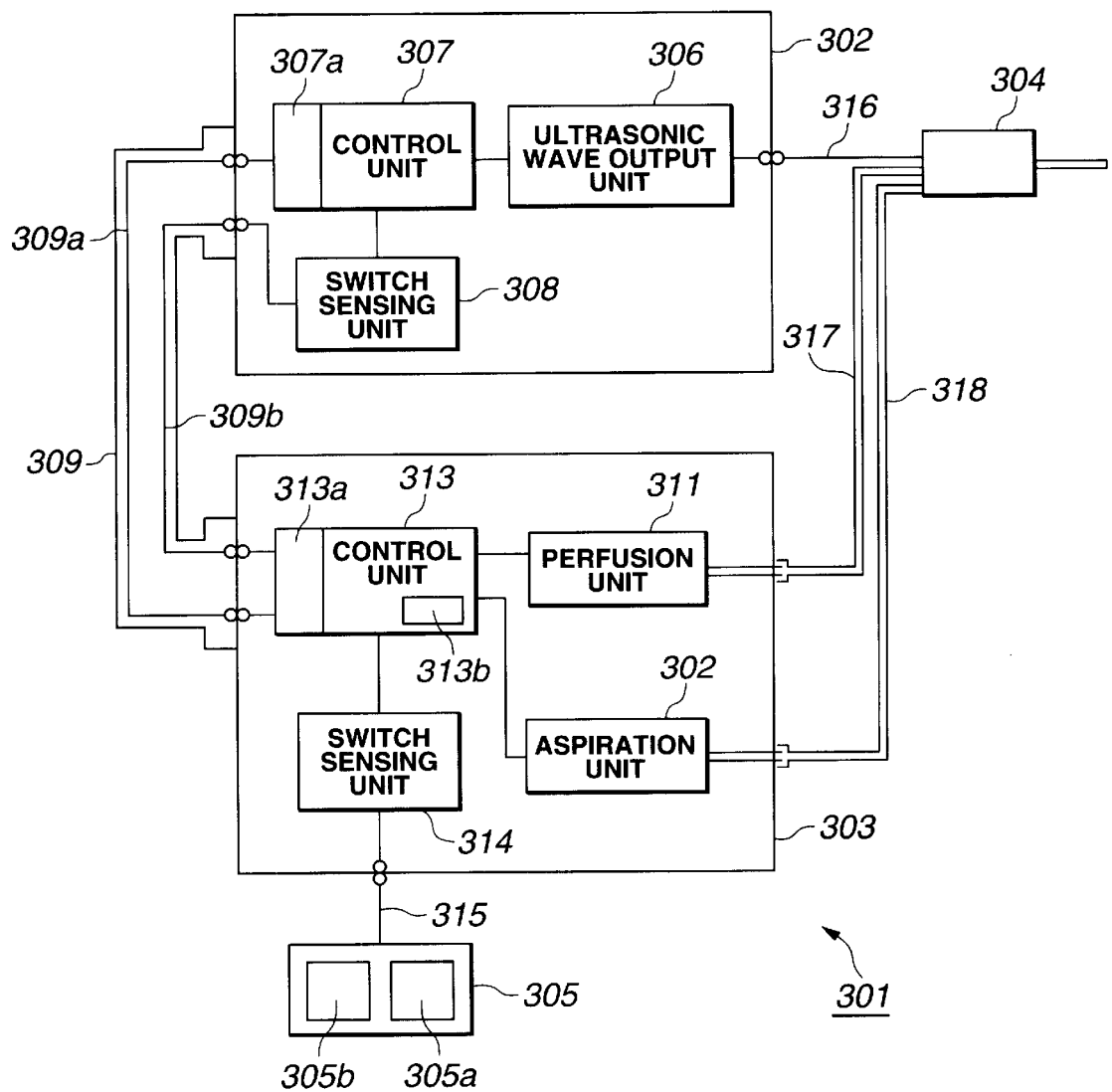

As illustrated in FIG. 26, an ultrasonic treatment system 301 according to the eighth embodiment, which constitutes the electric treatment system of the present invention, comprises an ultrasonic wave output apparatus (ultrasonic apparatus main body) 302 for incising, coagulating, emulsifying and aspirating a vital tissue of interest utilizing ultrasonic waves; a perfusion/aspiration apparatus (perfusion/aspiration apparatus main body) 303 connected to the ultrasonic wave output apparatus 302 through a communication cable 309 and functioning as a fluid supply/recovery apparatus; an ultrasonic hand piece 304 connected to the ultrasonic wave output apparatus 302 and to the perfusion/aspiration apparatus 303 and functioning as an ultrasonic treatment unit grabbed by the operator for performing ultrasonic-based treatments; and a foot switch 305 connected, for example, to the perfusion/aspiration apparatus 303 for controlling an ultrasonic wave output operation and a perfusion operation.

In the ultrasonic treatment system 301, the ultrasonic wave output apparatus 302 and the perfusion/aspiration apparatus 303 are configured as separate units.

The ultrasonic wave output apparatus 302 illustrated in FIG. 26 comprises an ultrasonic wave output unit 306 for outputting ultrasonic waves; a control unit 307 for controlling the operation of the ultrasonic wave output unit 306 and so on; and a switch sensing unit 308 for detecting switching operations on an ultrasonic pedal 305a and a perfusion pedal 305b of the foot switch 305 through the perfusion/aspiration apparatus 303.

The control unit 307 includes a communication unit 307a for bidirectionally communicating with a device connected through a communication cable 309, in this embodiment the perfusion/aspiration apparatus 303. The communication unit 307a in turn contains a generating means for generating ID information which allows for identification of the type of the ultrasonic wave output apparatus 302 and also serves as unique information. The communication unit 307a also includes an identifying means for identifying the type or the like of a device connected thereto through the communication cable 309 based on ID information from the device.

The ultrasonic wave output unit 306 is composed of a power supply, a control unit, an oscillator, an output unit, and a sensor, all of which are required to output ultrasonic waves.

The perfusion/aspiration apparatus 303 in turn comprises a perfusion unit 311 for performing perfusion; an aspiration unit 312 for performing aspiration; a control unit 313 for controlling these components; and a switch sensing unit 314 for sensing switching operations on the foot switch 305 connected to the perfusion/aspiration apparatus 303. The foot switch 305 is removably connected to the perfusion/aspiration apparatus 303 through a connection cable 315.

The control unit 313 of the perfusion/aspiration apparatus 303 is removably connected between the perfusion/aspiration apparatus 303 and the ultrasonic wave output apparatus 302, connected to the control unit 307 of the ultrasonic wave output apparatus 302 through a signal line 309a of a communication cable 309 for communications, and also connected to the switch sensing unit 308 of the ultrasonic wave output apparatus 302 through a signal line 309b of the communication cable 309.

The control unit 313 includes a communication unit 313a for bidirectionally communicating with a device connected through the communication cable 309. In this embodiment the device is (the communication unit 307a in) the control unit 307 of the ultrasonic wave output apparatus 302. The communication unit 313a also contains a generating means for generating ID information which allows for identification of the type of the perfusion/aspiration apparatus 303 and also serves as unique information. In addition, the communication unit 313a includes an identifying means for identifying the type or the like of a device connected through the communication cable 9 based on ID information from the device (in the eighth embodiment, the ID information is comprised, for example, of a type code field indicative of the type of a device, and an ID code field unique to the device, and this ID information is sent to allow for identification among devices of the same type as the type of the connected device).

The perfusion/aspiration apparatus 303 can change the perfusion amount from the perfusion unit 311, and the aspiration amount (aspiration pressure) by the aspiration unit 312 in accordance with a device and a treatment tool connected thereto.

For this purpose, set values for the perfusion amount and the aspiration amount (aspiration pressure) corresponding to a connected device are previously stored in a storage unit 313b, implemented by a memory or the like, in the control unit 313. When a device having an ID code corresponding to a previously connected device is again connected, the set values used at the preceding time are displayed on a display panel, not shown. If the displayed set values are not changed, perfusion and aspiration operations are performed at the previous set values.

The ultrasonic wave hand piece 304 is removably connected to the ultrasonic wave output unit 306 of the ultrasonic wave output apparatus 302 through an ultrasonic driving cable 316. The ultrasonic wave hand piece 304 is also removably connected to the perfusion unit 311 and the aspiration unit 312 of the perfusion/aspiration apparatus 303 through a perfusion tube 317 and an aspiration tube 318, respectively.

When the ultrasonic wave output apparatus 302 is connected to the perfusion/aspiration apparatus 303, the ultrasonic wave output apparatus 302 is controlled in association with perfusion and aspiration functions, thereby allowing for destruction, emulsification, washing and aspiration of a tissue of interest (when an electric knife apparatus is connected as described in the next embodiment, the ultrasonic wave output apparatus 302 is controlled only in association with the perfusion function, whereby a tissue of interest can be coagulated while it is washed and cooled).

As described above, the ultrasonic operation system 301 has the ultrasonic wave output apparatus 302 and the perfusion/aspiration apparatus 303 connected through the communication cable 309 such that the associative control can be performed as described below.

It should be noted that when an electronic knife apparatus (high frequency output apparatus) is connected to the perfusion/aspiration apparatus 303 in place of the ultrasonic wave output apparatus 302, the perfusion/aspiration apparatus 303 can be controlled in association with the electric knife apparatus.

Then, as the ultrasonic wave output apparatus 302 is connected to the perfusion/aspiration apparatus 303, they begin communicating with each other. The two apparatus rely on the ID information unique to the apparatus to recognize the apparatus which is currently connected thereto.

On the other hand, if they cannot recognize the currently connected apparatus, the associative control is disabled, forcing the respective apparatus to operate independently.

The ID information is mutually transmitted and received at regular intervals. If a different ID is returned, or if no return is received, a connection failure is recognized to execute communication error processing. For example, an alarm is generated to stop the operation of the apparatus.

Next, the communication processing of the perfusion/aspiration apparatus 303 according to the eighth embodiment will be described with reference to FIG. 27.

As the communication processing is started, it is determined whether or not the ultrasonic wave output apparatus 403 is connected, as shown at step S41. Specifically, the control unit 313 of the perfusion/aspiration apparatus 303 bidirectionally communicates, by way of the communication unit 313*a*, with a device connected to the perfusion/aspiration apparatus 303 through the communication cable 309 to determine whether or not the device type indicates the ultrasonic wave output apparatus 303 from ID information returned in response to a signal for inquiring the device type on the other party.

When the determination indicates that the ultrasonic wave output apparatus 303 is connected, it is determined whether or not the device ID (ID information) of the connected device has changed, as shown at step S42. When the device ID of the connected device is not changed, associative control processing with the ultrasonic wave output apparatus 303 is executed at step S43. After the associative control processing, the routine returns to step S42 to monitor whether or not the device ID of the connected device has changed.

If the device ID of the connected device has changed, communication error processing is executed at step S44.

As the communication error processing, for example, the error is displayed for warning only on the device in which the error has occurred, while the connected device (in this event, the ultrasonic wave output apparatus having an ID code field different from the previous ID code field) is temporarily stopped without displaying the error. Then, after the error is removed (by manipulating a reset switch or the like), the connected device becomes operative as well.

On the other hand, when it is determined at step S41 that the ultrasonic wave output apparatus 303 is not connected, it is determined whether or not an electric knife apparatus is connected, as shown at step S45. When determining that no electric knife apparatus is connected, the perfusion/aspiration apparatus 303 is operated alone, as shown at step S46.

Conversely, if it is determined at step S45 that an electric knife apparatus is connected, it is determined whether or not the device ID of the connected device has changed, as shown at step S47. When the device ID of the connected device has not changed, associative control processing with the electric knife apparatus is executed at step S48. After this associative control processing, the routine returns to step S47 to monitor whether the device ID of the connected device has changed.

Then, if a change is found in the device ID of the connected device, the communication error processing is performed at step S44. While the associative control with the electric knife apparatus is relevant to the next embodiment, description thereon has been made in connection with FIG. 27.

Figure 28:
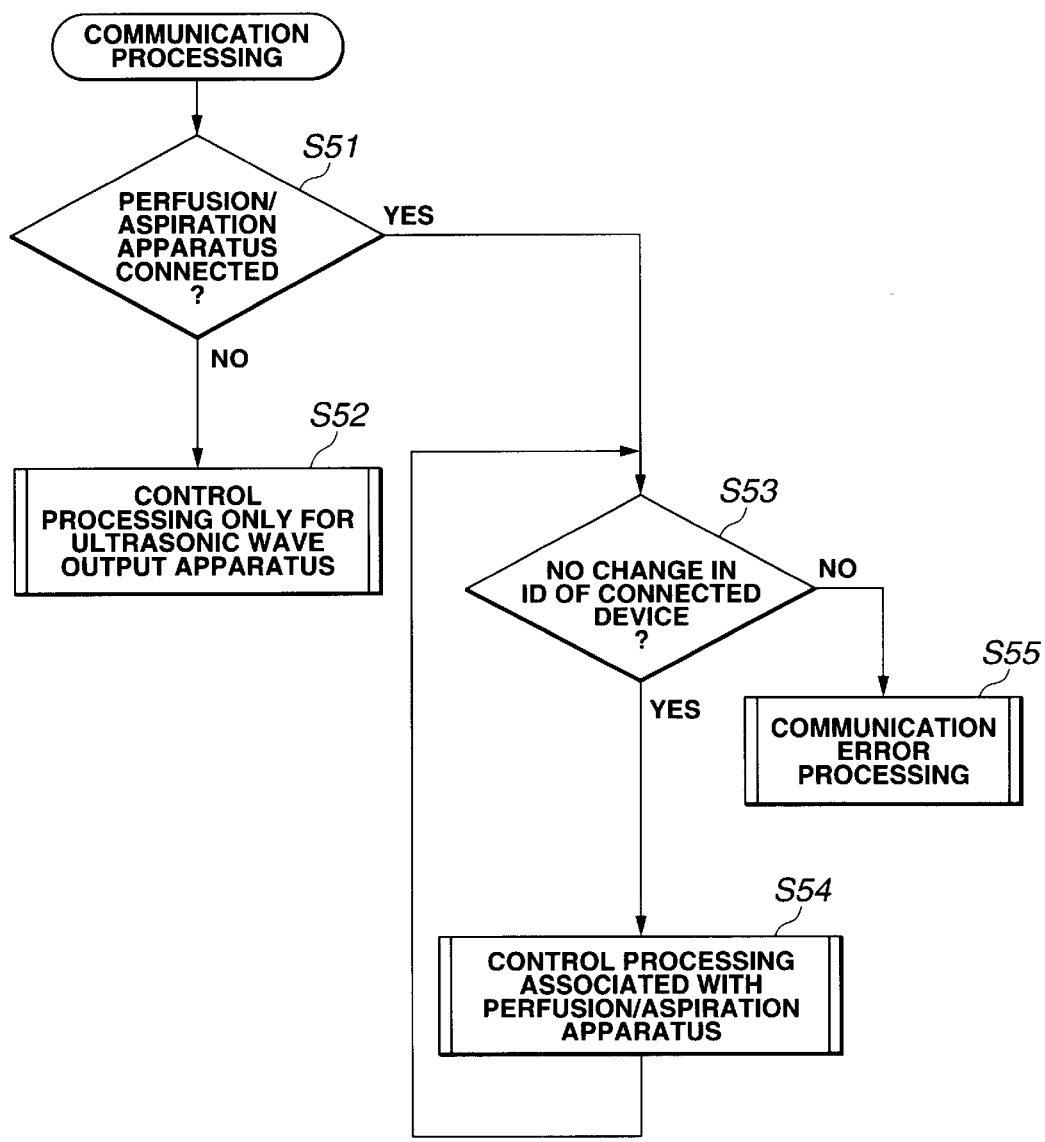

The ultrasonic wave output apparatus 302 in turn executes communication processing as illustrated in FIG. 28. As the communication processing is started, it is determined whether or not the perfusion/aspiration apparatus 303 is connected, as shown at step S51. Specifically, the control unit 307 of the ultrasonic wave output apparatus 302 sends a signal for inquiring the device type to a device on the other party (in this case, the perfusion/aspiration apparatus 303), connected to the ultrasonic wave output apparatus 302 through the communication cable 309, by way of the communication unit 307*a*, and determines whether or not the type of the connected device is the perfusion/aspiration apparatus 303 from information in the type code field of returned ID information.

When it is determined that the perfusion/aspiration apparatus 303 is not connected, the ultrasonic wave output apparatus 302 is controlled independently as shown at step S52. Conversely, when it is determined that the perfusion/aspiration apparatus 303 is connected, it is also determine whether or not the device ID of the connected device has changed, as shown at step S53. If no change is found in the device ID of the connected device, the ultrasonic wave output apparatus 302 is controlled in association with the perfusion/aspiration apparatus 303 at step S54. After this associative control processing, the routine returns to step S53 to monitor whether or not the device ID of the connected device has changed.

Then, if the ID of the connected device has changed, communication error processing is executed at step S55.

As previously described in connection with FIG. 27, the communication error processing is such that the error is displayed for warning only on the device in which the error has occurred, while the connected device is temporarily stopped without displaying the error. Then, after the error is removed, the connected device becomes operative as well.

As described above with reference to FIGS. 27 and 28, in the ultrasonic operation system 301, connection through the communication cable 309 is relied on to identify the type of a connected device on the other party, such that the control processing can be executed in association with that device. If no device is connected, each device may be controlled independently.

Next, the operation involved in the associative control will be described below.

The ultrasonic wave output apparatus 302 and the perfusion/aspiration apparatus 303 are brought into an associative control enabled state when mutual connection thereof is recognized by the ID information of the two parties.

Subsequently, as the ultrasonic hand piece 304 is connected to the ultrasonic wave output apparatus 302, information on this connection is transmitted from the control unit 307 of the ultrasonic wave output apparatus 302 to the control unit 313 of the perfusion/aspiration apparatus 303, and the control unit 313 sends a control signal to the aspiration unit 312 to drive the same to perform an aspiration operation.

Then, as the operator steps on the ultrasonic pedal 305*a* on the foot switch 305, information on the ultrasonic pedal 305*a* switched ON by the operator stepping thereon is input to the switch sensing unit 314 of the perfusion/aspiration apparatus 303, and the result of sensing is transmitted to the control unit 313 of the perfusion/aspiration apparatus 303.

The control unit 313 of the perfusion/aspiration apparatus 303 notifies the perfusion unit 311 of the perfusion/aspiration apparatus 303, the control unit 307 of the ultrasonic wave output apparatus 302, and the switch sensing unit 308 to that effect. The perfusion unit 311 emits the amount of liquid according to a setting for washing a tissue of interest and for cooling the ultrasonic hand piece 304 from a perfusion opening, not shown, formed at the distal end of the ultrasonic hand piece 304.

The control unit 307 of the ultrasonic wave output apparatus 302 instructs the ultrasonic wave output unit 306 of the ultrasonic wave output apparatus 302 to generate an ultrasonic driving output which is sent to the ultrasonic hand piece 304 through the ultrasonic driving cable 316, causing an ultrasonic vibrator, not shown, in the ultrasonic hand piece 304 to ultrasonic vibrate. The ultrasonic vibrations are transmitted to an ultrasonically treatment piece at the distal end of the ultrasonic hand piece 304 to incise, coagulate, or emulsify a tissue of interest, onto which the ultrasonic treatment piece is pressed, with the ultrasonic vibrations.

In this event, a supplied liquid, oozed blood, destroyed tissue, and so on are aspirated through the aspiration tube 318 by an aspirating action of the aspiration unit 312 for recovery, thereby promptly removing excessive liquids and so on around the ultrasonic treatment piece to maintain an environment in which a continuous ultrasonic treatment is facilitated.

As the operator steps on the perfusion pedal 305*b* on the foot switch 305, information on this action is input to the switch sensing unit 314 of the perfusion/aspiration apparatus 303, and the result of sensing is transmitted to the control unit 313 of the perfusion/aspiration apparatus 303.

The control unit 313 of the perfusion/aspiration apparatus 303 notifies the perfusion unit 311 of the perfusion/aspiration apparatus 303 and the control unit 307 of the ultrasonic wave output apparatus 302 to that effect.

The perfusion unit 311 emits the amount of a liquid according to a setting for washing a tissue of interest from a perfusion opening, not shown, formed at the distal end of the ultrasonic hand piece 304. During this operation, excessive liquids and so on around the ultrasonic treatment piece are promptly removed by the aspirating action of the aspiration unit 312.

As described above, according to the eighth embodiment, the ultrasonic wave output apparatus 302 and the perfusion/aspiration apparatus 303 are connected such that the ultrasonic wave output apparatus 302, which does not have perfusion/aspiration means, operates in association with the perfusion/aspiration apparatus 303 connected thereto, and accordingly functions in a manner similar to an ultrasonic wave output apparatus which has such perfusion/aspiration means.

When the ultrasonic wave output apparatus 302 is not connected to the perfusion/aspiration apparatus 303, the two apparatus can be used independently. For example, for using the ultrasonic wave output apparatus independently (as an ultrasonic coagulation/incision apparatus without perfusion and aspiration functions), an ultrasonic coagulation/incision foot switch may be connected to a connection terminal of the switch sensing unit 308 to use the ultrasonic wave output apparatus 302 as an ultrasonic coagulation/incision apparatus.

Also, when the perfusion/aspiration apparatus 303 is not connected to another device such as the ultrasonic wave output apparatus 302 or the like, the perfusion/aspiration apparatus 303 can be used independently. In this case, a perfusion/aspiration foot switch or the like, not shown, may be connected to the switch sensing unit 314 to utilize the perfusion and aspiration operations of the perfusion/aspiration apparatus 303 independently as a perfusion apparatus, as an aspiration apparatus, or as a perfusion/aspiration apparatus, through operations on the perfusion/aspiration foot switch.

Further, when the ultrasonic wave output apparatus 302 and the perfusion/aspiration apparatus 303 are used without the communication cable 309 (i.e., they are not connected), the ultrasonic wave output apparatus 302 and the perfusion/aspiration apparatus 303 can be used under independent control schemes.

In other words, an existing ultrasonic coagulation/incision apparatus (without perfusion and aspiration functions) (or the ultrasonic wave output apparatus 302 configured to have the same functions) may be used in combination with the perfusion/aspiration apparatus 303 to perform a treatment which may additionally use the perfusion and aspiration functions, although the two apparatus do not operate in association.

In this configuration, since the two apparatus do not operate in association, they must be operated appropriately through foot switches or the like, respectively. However, since they can be controlled independently, a treatment can be performed in a condition largely different from that available for normal associative control, so that usage and techniques can be widely extended.

As described above, according to the eighth embodiment, the perfusion/aspiration apparatus 303 and ultrasonic wave output apparatus 302 can be configured into the ultrasonic operation system 301 which uses them in association by connecting them through the communication cable 309, or can be used independently of each other, thereby making it possible to realize a highly usable and extendable system.

(Ninth Embodiment)

Next, a ninth embodiment of the present invention will be described with reference to FIGS. 29 and 30.

Figure 29:
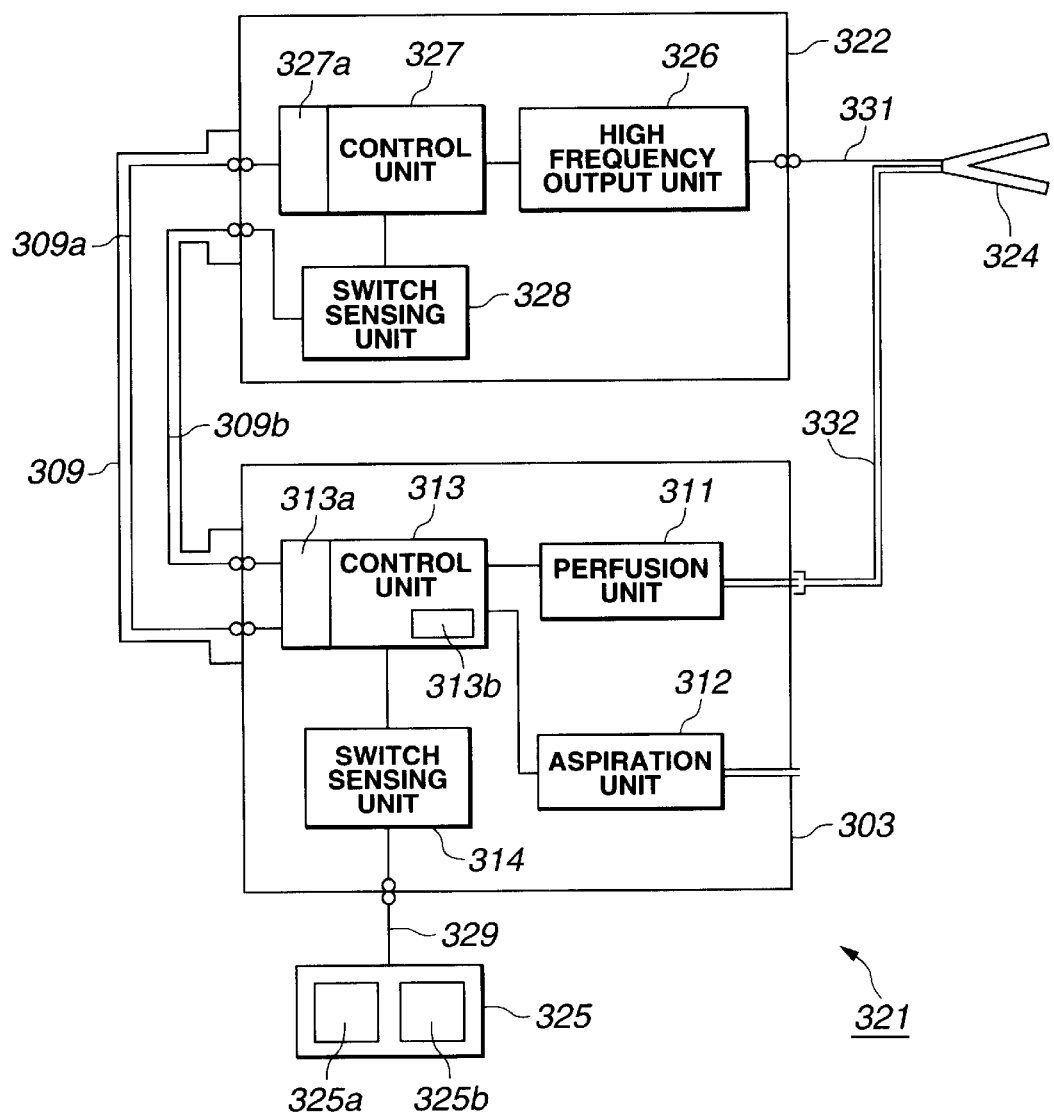

A high frequency operation system 321 according to the ninth embodiment illustrated in FIG. 29 comprises an electric knife apparatus (high frequency output apparatus) 322 for incising and coagulating a vital tissue of interest with a high frequency current; a perfusion/aspiration apparatus 303 connected to the electric knife apparatus 332 through a communication cable 309; a high frequency treatment piece connected to the electric knife apparatus 322 and the perfusion/aspiration apparatus 303, and grabbed by the operator for performing high frequency based treatments, more specifically, a bipolar forceps 324 as a forceps-based bipolar hand piece for clamping and coagulating a tissue of interest; and a foot switch 325 connected, for example, to the perfusion/aspiration apparatus 303 and operated by the operator to control a high frequency output operation and a perfusion operation.

In the high frequency operation system 321, the electric knife apparatus 322 and the perfusion/aspiration apparatus 303 are configured as separate units.

The electric knife apparatus 322 illustrated in FIG. 29 in turn comprises a high frequency output unit 326 for outputting a high frequency signal; a control unit 327 for controlling the operation of the high frequency output unit 326; and a switch sensing unit 328 for sensing a switching operation on an incision pedal 325*a* and a coagulation pedal 325*b* on the foot switch 325 through the perfusion/aspiration apparatus 303.

The control unit 327 includes a communication unit 327a for bidirectionally communicating with a device here the perfusion/aspiration apparatus 303. The communication unit 327a contains a generating means for generating ID information which allows for identification of the type of the electric knife apparatus 322 and also serves as unique information. In addition, the communication unit 327a includes an identifying means for identifying the type or the like of a device connected through the communication cable 309 based on ID information from the device.

The high frequency output unit 326 comprises a power supply, a control unit, an oscillator, an output unit, and a sensor, all of which are required therefore output a high frequency signal.

The perfusion/aspiration apparatus 303 has the same configuration as that previously described in the eighth embodiment, so that its components are designated the same reference numerals as those in the eighth embodiment, and description thereon is omitted.

The bipolar forceps 324 is connected to the high frequency output unit 326 of the electric knife apparatus 322 through a high frequency driving cable 331, and also connected to a perfusion unit 311 of the perfusion/aspiration apparatus 303 through a perfusion tube 332.

Likewise, in the ninth embodiment, their electric knife apparatus 322 and the perfusion/aspiration apparatus 303 are connected through the communication cable 309 to allow for the associative control.

Figure 27:
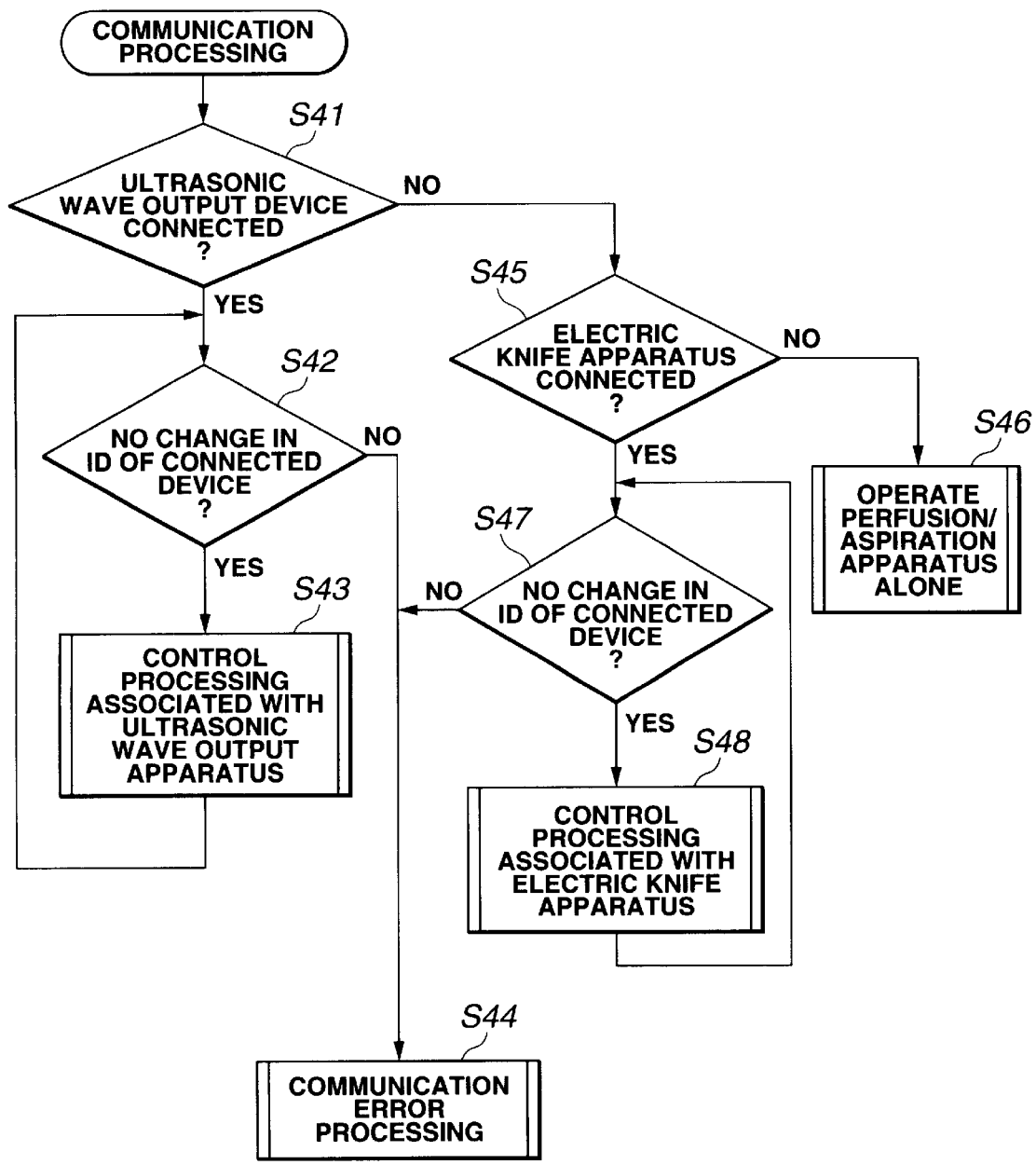

Communication processing implemented by the perfusion/aspiration apparatus 303 in the ninth embodiment proceeds as previously described in,connection with FIG. 27.

Briefly described, as the electric knife apparatus 322 and the perfusion/aspiration apparatus 303 are connected, they start communicating with each other. Since they have unique ID information, they recognize an apparatus currently connected thereto based on the ID information.

If they fail to recognize each other, the associative control is disabled, and instead the respective apparatus operate independently.

The ID information is mutually transmitted and received at regular intervals. If a different ID is returned, or if no return is received, a connection failure is recognized to generate an alarm to stop the operation of the apparatus, as communication error processing.

Figure 30:
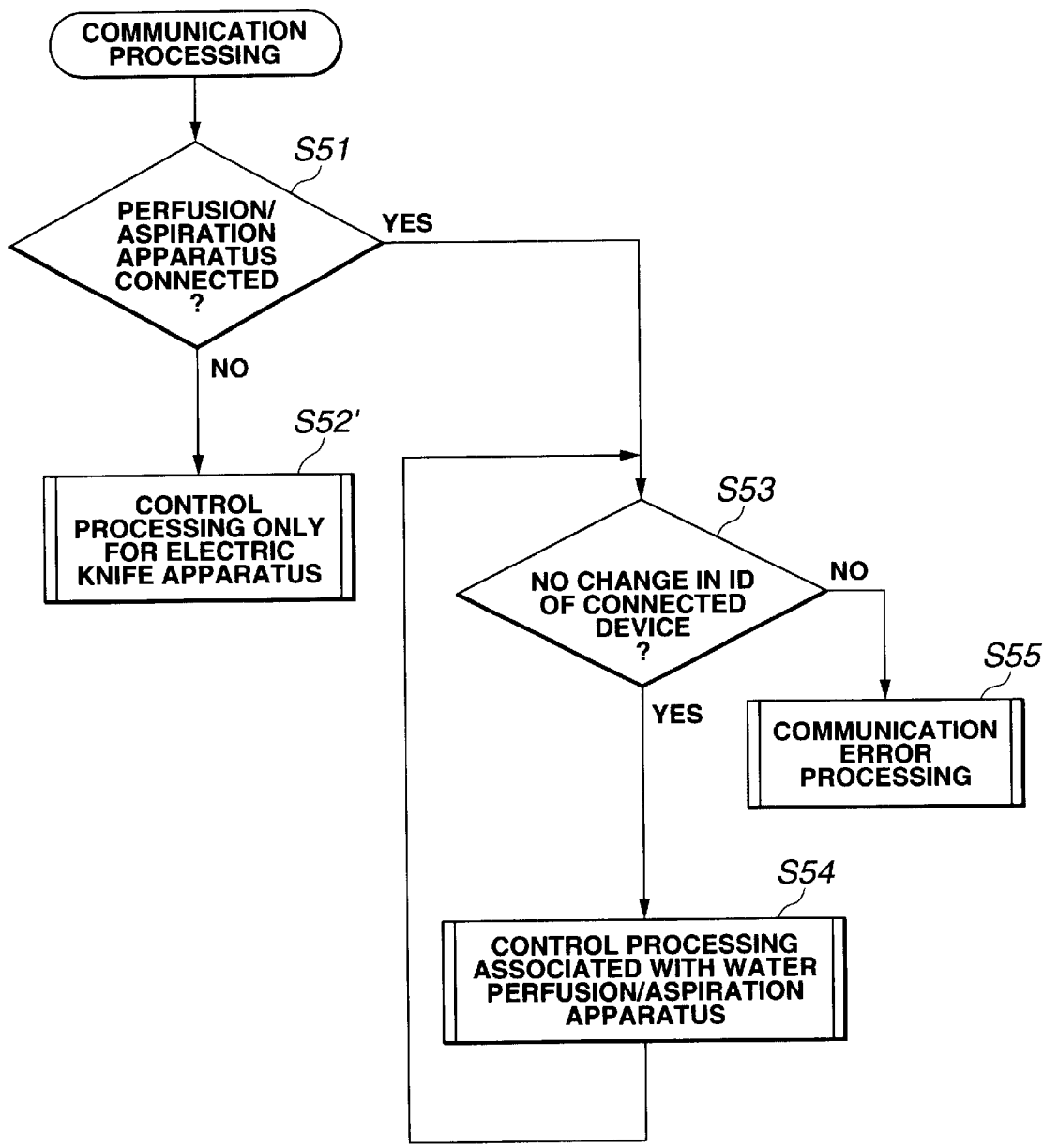

On the other hand, communication processing implemented by the electric knife apparatus 322 is performed as illustrated in FIG. 30. The processing illustrated in FIG. 30 is similar to that of FIG. 28 except for step S52 is replaced with independent control processing for the electric knife apparatus 322 represented by step S52' therefore the remaining steps in FIG. 30 are designated the same reference numerals and description thereon is omitted.

Next, a description will be given on the associative control which is performed when it is recognized through the ID information that the electric knife apparatus 322 and the perfusion/aspiration apparatus 303 are connected to each other.

As the operator steps on the incision pedal 325a on the foot switch 325, information on this action is input to the switch sensing unit 314 of the perfusion/aspiration apparatus 303, and the result of sensing is transmitted to the control unit 313 of the perfusion/aspiration apparatus 303.

The control unit 313 of the perfusion/aspiration apparatus 303 transmits the information to the control unit 327 of the electric knife apparatus 322.

The control unit 327 of the electric knife apparatus 322 transmits the information to the high frequency output unit 326 of the electric knife apparatus 322, causing a high frequency current to flow through a tissue of interest sandwiched by and between two electrodes, not shown at the distal end of the bipolar forceps 324 to perform a treatment for incising the tissue.

As the operator steps on the coagulation pedal 325b on the foot switch 325, information on this action is input to the switch sensing unit 314 of the perfusion/aspiration apparatus 303, and the result of sensing is transmitted to the control unit 313 of the perfusion/aspiration apparatus 303.

The control unit 313 of the perfusion/aspiration apparatus 303 transmits the information to the control unit 327 of the electric knife apparatus 322 and to the switch sensing unit 328.

The control unit 327 of the electric knife apparatus 322 transmits the information to the high frequency output unit 326 of the electric knife apparatus 322, causing a high frequency current to flow through a tissue of interest sandwiched by and between two electrodes, not shown, at the distal end of the bipolar forceps 324 to perform a treatment for coagulating the tissue.

Simultaneously, the control unit 313 of the perfusion/aspiration apparatus 303 transmits the information to the perfusion unit 311 of the perfusion/aspiration apparatus 303 to emit a liquid from a perfusion opening, not shown, at the distal end of the bipolar forceps 324.

On the other hand, the electric knife apparatus 322 and the perfusion/aspiration apparatus 303 are not connected through the communication cable 309 thus they can be used independently of each other, so that usage and techniques can be widely extended.

As appreciated, while the foregoing description has been made in connection with the electric knife apparatus 322 which is a device (apparatus) connected to the perfusion/aspiration apparatus 303, the rest of the ninth embodiment is similar to the eighth embodiment, and therefore similar advantages can be provided.

In the eighth and ninth embodiments, only one perfusion/aspiration apparatus is provided and an apparatus connected thereto can be recognized, so that the number of components can be reduced, and the reduced number of components can be used in an efficient manner.

Also, since the perfusion/aspiration apparatus 303 can be connected to either of the ultrasonic wave output apparatus 302 and the electric knife apparatus 322, economical and spatial savings can be provided.

Since the perfusion/aspiration apparatus 303 determines which of the ultrasonic wave output apparatus 302 and the electric knife apparatus 322 it is connected to, and operates only those functions which are required for the connected apparatus based on information on the connection, the user can use the perfusion/aspiration apparatus 303 with simple manipulations and good usability (operability).

(Tenth Embodiment)

Next, a tenth embodiment of the present invention will be described with reference to FIG. 31. In the foregoing description of the eighth of ninth embodiment, the ultrasonic operation foot switch 305 and the electric knife foot switch 325 connected to the perfusion/aspiration apparatus 303 are different from each other in connector shape or signal wiring from each other, such that the operation is prevented if the electric knife foot switch 325 is erroneously connected to the perfusion/aspiration apparatus 303 (for example, instead of connecting the ultrasonic operation foot switch 305, when the ultrasonic wave output apparatus 302 is connected to the perfusion/aspiration apparatus 303 through the communication cable 309).

In this way, unintended malfunctions (control) can be prevented. While this ensures safety, several inconvenient aspects are also presented such as increased cost due to a need for plurality of foot switches different in connector shape, an increase in the number of signal wires, and so on.

A high frequency operation system 321' of the tenth embodiment is such that the electric knife foot switch 325, for example in the high frequency operation system 321 of FIG. 29 is provided with a means for generating an identifying ID which allows for the recognition of the electric knife foot switch 325 when it is connected to the perfusion/aspiration apparatus 303.

Figure 31:
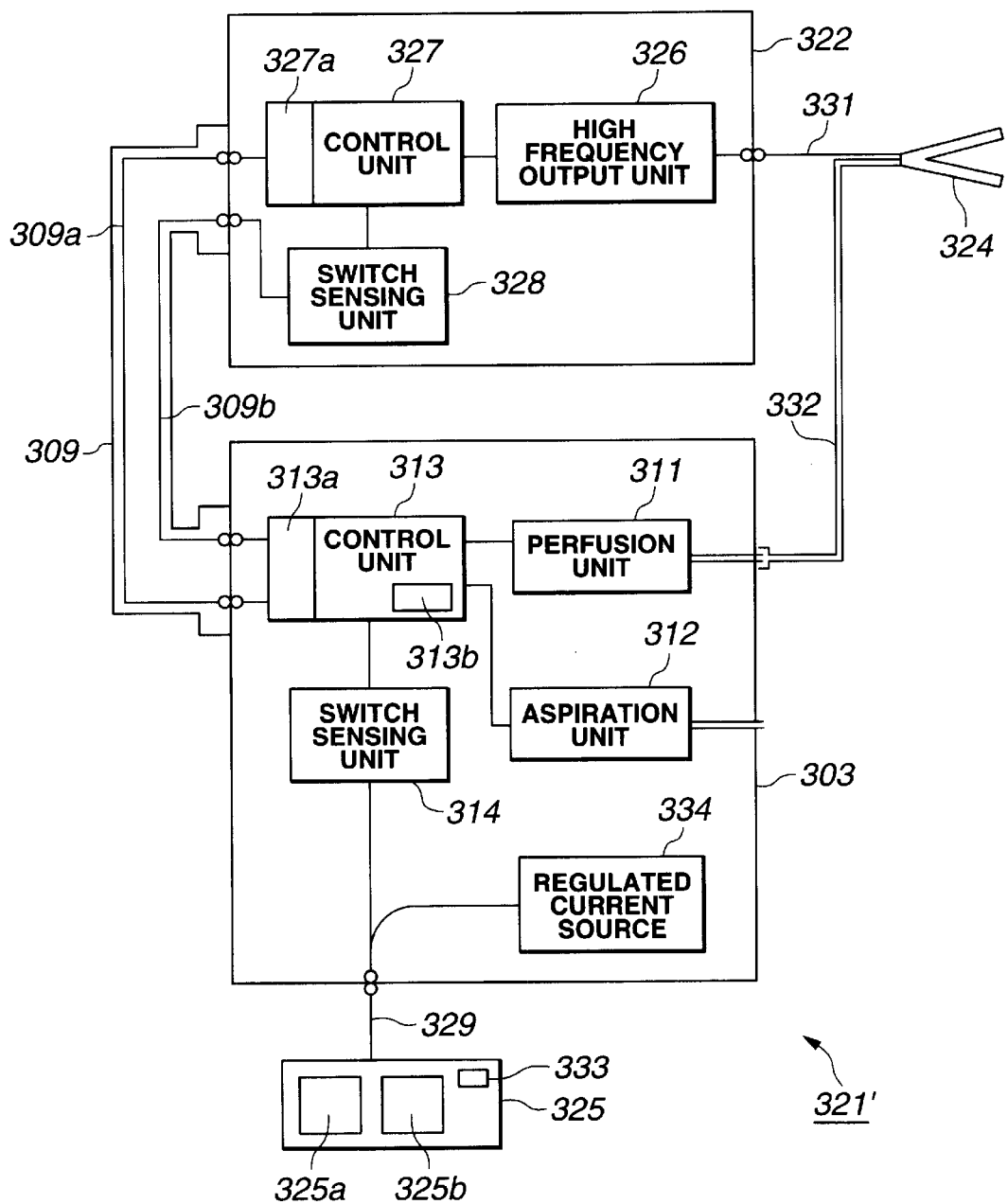
FIG. 31 is a block diagram generally illustrating the configuration of a high frequency treatment system according to a tenth embodiment of the present invention.

While in FIG. 31, the means for generating an identifying ID is provided in the electric knife foot switch 325, it may be also provided in the ultrasonic operation foot switch.

For identifying the foot switch, the foot switch 325 is provided, for example, with an identifying resistor 333 which is applied with a constant current from a regulated current source 334 provided in the perfusion/aspiration apparatus 303, and the level of a voltage generated across the identifying resistor 333 is relied on to identify the type of the foot switch connected to the perfusion/aspiration apparatus.

Thus, assuming, for example, that the ultrasonic wave output apparatus 302 and the perfusion/aspiration apparatus 303 are connected, and an electric surgical operation foot switch 325 is connected to the perfusion/aspiration apparatus 303, the ultrasonic wave output apparatus 302 is not compatible with this type of foot switch 325, so that the user is warned and notified to that effect, and is prompted to connect a proper foot switch.

Also, the type of the foot switch is to used on to switch the wiring for transmission from the perfusion/aspiration apparatus 303 to the ultrasonic wave output apparatus 302 or to the switch sensing unit 308 or 328 of the electric knife apparatus 322, so that the ultrasonic wave output apparatus 302 or the electric knife apparatus 322 can be controlled.

Further, the cable for connecting the control unit 313 of the perfusion/aspiration apparatus 303 with the ultrasonic wave output apparatus 302 and the cable for connecting the control unit 313 with the switch sensing unit 309 or 328 of the electric knife apparatus 332 can have the same connector, therefore the cable does not need to be exchanged each time a different apparatus is connected to the perfusion/aspiration apparatus 303.

Other than the foregoing, the tenth embodiment has similar advantages to those of the eighth or ninth embodiment.

While the foregoing tenth embodiment has been described for a foot switch as a switch means connected to the perfusion/aspiration apparatus 303, the present invention is not limited to the foot switch, but any other switch, for example, a remote switch such as a hand switch may be used instead.

It should be understood that embodiments created by partially combining the respective embodiments described above also fall under the scope of the present invention.

What is claimed is:

1. An electric treatment system comprising:
    a plurality of types of treatment tools each for performing a curative procedure;
    a first medical instrument to which at least one of said plurality of types of treatment tools is selectively and removably connected, including a first control unit for electrically controlling an operation of said at least one treatment tool connected thereto
    a second medical instrument to which at least one of said plurality types of treatment tools is selectively and removably connected unit for controlling an ancillary operation of said at least one treatment tools, said second medical instrument being removably connected to said first medical instrument;
    an identifier provided in each of said plurality of types of treatment tools for identifying said each treatment tool; and
    an identifier discriminating device provided in said first medical instrument for discriminating the type of a connected treatment tool from said identifier and communicating a discrimination result to said second medical instrument;
    wherein said second control unit selectively performs an associative control processing association with said first medical instrument and an independent control processing independent of said first medical instrument based on the discrimination result by said identifier discriminating device provided in said first medical instrument.

2. An electric treatment system according to claim 1, wherein said plurality of types of treatment tools each include an ultrasonic treatment tool for performing an ultrasonic-based treatment.

3. An electric treatment system according to claim 1, wherein said plurality of types of treatment tools include an electric knife treatment tool for performing a treatment with a high frequency current.

4. An electric treatment system according to claim 1, wherein said first medical instrument is an ultrasonic wave output apparatus for outputting ultrasonic waves.

5. An electric treatment system according to claim 4 wherein said operating parameters include an output setting for an ultrasonic wave output apparatus.

6. An electric treatment system according to claim 1, wherein said first medical instrument is an electric knife apparatus for outputting a high frequency current for an electric knife.

7. An electric treatment system according to claim 6, wherein said operating parameters include an output mode and an output setting for an electric knife apparatus.

8. An electric treatment system according to claim 1, wherein said second medical instrument is a perfusion/aspiration apparatus for performing perfusion and aspiration.

9. An electric treatment system according to claim 1, wherein said second medical instrument is a pneumoperitoneum apparatus for performing pneumoperitoneum.

10. An electric treatment system according to claim 1, wherein said first medical instrument and said second medical instrument are connected through a communication cable for communicating therebetween.

11. An electric treatment system according to claim 10, wherein said first medical instrument transmits information on the result of discrimination by said identifier discriminating device to said second medical instrument through said communication cable.

12. An electric treatment system according to claim 11, wherein said medical instrument relies on said information to determine whether or not said second medical instrument operates together with said first medical instrument.

13. An electric treatment system according to claim 11, wherein said second medical instrument relies on said information to determine operating parameters for which said second medical instrument operates together with said first medical instrument.

14. An electric treatment system according to claim 13, wherein said operating parameters include a perfusion amount and an aspiration amount when said second medical instrument is a perfusion/aspiration apparatus.

15. An electric treatment system according to claim 13, wherein said operating parameters include an abdominal pore pressure when said second medical instrument is a pneumoperitoneum apparatus.

16. An electric treatment system according to claim 1, wherein said first medical instrument and said second medical instrument are controlled by a controller for intensively controlling said medical instruments.

17. An electric treatment system according to claim 16, wherein said first medical instrument transmits information on the result of discrimination by said identifier discriminating device to said controller.

18. An electric treatment system according to claim 17, wherein said controller selectively indicates said second control unit of said second medical instrument to perform said associative control processing or said independent control processing in accordance with said information.

19. An electric treatment system according to claim 1, wherein said identifier is formed of a resistor.

20. An electric treatment system according to claim 1, wherein said second medical instrument includes a manipulation switch connected thereto for manipulating and indicating operations performed by said second medical instrument and said first medical instrument.

21. An electric treatment system according to claim 1, wherein said first medical instrument and said second medical instrument each comprise an ID information generator for generating ID information unique to said medical instrument and for transmitting said ID information through a communication cable.

22. An electric treatment system according to claim 21, wherein said first medical instrument and said second medical instrument each comprise an ID information identifier for identifying a medical instrument which has transmitted thereto through said communication cable.

23. An electric treatment system according to claim 22, wherein said first medical instrument determines whether or not said second medical instrument is connected thereto by transmitting and receiving said ID information to and from said second medical instrument.

24. An electric treatment system according to claim 23, wherein said medical instrument operates as a stand-alone medical instrument when said first medical instrument determines that said second medical instrument is not connected thereto by transmitting and receiving said ID information to and from said second medical instrument.

25. An electric treatment system according to claim 23, wherein when said first medical instrument determines that said second medical instrument is connected thereto by transmitting and receiving said ID information to and from said second medical instrument, said first medical instrument sends a control signal for selectively indicating to perform said associative control processing or said independent control processing to said second medical instrument depending on the type of the connected treatment tool.

26. An electric treatment system according to claim 1, further comprising an output switching apparatus connected to said first medical instrument for removably connecting a plurality of treatment tools simultaneously.

27. An electric treatment system according to claim 26, wherein said output switching apparatus is switched through a selection switch to make operable one of a plurality of treatment tools connected thereto.

28. An electric treatment system according to claim 1, wherein said first medical instrument and said second medical instrument include communication units, respectively, for communicating between said first medical instrument and said second medical instrument.

29. An electric treatment system comprising:

a plurality of types of treatment tools each for performing a treatment for a curative procedure;

a first medical instrument to which at least one of said plurality of types of treatment tools is selectively and removably connected, including a first control unit for electrically controlling an operation of said at least one treatment tool connected thereto;

a second medical instrument to which at least one of said plurality of types of treatment tools is selectively and removably connected, including a second control unit for controlling an ancillary operation of said at least one treatment tool, said second medical instrument being removably connected to said first medical instrument;

an information storing unit provided in each of said plurality of types of treatment tools;

a reader unit provided in each of said first medical instrument for reading information from said storing unit to discriminate at least the type of a treatment tool connected to said first medical instrument and communicating a discrimination result to said second medical instrument;

wherein said second control unit selectively performs an associative control processing in association with said first medical instrument and an independent control processing independent of said first medical instrument based on the discrimination result by said reader unit provided in said first medical instrument.

30. An electric treatment system according to claim 29, wherein said storing unit is a non-volatile electrically rewritable memory.

31. An electric treatment system according to claim 30, wherein said memory is EEPROM.

32. An electric treatment system according to claim 29, wherein said plurality of types of treatment tools include an ultrasonic treatment tool for performing an ultrasonic-based treatment.

33. An electric treatment system according to claim 29, wherein said plurality of types of treatment tools include an electric knife treatment tool for performing a treatment with a high frequency current.

34. An electric treatment system according to claim 29, wherein said first medical instrument is an ultrasonic wave output apparatus for outputting ultrasonic waves.

35. An electric treatment system according to claim 29, wherein said first medical instrument is an electric knife apparatus for outputting a high frequency current for an electric knife.

36. An electric treatment system according to claim 29, wherein said first medical instrument and said second medical instrument include communication units, respectively, for communicating between said first medical instrument and said second medical instrument.

* * * * *